United States Patent
Zhou et al.

(10) Patent No.: US 9,879,069 B2
(45) Date of Patent: Jan. 30, 2018

(54) ANTIBODY THERAPEUTICS THAT BIND OPRF

(71) Applicant: Sorrento Therapeutics, Inc., San Diego, CA (US)

(72) Inventors: Heyue Zhou, San Diego, CA (US); Gunnar F. Kaufmann, San Diego, CA (US)

(73) Assignee: Sorrento Therapeutics, Inc., San Diego, CA (US)

(*) Notice: Subject to any disclaimer, the term of this patent is extended or adjusted under 35 U.S.C. 154(b) by 0 days.

(21) Appl. No.: 14/839,791

(22) Filed: Aug. 28, 2015

(65) Prior Publication Data

US 2016/0060326 A1    Mar. 3, 2016

Related U.S. Application Data

(60) Provisional application No. 62/044,107, filed on Aug. 29, 2014.

(51) Int. Cl.
| | | |
|---|---|---|
| *C07K 16/00* | (2006.01) | |
| *A61K 39/108* | (2006.01) | |
| *C07K 16/12* | (2006.01) | |

(52) U.S. Cl.
CPC ...... *C07K 16/1214* (2013.01); *C07K 2317/21* (2013.01)

(58) Field of Classification Search
None
See application file for complete search history.

(56) References Cited

U.S. PATENT DOCUMENTS

| 2012/0058906 A1 | 3/2012 | Smider et al. |
| 2013/0266575 A1 | 10/2013 | Klade et al. |
| 2013/0323249 A1 | 12/2013 | Zhou et al. |

OTHER PUBLICATIONS

Rudikoff et al (Proc Natl Acad Sci USA 1982 vol. 79 p. 1979).*
MacCallum et al. J. Mol. Biol. (1996) 262,732-745.*
Pascalis et al. The Journal of Immunology (2002) 169, 3076-3084.*
Casset et al. (2003) BBRC 307, 198-205.*
Vajdos et al. (2002) 320, 415-428.*
Chen et al. J. Mol. Bio. (1999) 293, 865-881.*
Wu et al. J. Mol. Biol. (1999) 294, 151-162.*
Rudinger et al. (Jun. 1976. Peptide Hormones. Biol.Council. pp. 5-7.*
Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
International Search Report and Written Opinion for International Application No. PCT/US2015/047576 dated Jan. 8, 2016.

* cited by examiner

*Primary Examiner* — Jennifer Graser
(74) *Attorney, Agent, or Firm* — Womble Bond Dickinson (US) LLP

(57) ABSTRACT

There is disclosed compositions and methods relating to or derived from anti-OprF and anti-OprI antibodies. More specifically, there is disclosed fully human antibodies that bind OprF and OprI, OprF and OprI-antibody binding fragments and derivatives of such antibodies, and OprF and OprI-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having *Pseudomonas aeruginosa* infections. There is disclosed a method for treating or preventing *Pseudomonas aeruginosa* infections, wherein the disease is selected from the group consisting of burns, surgical site infections, diabetic foot ulcers, infected wounds, and cystic fibrosis.

25 Claims, 8 Drawing Sheets

ANTIBODY THERAPEUTICS THAT BIND OPRF

CROSS REFERENCE TO RELATED APPLICATION

The present patent application claims priority from U.S. provisional patent application 62/044,107 filed 29 Aug. 2014.

TECHNICAL FIELD

The present disclosure provides compositions and methods relating to or derived from anti-OprF and anti-OprI antibodies. More specifically, the present disclosure provides fully human antibodies that bind OprF and OprI, OprF and OprI-antibody binding fragments and derivatives of such antibodies, and OprF and OprI-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or preventing spread of subjects having *Pseudomonas aeruginosa* infections. The present disclosure further provides a method for treating or preventing a disease caused by *Pseudomonas aeruginosa* infections, wherein the disease is selected from the group consisting of burns, surgical site infections, diabetic foot ulcers, infected wounds, and cystic fibrosis.

BACKGROUND

*Pseudomonas aeruginosa* is a common environmental microorganism that has acquired the ability to take advantage of weaknesses in the host defenses to become an opportunistic pathogen in humans. It is the most common Gram-negative cause of hospital-acquired infections. In general, *P. aeruginosa* infections are especially troublesome due to the fact that this bacterium continues to acquire resistance to commonly-used antibiotics. *P. aeruginosa* is a part of the drug-resistant ESKAPE microbe group, which considered one of the biggest threats infectious diseases today. Notably, it is intrinsically resistant to a number of antibiotics due to its multidrug efflux pump systems, and a bacterial envelop that has low permeability. These attributes, plus a predilection towards hypermutation and efficient horizontal gene transfers of antibiotic resistance genes give rise to infections that become refractory to antibiotic therapy.

*Pseudomonas aeruginosa* Infections.

*P. aeruginosa* is the most common Gram-negative pathogen isolated from chronic wound infections. Infections of the dermis, including burns, surgical-site infections and non-healing diabetic foot ulcers affect over a million people, cause thousands of amputations and deaths and cost billions of dollars in direct medical costs in the United States annually. The microbial populations of these infections are biofilm-associated and display increased tolerance to antimicrobials.

In burn wound infections, *P. aeruginosa* is the most common Gram-negative isolated and is associated with very high mortality. The American Burn Association estimates that approximately 500,000 individuals in the United States are treated for thermal injury each year, resulting in over 4,000 deaths. Worldwide, the numbers are significantly larger, especially in areas of conflict. As thermal injury removes or impairs the body's natural barrier to microbes, the cause of death in over 75% of these burned individuals is infection. While not as dramatic, secondary sepsis, originating from infected wounds, affects trauma patients and those with surgical-site infections. Approximately 10% of burn patients become infected with *P. aeruginosa* and of those, up to 75% die of septicemia. Sepsis is the most common cause of death among ICU patients, and ranks 10th among all patients.

Most prominent is the role of *P. aeruginosa* in patients suffering from cystic fibrosis (CF). CF is the most common lethal inherited genetic disorder that follows an autosomal recessive inheritance pattern in Caucasian people. Approximately 30,000 people in the United States suffer from CF. Due to impaired lung defense functions, CF patients are vulnerable targets for *P. aeruginosa*. As a result, infections with *P. aeruginosa*, and the damage caused by the inflammatory infection process leads to death in more than 90% of CF patients.

OprF and OprI.

Both proteins are *P. aeruginosa* outer membrane proteins that are surface exposed and antigenically conserved in various strains of *P. aeruginosa*. Antibodies against OprF are associated with protection in animal models and are present following immunization in humans. It has also been reported that OprF function is required for full *P. aeruginosa* virulence as it is a modulator of quorum sensing. The binding of OprF to interferon-γ (IFN-γ) has been shown to up-regulate another adhesin, LecA, through quorum sensing. Activation of IFN-γ also increased expression of pyocyanin, which is another quorum-sensing-related virulence product. Activation of LecA and pyocyanin leads to the disruption of epithelial cell function. OprF is essential for microaerobic growth of *P. aeruginosa*, and expression is also imperative for the formation of anaerobic biofilms. OprF mutants are unable to adhere to animal cells and lack the ability to secrete ExoT and ExoS toxins via the type III secretion system. An OprF mutant was deficient in the production of signal molecules N-(3-oxododecanoyl)-1-homoserine lactone and N-butanoyl-1-homoserine lactone, both of which regulate the timing and production of pyocyanin, elastase, lectin PA-1L and exotoxin A. There, there is a need in the art for effective anti-infective agents.

SUMMARY

The present disclosure provides a fully human antibody of an IgG class that binds to a OprF and OprI epitope with a binding affinity of at least $10^{-6}$M, which has a heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called OFA1 herein), SEQ ID NO. 3/SEQ ID NO. 4 (called OFC7 herein), SEQ ID NO. 5/SEQ ID NO. 6 (called OFC10 herein), SEQ ID NO. 7/SEQ ID NO. 8 (called OFF7 herein), SEQ ID NO. 9/SEQ ID NO. 10 (called OFF8 herein), SEQ ID NO. 11/SEQ ID NO. 12 (called OFG5 herein), SEQ ID NO. 13/SEQ ID NO. 14 (called OFH10 herein), SEQ ID NO. 15/SEQ ID NO. 16 (called OIA1 herein), SEQ ID NO. 17/SEQ ID NO. 18 (called OIA10 herein), SEQ ID NO. 19/SEQ ID NO. 20 (called OIA2 herein), SEQ ID NO. 21/SEQ ID NO. 22 (called OIA4 herein), SEQ ID NO. 23/SEQ ID NO. 24 (called OIA5 herein), SEQ ID NO. 25/SEQ ID NO. 26 (called OIA6 herein), SEQ ID NO. 27/SEQ ID NO. 28 (called OIA7 herein), SEQ ID NO. 29/SEQ ID NO. 30 (called OIA8 herein), SEQ ID NO. 31/SEQ ID NO. 32 (called OIA9 herein), SEQ ID NO. 33/SEQ ID NO. 34 (called OIB1 herein), SEQ ID NO. 35/SEQ ID NO. 36 (called OIB11 herein), SEQ ID NO. 37/SEQ ID NO. 38 (called OIB12 herein), SEQ ID NO. 39/SEQ ID NO. 40 (called OIB2 herein), SEQ ID NO. 41/SEQ ID NO. 42 (called OIB3 herein), SEQ ID NO. 43/SEQ ID NO. 44 (called OIB8 herein), SEQ ID NO. 45/SEQ ID NO. 46 (called OIB9 herein), SEQ ID NO. 47/SEQ ID NO. 48 (called OIC1 herein), SEQ ID NO. 49/SEQ ID NO. 50 (called OIC3 herein), SEQ ID NO. 51/SEQ ID NO. 52 (called OIC6 herein), SEQ ID NO. 53/SEQ ID NO. 54 (called OIC9 herein), SEQ ID NO. 55/SEQ ID NO. 56 (called OID1 herein), SEQ ID NO. 57/SEQ ID NO. 58 (called OID10 herein), SEQ ID NO. 59/SEQ ID NO. 60 (called OID12 herein), SEQ ID NO. 61/SEQ ID NO. 62 (called OID3 herein), SEQ ID NO. 63/SEQ ID NO. 64 (called OID3 herein), SEQ ID NO. 65/SEQ ID NO. 66 (called OID5 herein), SEQ ID NO. 67/SEQ ID NO. 68 (called OID6 herein), SEQ ID NO. 69/SEQ ID NO. 70 (called OID8 herein), SEQ ID NO. 71/SEQ ID NO. 72 (called OIE12 herein), SEQ ID NO. 73/SEQ ID NO. 74 (called OIE3 herein), SEQ ID NO. 75/SEQ ID NO. 76 (called OIE9 herein), SEQ ID NO. 77/SEQ ID NO. 78 (called OIF10 herein), SEQ ID NO. 79/SEQ ID NO. 80 (called OIF4 herein), SEQ ID NO. 81/SEQ ID NO. 82 (called OIF6 herein), SEQ ID NO. 83/SEQ ID NO. 84 (called OIF9 herein), SEQ ID NO. 85/SEQ ID NO. 86 (called OIG1 herein), SEQ ID NO. 87/SEQ ID NO. 88 (called OIG11 herein), SEQ ID NO. 89/SEQ ID NO. 90 (called OIG12 herein), SEQ ID NO. 91/SEQ ID NO. 92 (called OIG2 herein), SEQ ID NO. 93/SEQ ID NO. 94 (called OIG5 herein), SEQ ID NO. 95/SEQ ID NO. 96 (called OIG7 herein), SEQ ID NO. 97/SEQ ID NO. 98 (called OIG8 herein), SEQ ID NO. 99/SEQ ID NO. 100 (called OIG9 herein), SEQ ID NO. 101/SEQ ID NO. 102 (called OIH10 herein), SEQ ID NO. 103/SEQ ID NO. 104 (called OIH11 herein), SEQ ID NO. 105/SEQ ID NO. 106 (called OIH12 herein), SEQ ID NO. 107/SEQ ID NO. 108 (called OIH3 herein), SEQ ID NO. 109/SEQ ID NO. 110 (called OIH5 herein), SEQ ID NO. 111/SEQ ID NO. 112 (called OIH6 herein), SEQ ID NO. 113/SEQ ID NO. 114 (called FEA2 herein), SEQ ID NO. 115/SEQ ID NO. 116 (called FEA3 herein), SEQ ID NO. 117/SEQ ID NO. 118 (called FEA4 herein), SEQ ID NO. 119/SEQ ID NO. 120 (called FEAT herein), SEQ ID NO. 121/SEQ ID NO. 122 (called FEA12 herein), SEQ ID NO. 123/SEQ ID NO. 124 (called FEC2 herein), SEQ ID NO. 125/SEQ ID NO. 126 (called FEC4 herein), SEQ ID NO. 127/SEQ ID NO. 128 (called FEC10 herein), SEQ ID NO. 129/SEQ ID NO. 130 (called FED2 herein), SEQ ID NO. 131/SEQ ID NO. 132 (called FED3 herein), SEQ ID NO. 133/SEQ ID NO. 134 (called FED8 herein), SEQ ID NO. 135/SEQ ID NO. 136 (called FEE10 herein), SEQ ID NO. 137/SEQ ID NO. 138 (called FEF8 herein), SEQ ID NO. 139/SEQ ID NO. 140 (called FEH2 herein), SEQ ID NO. 141/SEQ ID NO. 142 (called FEH7 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof. Preferably, the fully human antibody Fab fragment has both a heavy chain variable domain region and a light chain variable domain region wherein the antibody has a heavy chain/light chain variable domain sequence selected from the group consisting SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO.

29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, and combinations thereof.

The present disclosure further provides a method for treating or preventing spread of infection for subjects having *Pseudomonas aeruginosa* infections. comprising administering an anti-OprF and anti-OprI polypeptide, wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and combinations thereof, and that has a light chain variable domain sequence that is at least 95% identical to the amino acid consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and combinations thereof, and that has the light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and combinations thereof, and that has the light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2 (called OFA1 herein), SEQ ID NO. 3/SEQ ID NO. 4 (called OFC7 herein), SEQ ID NO. 5/SEQ ID NO. 6 (called OFC10 herein), SEQ ID NO. 7/SEQ ID NO. 8 (called OFF7 herein), SEQ ID NO. 9/SEQ ID NO. 10 (called OFF8 herein), SEQ ID NO. 11/SEQ ID NO. 12 (called OFG5 herein), SEQ ID NO. 13/SEQ ID NO. 14 (called OFH10 herein), SEQ ID NO. 15/SEQ ID NO. 16 (called OIA1 herein), SEQ ID NO. 17/SEQ ID NO. 18 (called OIA10 herein), SEQ ID NO. 19/SEQ ID NO. 20 (called OIA2 herein), SEQ ID NO. 21/SEQ ID NO. 22 (called OIA4 herein), SEQ ID NO. 23/SEQ ID NO. 24 (called OIA5 herein), SEQ ID NO. 25/SEQ ID NO. 26 (called OIA6 herein), SEQ ID NO. 27/SEQ ID NO. 28 (called OIA7 herein), SEQ ID NO. 29/SEQ ID NO. 30 (called OIA8 herein), SEQ ID NO. 31/SEQ ID NO. 32 (called OIA9 herein), SEQ ID NO. 33/SEQ ID NO. 34 (called OIB1 herein), SEQ ID NO. 35/SEQ ID NO. 36 (called OIB11 herein), SEQ ID NO. 37/SEQ ID NO. 38 (called OIB12 herein), SEQ ID NO. 39/SEQ ID NO. 40 (called OIB2 herein), SEQ ID NO. 41/SEQ ID NO. 42 (called OIB3 herein), SEQ ID NO. 43/SEQ ID NO. 44 (called OIB8 herein), SEQ ID NO. 45/SEQ ID NO. 46 (called OIB9 herein), SEQ ID NO. 47/SEQ ID NO. 48 (called OIC1 herein), SEQ ID NO. 49/SEQ ID NO. 50 (called OIC3 herein), SEQ ID NO. 51/SEQ ID NO. 52 (called OIC6 herein), SEQ ID NO. 53/SEQ ID NO. 54 (called OIC9 herein), SEQ ID NO. 55/SEQ ID NO. 56 (called OID1 herein), SEQ ID NO. 57/SEQ ID NO. 58 (called OID10 herein), SEQ ID NO. 59/SEQ ID NO. 60 (called OID12 herein), SEQ ID NO. 61/SEQ ID NO. 62 (called OID3 herein), SEQ ID NO. 63/SEQ ID NO. 64 (called OID3 herein), SEQ ID NO. 65/SEQ ID NO. 66 (called OID5 herein), SEQ ID NO. 67/SEQ ID NO. 68 (called OID6 herein), SEQ ID NO. 69/SEQ ID NO. 70 (called OID8 herein), SEQ ID NO. 71/SEQ ID NO. 72 (called OIE12 herein), SEQ ID NO. 73/SEQ ID NO. 74 (called OIE3 herein), SEQ ID NO. 75/SEQ ID NO. 76 (called OIE9 herein), SEQ ID NO. 77/SEQ ID NO. 78 (called OIF10 herein), SEQ ID NO. 79/SEQ ID NO. 80 (called OIF4 herein), SEQ ID NO. 81/SEQ ID NO. 82 (called OIF6 herein), SEQ ID NO. 83/SEQ ID NO. 84 (called OIF9 herein), SEQ ID NO. 85/SEQ ID NO. 86 (called OIG1 herein), SEQ ID NO. 87/SEQ ID NO. 88 (called OIG11 herein), SEQ ID NO. 89/SEQ ID NO. 90 (called OIG12 herein), SEQ ID NO. 91/SEQ ID NO. 92 (called OIG2 herein), SEQ ID NO. 93/SEQ ID NO. 94 (called OIG5 herein), SEQ ID NO. 95/SEQ ID NO. 96 (called OIG7 herein), SEQ ID NO. 97/SEQ ID NO. 98 (called OIG8 herein), SEQ ID NO. 99/SEQ ID NO. 100 (called OIG9 herein), SEQ ID NO. 101/SEQ ID NO. 102 (called OIH10 herein), SEQ ID NO. 103/SEQ ID NO. 104 (called OIH11 herein), SEQ ID NO. 105/SEQ ID NO. 106 (called OIH12 herein), SEQ ID NO. 107/SEQ ID NO. 108 (called OIH3 herein), SEQ ID NO. 109/SEQ ID NO. 110 (called OIH5 herein), SEQ ID NO. 111/SEQ ID NO. 112 (called OIH6 herein), SEQ ID NO. 113/SEQ ID NO. 114 (called FEA2 herein), SEQ ID NO. 115/SEQ ID NO. 116 (called FEA3 herein), SEQ ID NO. 117/SEQ ID NO. 118 (called FEA4 herein), SEQ ID NO. 119/SEQ ID NO. 120 (called FEAT herein), SEQ ID NO. 121/SEQ ID NO. 122 (called FEA12 herein), SEQ ID NO. 123/SEQ ID NO. 124 (called FEC2 herein), SEQ ID NO. 125/SEQ ID NO. 126 (called FEC4 herein), SEQ ID NO. 127/SEQ ID NO. 128 (called FEC10 herein), SEQ ID NO. 129/SEQ ID NO. 130 (called FED2 herein), SEQ ID NO. 131/SEQ ID NO. 132 (called FED5 herein), SEQ ID NO. 133/SEQ ID NO. 134 (called FED8 herein), SEQ ID NO. 135/SEQ ID NO. 136 (called FEE10 herein), SEQ ID NO. 137/SEQ ID NO. 138 (called FEF8 herein), SEQ ID NO. 139/SEQ ID NO. 140 (called FEH2 herein), SEQ ID NO. 141/SEQ ID NO. 142 (called FEH7 herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, and combinations thereof.

Preferably, the method for treating or preventing a disease caused by *Pseudomonas aeruginosa* infections, wherein the disease is selected from the group consisting of burns, surgical site infections, diabetic foot ulcers, infected wounds, and cystic fibrosis.

DESCRIPTION OF THE DRAWINGS

FIG. 1 shows OPrI antibodies. FIG. 2 shows OprF single chain antibodies. FIG. 3 shows OprF fully human IgG antibodies and FIG. 4 shows OprF epitope 8 single chain antibodies.

DETAILED DESCRIPTION

Figure 1:
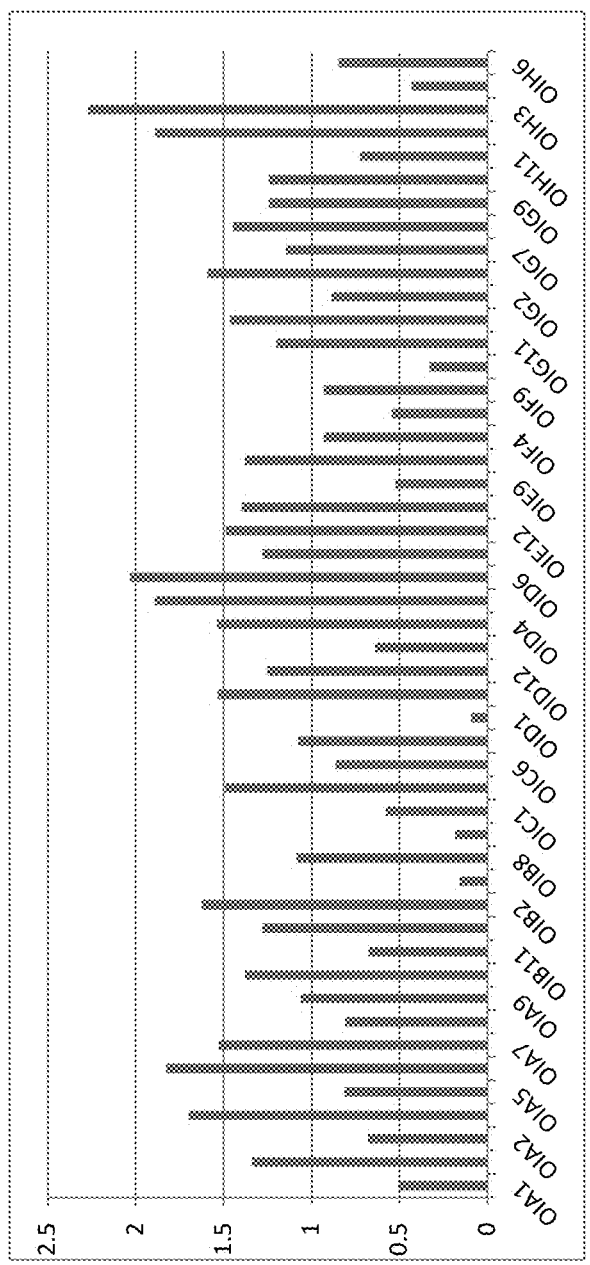
FIGS. 1-4 show a bar graph of various listed antibodies binding to their respective antigen OprF or OprI based on a standard ELISA assay to measure antibody-target binding.
Figure 2:
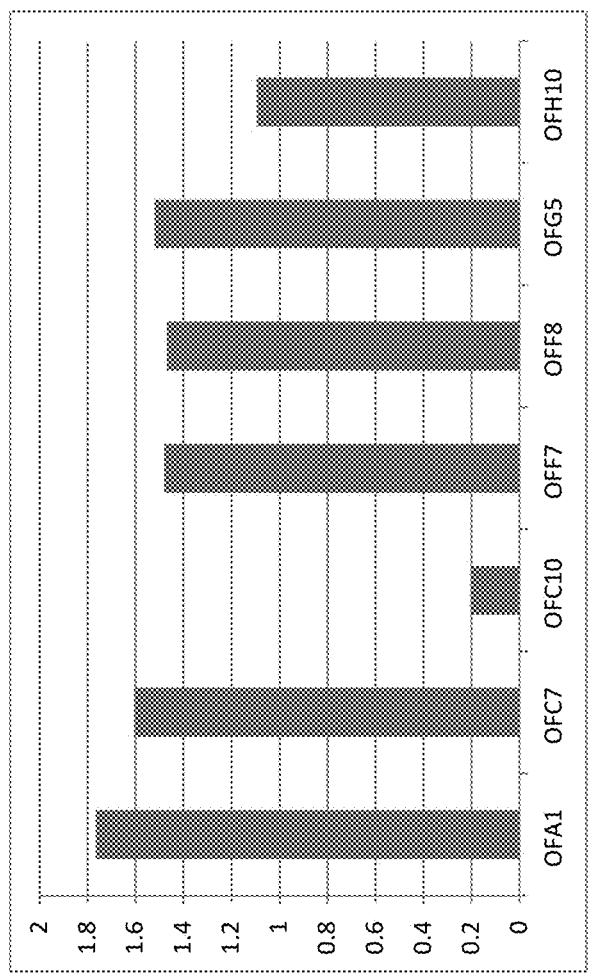
Figure 3:
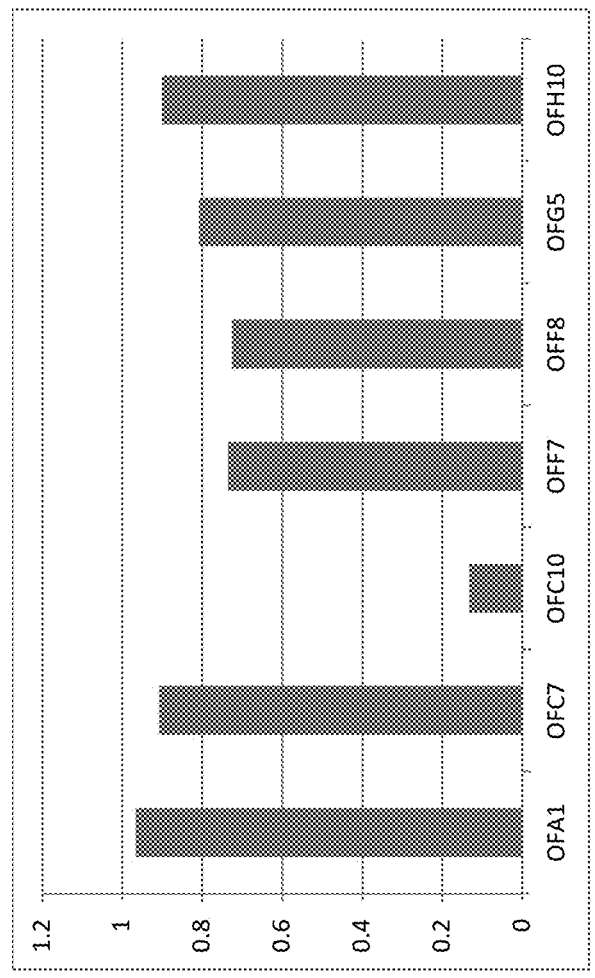
Figure 4:
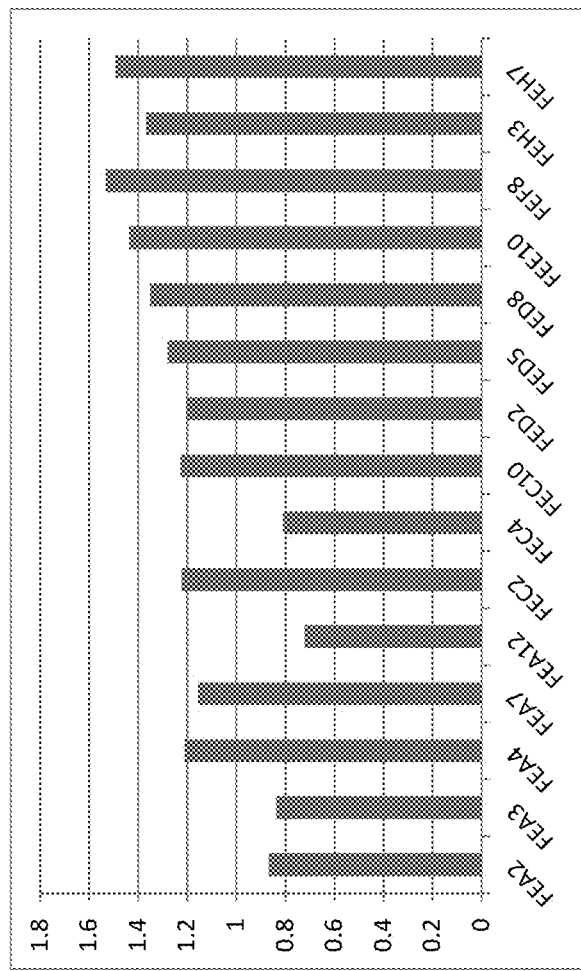
Figure 5:
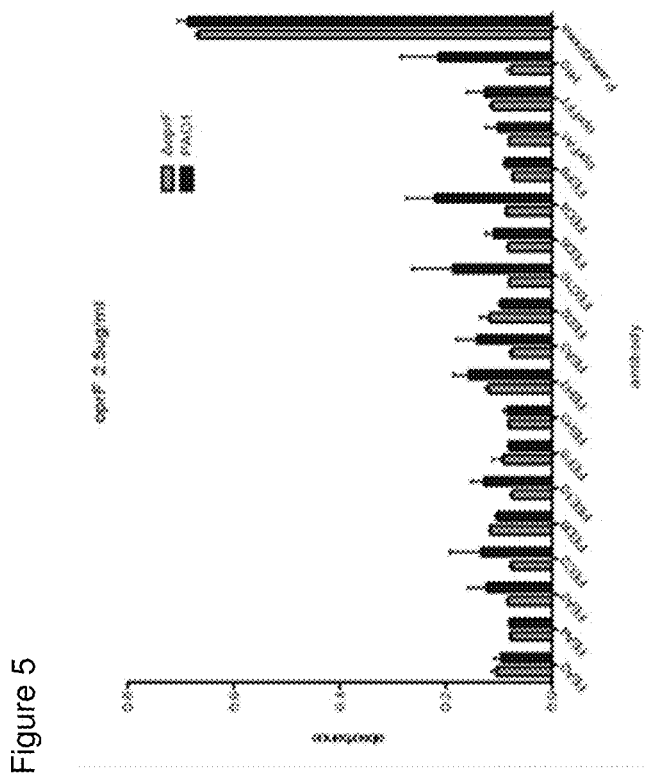
FIG. 5 shows a whole cell *Pseudomonas* ELISA to characterize binding specificity of anti-OprF antibodies. The blue bar should be larger than the green signal to indicate preferential binding to wild type *Pseudomonas* (OprF-positive cells).
Figure 6:
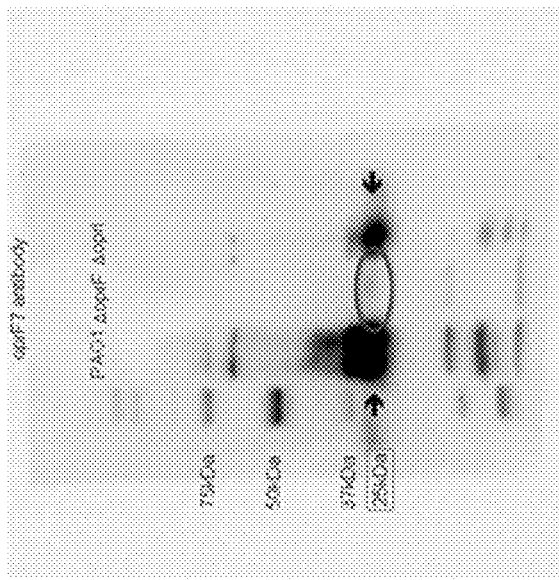
FIG. 6 shows a Western blot analysis of anti-OprI antibody oprIA5. This blot shows that the mAb reacts with cell lysates from wildtype *P. aeruginosa* as well as OprF mutant cells but not with OprI-deficient cell lysate.
Figure 7:
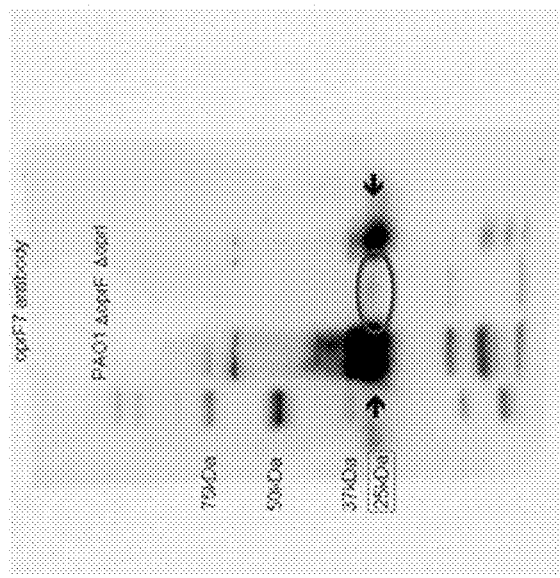
FIG. 7 shows a western blot analysis of anti-OprI antibody STI-oprFF7. This blot shows that the mAb reacts with cell lysates from wild type *P. aeruginosa* as well as OprI mutant cells but not with OprF-deficient cell lysate.
Figure 8A:
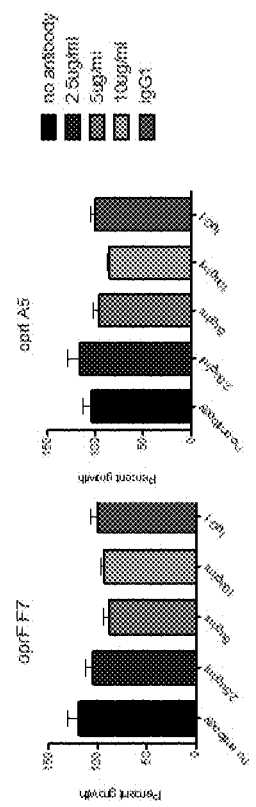
FIG. 8A shows attachment prevention assay's normalized to IgG1 treatment.
Figure 8B:
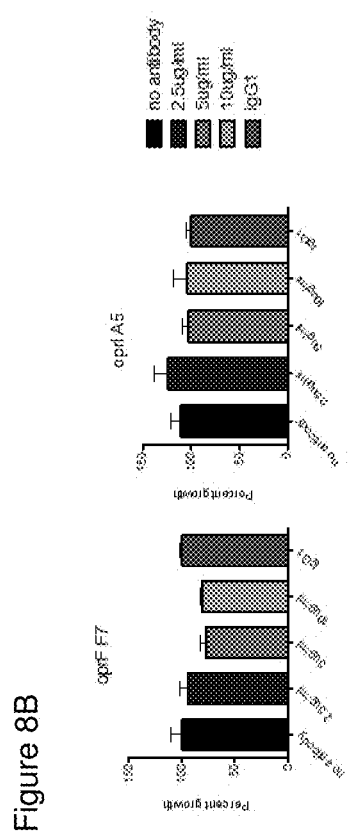
FIG. 8B shows biofilm disruption assays, normalized to IgG1 treatment.

The present disclosure provides a fully human antibody of an IgG class that binds to a OprF and OprI epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called OFA1 herein), SEQ ID NO. 3/SEQ ID NO. 4 (called OFC7 herein), SEQ ID NO. 5/SEQ ID NO. 6 (called OFC10 herein), SEQ ID NO. 7/SEQ ID NO. 8 (called OFF7 herein), SEQ ID NO. 9/SEQ ID NO. 10 (called OFF8 herein), SEQ ID NO. 11/SEQ ID NO. 12 (called OFG5 herein), SEQ ID NO. 13/SEQ ID NO. 14 (called OFH10 herein), SEQ ID NO. 15/SEQ ID NO. 16 (called OIA1 herein), SEQ ID NO. 17/SEQ ID NO. 18 (called OIA10 herein), SEQ ID NO. 19/SEQ ID NO. 20

(called OIA2 herein), SEQ ID NO. 21/SEQ ID NO. 22
(called OIA4 herein), SEQ ID NO. 23/SEQ ID NO. 24
(called OIA5 herein), SEQ ID NO. 25/SEQ ID NO. 26
(called OIA6 herein), SEQ ID NO. 27/SEQ ID NO. 28
(called OIA7 herein), SEQ ID NO. 29/SEQ ID NO. 30
(called OIA8 herein), SEQ ID NO. 31/SEQ ID NO. 32
(called OIA9 herein), SEQ ID NO. 33/SEQ ID NO. 34
(called OIB1 herein), SEQ ID NO. 35/SEQ ID NO. 36
(called OIB11 herein), SEQ ID NO. 37/SEQ ID NO. 38
(called OIB12 herein), SEQ ID NO. 39/SEQ ID NO. 40
(called OIB2 herein), SEQ ID NO. 41/SEQ ID NO. 42
(called OIB3 herein), SEQ ID NO. 43/SEQ ID NO. 44
(called OIB8 herein), SEQ ID NO. 45/SEQ ID NO. 46
(called OIB9 herein), SEQ ID NO. 47/SEQ ID NO. 48
(called OIC1 herein), SEQ ID NO. 49/SEQ ID NO. 50
(called OIC3 herein), SEQ ID NO. 51/SEQ ID NO. 52
(called OIC6 herein), SEQ ID NO. 53/SEQ ID NO. 54
(called OIC9 herein), SEQ ID NO. 55/SEQ ID NO. 56
(called OID1 herein), SEQ ID NO. 57/SEQ ID NO. 58
(called OID10 herein), SEQ ID NO. 59/SEQ ID NO. 60
(called OID12 herein), SEQ ID NO. 61/SEQ ID NO. 62
(called OID3 herein), SEQ ID NO. 63/SEQ ID NO. 64
(called OID3 herein), SEQ ID NO. 65/SEQ ID NO. 66
(called OID5 herein), SEQ ID NO. 67/SEQ ID NO. 68
(called OID6 herein), SEQ ID NO. 69/SEQ ID NO. 70
(called OID8 herein), SEQ ID NO. 71/SEQ ID NO. 72
(called OIE12 herein), SEQ ID NO. 73/SEQ ID NO. 74
(called OIE3 herein), SEQ ID NO. 75/SEQ ID NO. 76
(called OIE9 herein), SEQ ID NO. 77/SEQ ID NO. 78
(called OIF10 herein), SEQ ID NO. 79/SEQ ID NO. 80
(called OIF4 herein), SEQ ID NO. 81/SEQ ID NO. 82
(called OIF6 herein), SEQ ID NO. 83/SEQ ID NO. 84
(called OIF9 herein), SEQ ID NO. 85/SEQ ID NO. 86
(called OIG1 herein), SEQ ID NO. 87/SEQ ID NO. 88
(called OIG11 herein), SEQ ID NO. 89/SEQ ID NO. 90
(called OIG12 herein), SEQ ID NO. 91/SEQ ID NO. 92
(called OIG2 herein), SEQ ID NO. 93/SEQ ID NO. 94
(called OIG5 herein), SEQ ID NO. 95/SEQ ID NO. 96
(called OIG7 herein), SEQ ID NO. 97/SEQ ID NO. 98
(called OIG8 herein), SEQ ID NO. 99/SEQ ID NO. 100
(called OIG9 herein), SEQ ID NO. 101/SEQ ID NO. 102
(called OIH10 herein), SEQ ID NO. 103/SEQ ID NO. 104
(called OIH11 herein), SEQ ID NO. 105/SEQ ID NO. 106
(called OIH12 herein), SEQ ID NO. 107/SEQ ID NO. 108
(called OIH3 herein), SEQ ID NO. 109/SEQ ID NO. 110
(called OIH5 herein), SEQ ID NO. 111/SEQ ID NO. 112
(called OIH6 herein), SEQ ID NO. 113/SEQ ID NO. 114
(called FEA2 herein), SEQ ID NO. 115/SEQ ID NO. 116
(called FEA3 herein), SEQ ID NO. 117/SEQ ID NO. 118
(called FEA4 herein), SEQ ID NO. 119/SEQ ID NO. 120
(called FEA7 herein), SEQ ID NO. 121/SEQ ID NO. 122
(called FEA12 herein), SEQ ID NO. 123/SEQ ID NO. 124
(called FEC2 herein), SEQ ID NO. 125/SEQ ID NO. 126
(called FEC4 herein), SEQ ID NO. 127/SEQ ID NO. 128
(called FEC10 herein), SEQ ID NO. 129/SEQ ID NO. 130
(called FED2 herein), SEQ ID NO. 131/SEQ ID NO. 132
(called FED5 herein), SEQ ID NO. 133/SEQ ID NO. 134
(called FED8 herein), SEQ ID NO. 135/SEQ ID NO. 136
(called FEE10 herein), SEQ ID NO. 137/SEQ ID NO. 138
(called FEF8 herein), SEQ ID NO. 139/SEQ ID NO. 140
(called FEH2 herein), SEQ ID NO. 141/SEQ ID NO. 142
(called FEH7 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO.

62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, and combinations thereof.

The present disclosure further provides a method for treating or preventing various cancers or diseases of the heart, bone/joints or lung, wherein such diseases are selected from the group consisting of hepatocellular carcinoma, colon adenocarcinoma, lung carcinoma, breast cancer, myocardial infarction, angina, osteoarthritis, pulmonary fibrosis, asthma, cystic fibrosis, bronchitis, and asthma, comprising administering an anti-OprF and anti-OprI polypeptide, wherein the anti-OprF and anti-OprI polypeptide is selected from the group consisting of a fully human antibody of an IgG class that binds to a OprF and OprI epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and combinations thereof, and that has the light chain variable domain sequence that is at least 95% identical to the amino acid sequence consisting SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, and combinations thereof, and that has the light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO.

62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, and combinations thereof.

Preferably, the method for treating or preventing a disease caused by *Pseudomonas aeruginosa* infections, wherein the disease is selected from the group consisting of burns, surgical site infections, diabetic foot ulcers, infected wounds, and cystic fibrosis.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, $5^{th}$ Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecfic antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634; 6,696,245, US App. Pub. 20/0202512; 2004/0202995; 2004/0038291; 2004/0009507; 2003/0039958, and Ward et al., *Nature* 341: 544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science*

242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-OprF and anti-OprI antibody. In another embodiment, all of the CDRs are derived from a human anti-OprF and anti-OprI antibody. In another embodiment, the CDRs from more than one human anti-OprF and anti-OprI antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-OprF and anti-OprI antibody, and the CDRs from the heavy chain from a third anti-OprF and anti-OprI antibody. Other combinations are possible.

Further, the framework regions may be derived from one of the same anti-OprF and anti-OprI antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody(-ies) from another species or belonging to another antibody class or subclass. Also included are fragments of such antibodies that exhibit the desired biological activity (i.e., the ability to specifically bind OprF and OprI).

A "neutralizing antibody" or an "inhibitory antibody" is an antibody that inhibits the proteolytic activation of OprF and OprI when an excess of the anti-OprF and anti-OprI antibody reduces the amount of activation by at least about 20% using an assay such as those described herein in the Examples. In various embodiments, the antigen binding protein reduces the amount of amount of proteolytic activation of OprF and OprI by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human OprF and OprI) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA.* 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

OprF and OprI-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O (CH$_2$CH$_2$O)$_n$—CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide.

Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Formulations and Modes of Administration

The present disclosure features method for treating or preventing the *S. aureus* infection comprising administering an anti-OprF and anti-OprI polypeptide. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

95% Homology

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)). Near et al. *Mol. Immunol.* 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2).

Exemplary Uses

An OprF and OprI binding polypeptide can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-OprF and anti-OprIantibodies agents of the invention can be used alone.

In certain embodiments, the binding polypeptides of fragments thereof can be labeled or unlabeled for diagnostic purposes. Typically, diagnostic assays entail detecting the formation of a complex resulting from the binding of a binding polypeptide to OprF and OprI. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising an OprF and OprI protein is combined with the subject binding polypeptides, binding occurs between the binding polypeptides and the OprF and OprI protein. In one embodiment, a sample containing cells expressing an OprF and OprI protein (e.g., endothelial cells) is combined with the subject antibodies, and binding occurs between the binding polypeptides and cells bearing an OprF and OprI protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of an OprF and OprI protein in a biological sample can also be prepared. Such kits will include an OprF and OprI binding polypeptide which binds to an OprF and OprI protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

The following terms, unless otherwise indicated, shall be understood to have the following meanings:

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-EGFR antibodies disclosed herein are characterized by their variable domain region sequences in the heavy $V_H$ and light $V_L$ amino acid sequences. The preferred antibody is A6 which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., OprF and OprI) if it binds to the antigen with a dissociation constant of 1 nanomolar or less.

An "antigen binding domain, "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

A "host cell" is a cell that can be used to express a nucleic acid. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28:31) or CHO strain DX-B11, which is deficient in DHFR (Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

Antigen binding proteins (e.g., antibodies, antibody fragments, antibody derivatives, antibody muteins, and antibody variants) are polypeptides that bind to OprF and OprI.

Oligomers that contain one or more antigen binding proteins may be employed as OprF and OprI antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments.

Preferably, the oligomers comprise antigen binding proteins that have OprF and OprI binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing an OprF and OprI binding fragment of an anti-OprF and anti-OprI antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-OprF and OprI antibody fragment or derivative fused to a leucine zipper peptide are expressed in suitable host cells, and the soluble oligomeric anti-OprF and OprI antibody fragments or derivatives that form are recovered from the culture supernatant.

Antigen-binding fragments of antigen binding proteins of the invention may be produced by conventional techniques. Examples of such fragments include, but are not limited to, Fab and F(ab')$_2$ fragments.

The present disclosure provides monoclonal antibodies that bind to OprF and OprI. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 41, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against OprF and OprI can be used, for example, in assays to detect the presence of OprF and OprI polypeptides, either in vitro or in vivo. The antigen binding proteins also may be employed in purifying OprF and OprI proteins by immunoaffinity chromatography. Blocking antigen binding proteins can be used in the methods disclosed herein. Such antigen binding proteins that function as OprF and OprI antagonists may be employed in treating any OprF and OprI-induced condition, including but not limited to various cancers.

Antigen binding proteins may be employed in an in vitro procedure, or administered in vivo to inhibit OprF and OprI-induced biological activity. Disorders caused or exacerbated (directly or indirectly) by the proteolytic activation of OprF and OprI, examples of which are provided herein, thus may be treated. In one embodiment, the present invention provides a therapeutic method comprising in vivo administration of an OprF and OprI blocking antigen binding protein to a mammal in need thereof in an amount effective for reducing an OprF and OprI-induced biological activity.

Antigen binding proteins include fully human monoclonal antibodies that inhibit a biological activity of OprF and OprI.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of OprF and OprI bound thereto. Polypeptides contemplated for use herein include substantially homogeneous recombinant mammalian anti-OprF and anti-OprI antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-OprF and anti-OprI antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSC→CPPC) in the hinge region (Bloom et al., 1997, *Protein Science* 6:407) to alleviate a tendency to form intra-H chain disulfide bonds that can lead to heterogeneity in the IgG4 antibodies.

In particular embodiments, antigen binding proteins of the present invention have a binding affinity ($K_a$) for OprF and OprI of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from OprF and OprI. In one embodiment, the antigen binding protein has a $K_{off}$ of $1 \times 10^{-4}$ to $^{-1}$ or lower. In another embodiment, the $K_{off}$ is $5 \times 10^{-5}$ to $^{-1}$ or lower. In another embodiment, the $K_{off}$ is substantially the same as an antibody described herein. In another embodiment, the antigen binding protein binds to OprF and OprI with substantially the same $K_{off}$ as an antibody described herein.

In another aspect, the present disclosure provides an antigen binding protein that inhibits an activity of OprF and OprI. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of OprF and OprI with substantially the same $IC_{50}$ as an antibody described herein.

In another aspect, the present disclosure provides an antigen binding protein that binds to OprF and OprI expressed on the surface of a cell and, when so bound, inhibits OprF and OprI signaling activity in the cell without causing a significant reduction in the amount of OprF and OprI on the surface of the cell. Any method for determining or estimating the amount of OprF and OprI on the surface and/or in the interior of the cell can be used. In other embodiments, binding of the antigen binding protein to the OprF and OprI-expressing cell causes less than about 75%, 50%, 40%, 30%, 20%, 15%, 10%, 5%, 1%, or 0.1% of the cell-surface OprF and OprI to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of OprF and OprI, or to an epitope of OprF and OprI and an epitope of another molecule, via two different antigen binding sites or regions. Moreover, bispecific antigen binding protein as disclosed herein can comprise an OprF and OprI binding site from one of the herein-described antibodies and a second OprF and OprI binding region from another of the herein-described antibodies, including those described herein by reference to other publications. Alternatively, a bispecific antigen binding protein may comprise an antigen binding site from one of the herein described antibodies and a second antigen binding site from another OprF and OprI antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Preferably, the disclosed antibodies are administered by inhalation, but aerosolization of full IgG antibodies may prove limiting due to their molecular size (~150 kDa). To maximize available commercial aerosolization devices, smaller Fab fragments may be required. In this case, we may also need to generate Fab fragments from the parental IgG molecules. Therefore, we will perform initial studies using standard enzyme-based digestion methodologies for the generation of Fab fragments, which will then be characterized in parallel with full IgG molecules.

Example 1

This example illustrates an ELISA assay that was conducted to check binding of various candidate antibodies. FIGS. 1-4 show the results of the ELISA studies showing the disclosed antibodies that bind to their respective targets.

Example 2

This example illustrates that ELISA plates were coated with 100 μL of wild type *P. aeruginosa* PAO1, ΔoprF, and ΔoprI strains and incubated at 37° C. for two hours. The plates were blocked with PBS plus 10% fetal calf serum and then washed in PBST (PBS+0.05% Tween) for 2 h. The plates were then incubated with specific mAbs to oprF, oprI, *P. aeruginosa* and a non-specific human IgG control antibody at 0.5 μg/ml, 2.5 μg/mL and 5 μg/mL for 1 hr at 37° C. After washing, anti-human secondary antibody (1:10,000 in PBS) was added, followed by further washing. 3,3',5,5'-Tetramethylbenzidine (TMB) was added to each well at RT for 30 minutes, followed by 50 μl of 2N H2SO4. The plates were then read at 450 nm with a Molecular Devices SpectraMax plate reader.

As in many cell-based ELISAs, the data here (FIG. 5) show significant background signal but nonetheless, there were a few clones that demonstrated specificity for the OprF- or OprI-expressing strain over the knockout bacteria. To further investigate these potential binders, Western blots were performed using bacterial cell lysates.

Example 3

This example illustrates Western blots using bacterial cell lysates. Strains were grown as described to an OD600 of ~1.0. Cells were pelleted, suspended in 5×SDS loading buffer and boiled for 5 minutes. Suspensions were then run through a 26-gauge needle to disperse the viscous cell components. Samples were resolved on a 12% SDS-PAGE gel, followed by semi-dry transfer to a nitrocellulose membrane. Blots were probed with primary anti-OprF, anti-OprI, and anti-*P. aeruginosa* antibodies followed by anti-human HRP-conjugated secondary antibody. Blots were visualized using chemiluminescent detection via a BioRad GelDoc XR+ system (FIGS. 6 and 7). The Western blot data confirm that the mAbs oprIA5 and oprFF7 specifically recognize OprI and OprF, respectively. Importantly, both mAbs recognize wild type *P. aeruginosa.*

Example 4

This example illustrates the effects of our antibody on the ability of *P. aeruginosa* to form biofilm or to disperse already formed biofilm. Attachment assays were performed as follows: 5 ml of LBNS was inoculated with a single colony of *P. aeruginosa* PAO1, ΔoprF, and ΔoprI into a culture tube and grown overnight at 37° C. The following morning, 50 μL of the overnight culture was seeded into a new test tube with 5 mls fresh media and grown to OD600 0.5-0.7 at 37° C. 50 μL of the bacterial culture was added to 50 μL of the appropriate concentration of mAb to get a final concentration of either 2.5 μg/mL, 5 μg/mL, or 10 μg/mL, mixed and plated into 96-well PVC microtiter dishes and incubated statically at 37° C. for 2 h. The plates were then washed vigorously by immersion in water. Biomass was stained with 0.1% crystal violet for 30 minutes, followed by vigorous washing. Remaining crystal violet was solubilized in 100 μL of 95% ethanol for 30 minutes and transferred to a fresh 96-well plate. Absorbance was determined at OD540. The data are shown in FIG. 8A.

Example 5

This example illustrates a biofilm disruption assay. Disruption assays were performed as follows: 5 ml of LBNS was inoculated with a single colony of *P. aeruginosa* PAO1, ΔoprF, and ΔoprI into an overnight culture tube and grown at 37° C. The following morning, 50 μl of the overnight culture was seeded into a new test tube with 5 mls fresh media and grown to OD600 0.5-0.7 at 37° C. 100 μl of the bacterial culture was added to a 96-well MBEC peg plate and incubated at 37° C. overnight. The next morning the pegs were washed using another flat bottom 96 well plate with sterile ddH20. 100 μl of mAbs were then added to a new 96 well flat bottom plate and the peg lid (containing the overnight biofilm) was incubated with the mAbs at the above concentrations for two hours at room temperature. Plates were then washed vigorously using another flat bottom 96 well plate with sterile ddH20. Biomass was stained with 0.1% crystal violet for 30 minutes, followed by vigorous washing. Remaining crystal violet was solubilized in 100 μl of 95% ethanol for 30 minutes and transferred to a fresh 96-well plate and absorbance was measured at OD540.

The biofilm assays suggest that neither mAb has a profound effect on biofilm formation nor established biofilm. However, it appears that higher concentration of oprFF7 might disrupt existing biofilm to a moderate extent.

Sequence Listing
OprF-binding Antibodies

| | Heavy chain variable domain region | Light chain variable domain region |
|---|---|---|
| OFA1 | EVQLVQSGAEMKKPGSSVKVSCKAS GDTFSNYNFNWVRQAPGQGLEWMG GITPIFGAAQYAQKFQDRVTIIADE STSTAYMELRSLRSDDTAVYYCAGG WAGFCSSASCYRFDYWGQGTTVTVSS SEQ ID NO. 1 | SYELTQPPSVSAAPGQKVTISCS GSSSNIGNYYVSWYQQLPGTAP KLLIYDNDKRPSGIPDRFSASKS GTSASLAITGLQAEDEADYYCQ SYDRTLSGGILGTGTKLTVL SEQ ID NO. 2 |
| OFC7 | QVQLVVSGDEVKKPGASVKVSCKAS GYTFTSYDINWVRQAPGQGLEWLGW MSPNSGNTDYAEKFQGRVTMTRDTSI TTAYMELSSLASEDTAVYYCARGVAA GLDYWGQGTLVTVSS SEQ ID NO. 3 | LPVLTQSASVSGSPGQSITISCT GTSTDVDYSNYVSWYQHHPGK APKLMIYDVSRRPSGVSNRFSG SKSGNTASLTISGLQAEDEADYY CSSYTSGTTLVFGGGTKVTVL SEQ ID NO. 4 |
| OFC10 | EVQLVESGPGLAKPSETLSLTCSVFG GSIRRYYWSWIRQSPGKGLEWIGFFY HSGSADYNPSPNYNPSFKSRVTISVD TSKTQFSLKMTSVTAADTAVYYCAKG DGSWYLDSWGQGTLVTVSS SEQ ID NO. 5 | DIVMTQSPSSLSASVGDRVTITC RASHSISRSLNWYQQKPGKAPK LLIYAASILQSGVSSRFSGSGSG TDFTLTISRLQPEDFATYYCQES DSPPPFTFGPGTKVEIK SEQ ID NO. 6 |
| OFF7 | EVQLVQSGAEMKKPGSSVKVSCKAS GDTFSNYNFNWVRQAPGQGLEWMG GITPIFGAAQYAQKFQDRVTIIADE TSTSAYMELRSLRSDDTAVYYCAGG WAGFCSSASCYRFDYWGQGTTVTVSS SEQ ID NO. 7 | SYELTQPPSVSAAPGQKVTISCS GSSSNIGNYYVSWYQQLPGTAP KLLIYDNDKRPSGIPDRFSASKS GTSASLAITGLQAEDEADYYCQ SYDRTLSGGILGTGTKLTVL SEQ ID NO. 8 |
| OFF8 | QVQLVQSGAEVKKPGASVRVSCKAS EYTFTAYYLHWVRQAPGQGLEWMGR IDPNSGGTNFAQKFQGRVTMTSDTSV STAYMELRGLRSDDTAVYYCARAQYA AKDYWGQGTLVTVSS SEQ ID NO. 9 | SYELMQPPSVSVAPGKTARITC GGNNIGSKSVHWYQQKPGQAP VLVVYDDSDRPSGIPERFSGSN SGNTATLTISRVEAGDEADYYC QVWDSSSAHVVFGGGTKLTVL SEQ ID NO. 10 |
| OFG5 | QVQLVQSGAEVKKPGASVKVSCKAS GYTFTGYYMHWVRQAPGQGLEWMG WINPNSGGTNYAQKFQGRVTITRDTS ASTAYMELSSLRSEDTAVYYCATLGG AAAGLNTDYWGQGTLVTVSS SEQ ID NO. 11 | SYELMQPASVSGSPGQSITISCT GTSSDVGGYNYVSWYQQHPGK APKLMIYDVSNRPSGVSNRFSG SKSGNTASLTISGLQAEDEADYY CSSYTSSSTRVFGTGTKVTVL SEQ ID NO. 12 |
| OFH10 | QVQLVESGGGLIQPGGSLRLSCAASG FTVSSNYMSWVRQAPGKGLEWVSVI YSGGTKYYADSVKGRFTISRDNSKNT LYLQMNSLRAEDTAVYFCARGDDAFD IWGQGTMVTVSS SEQ ID NO. 13 | QSVLTQPASVSGSPGQSITISCT GTSSDVGGYNYVSWYQQHPGK APKLMIYDVSNRPSGVSNRFSG SKSGNTASLTISGLQAEDEADYY CSSYTSSNTIVFGSGTKVTVL SEQ ID NO. 14 |

Sequence Listing
OprI-binding Antibodies

| | Heavy chain variable domain region | Light chain variable domain region |
|---|---|---|
| OIA1 | EVQLVESGGGLVQPGGSLRLSCAAS GFTGSNNYMSWVRQAPGKGLEWVSII YSGGNAYYADSVKGRFTISRDNSKNIL YFQMNSLRVEDTAVYYCAEGYGGVD YWGQGTLVTVSS SEQ ID NO. 15 | DVVMTQSPDSLAVSLGERATIN CKSSQSVLYSSNNKNYLAWYQ QKPGQPPKLLIYWASTRESGVP DRFSGSGSGTDFTLTISSLQAED VAVYYCQQYYSSPFSFGPGTKV DIK SEQ ID NO. 16 |

Sequence Listing
OprI-binding Antibodies

| | Heavy chain variable domain region region | Light chain variable domain region |
|---|---|---|
| OIA10 | QVQLVQSGAEVKKPGASVKVSCKAS GYTFTSYYMHWVRQAPGQGLEWMGI INPSGGSTSYAQKFQGRVTMTRDTST STVYMELSSLRAEDMAVYYCAREGLP DAFDIWGQGTMVTVSS SEQ ID NO. 17 | QAGLTQPASVSGSPGQSITLSC TGTSSDVGGYNYVTWFQQHPG KAPKLMIYDVSKRPSGASNRFS GSKSGNTASLTISGLQAEDEAD YYCSSYTSSGTYVFGTGTKLTVL SEQ ID NO. 18 |
| OIA2 | QVQLVQSGAEVKKPGASVKVSCKAS GYTFTGYYMHWVRQAPGQGLEWMG WINPNSGGTNYAQKFQGRVTMTRNT SISTAYMELSSLRSEDTAVYYCAREIY DFDAFDIWGQGTMVTVSS SEQ ID NO. 19 | SYELMQPPSVSVAPGKTARITC GGNNIGSKSVHWYQQKPGQAP VLVIYYDSDRPSGIPERFSGSNS GNTATLTISRVEAGDEADYYCQ VWDSRSDQVIFGGGTQLTVL SEQ ID NO. 20 |
| OIA4 | QVQLVESGGGLVQPGGSLRLSCAAS GFTVSSNYMSWVRQAPGKGLEWVSV IYSGGSTYYADSVKGRFTISRDNSKNT LYLQMNSLRAEDTAVYYCAREDSSSW YWNAFDIWGQGTMVTVSS SEQ ID NO. 21 | YELMQPPSVSVAPGKTARITCG GNNIGSKSVHWYQQKPGQAPV LVIYYDSDRPSGIPERFSGSNSG NTATLTISRVEAGDEADYYCQV WDSSSDHPVFGGGTKLTVL SEQ ID NO. 22 |
| OIA5 | QVQLVQSGSELKKPGASVKVSCKASG YTFTSYAMNWVRQAPGQGLEWMGII NPSGGSTSYAQKFQGRVTMTRDTST STVYMELSSLRSEDTAVYYCARSTLW FSEFDYWGQGTLVTVSS SEQ ID NO. 23 | EIVLTQSPGTLSLSPGERATLSC RASQSVTIYLAWYQQKPGQAPR LLIYDASNRAAGIPARFSGSGSG TDFTLTISSLEPEDFATYYCQQY DTSSTFGQGTKVDIK SEQ ID NO. 24 |
| OIA6 | EVQLLESGGGLVQPGGSLRLSCAASG FTFSSYEMNWVRQAPGKGLEWVSYIS SSGSTIYYADSVKGRFTISRDNAKNSL YLQMNSLRAEDTAVYYCARLIYDSSG YYFDYWGQGTLVTVSS SEQ ID NO. 25 | DIQLTQSPLSLPVTLGQPASISC RSSQSLVHSDGNTYLNWFQQR PGQSPRRLIYKVSNRDSGVPDR FSGSGSGTDFTLKISRVEAEDV GVYYCMQGSHWPHTFGQGTKL EIK SEQ ID NO. 26 |
| OIA7 | QVQLVQSGAEVKKPGASVKVSCKAS GYTFTSYYMHWVRQAPGQGLEWMGI INPSGGSTSYAQKFQGRVTMTDTSA NTVYMELSRLRSDDTAVYYCARDWFS EDYFDYWGQGTLVTVSS SEQ ID NO. 27 | QSVVTQPPSVSAAPGQKVTISC SGSNSNIGNNYVSWYQQLPGTA PKLLIYDNNKRPSGIPDRFSGSK SGTSATLAITGLQTGDEADYYC GTWDSSLSGGVFGGGTKLTVL SEQ ID NO. 28 |
| OIA8 | EVQLVQSGGGVVQPGRSLRLSCAAS GFTFSIYGMHWVRQAPGKGLEWVAVI WDDGSKKYYADSVKGRFTISRDNSKN TLYLQMNTLRADDTAVYYCAGELWKY YDSSGFYSINPEYFQHWGQGTLVTVS S SEQ ID NO. 29 | QAGLTQPASVSGSPGQSITISCT GTSSDVGGYNYVSWYQQHPGK APKLIIYDVSERPSGVSNRFSGS KSGNTASLTISGLQAEDEADYYC SSYTTSSTLLFGGGTKLTVL SEQ ID NO. 30 |
| OIA9 | EVQLVQSGGGLIQPGGSLRLSCAASG FSVSSDYMSWVRQAPGKGLEWVSVI YTGGTTYYADSVKGRFTISRDNSKNTL YLQMNSLRAEDTAVYYCARDYGDSFD YWGQGTLVTVSS SEQ ID NO. 31 | QAGLTQPASVSGSPGQSITISCT GTSSDVGGYNYVSWYQQHPGK APKLMIYDVSNRPSGVSNRFSG SKSGNTASLTISGLQAEDEADYY CSSYTKSNTLVFGGGTKVTVL SEQ ID NO. 32 |
| OIB1 | QVQLVQSGGGVVQPGRSLRLSCAAS GFTVSSNYMSWVRQAPGKGLEWVSV IYSGGSTYADSVKGRFTISRDNSKNT LYLQMNSLRAEDTAVYYCARDWGYD KGDWGQGTLVTVSS SEQ ID NO. 33 | LPVLTQPPSLSVAPGKTARITCG GNNIDSTGVHWYQQKAGQAPV LVVYDDSDRPSGIPERFSGSNS GNTATLTISRVEAGDEADYYCQ VWDSSSDHVVFGGGTKLTVL SEQ ID NO. 34 |
| OIB11 | QVQLVQSGGGLIQPGGSLRLSCAASG FTVSSNYMSWVRQAPGKGLEWVSVI YSGGSTYYADSVKGRFTISRDNSKNT LYLQMNSLRAEDTAVYYCARDYGDYF DYWGQGTLVTVSS SEQ ID NO. 35 | SYELMQPPSASGTPGQRVTISC SGSSSNIGSNYVDWYQQLPGTA PKLLIYSNNERPSGVPDRFSGSK SGTSASLAISGLRSEDEADYYCA AWDDSLSGYVFGTGTKVTVL SEQ ID NO. 36 |
| OIB12 | QVQLVQSGAEVKKPGASVKVSCKAS GYTFTSYYMHWVRQAPGQGLEWMGI INPSGGSTSYAQKFQGRVTMTRDTST | QPVLTQPPSVSVAPGAAARITC GGNNIGSQIVHWYRQKPGQAPV LVLYYDTERPSGIPERFSGSNSG |

Sequence Listing
OprI-binding Antibodies

| | Heavy chain variable domain region region | Light chain variable domain region |
|---|---|---|
| | STVYMELSSLRSEDTAVYYCASSPGA YSSGWYDYWGQGTLVTVSS SEQ ID NO. 37 | NTATLTVSRVEAGDEADYFCQV WDLSHDHPGWLFGGGTKLTVL SEQ ID NO. 38 |
| OIB2 | QVQLVESGGGLIQPGGSLRLSCAASG FTVSSNYMSWVRQAPGKGLEWVSVI YSGGSTYYADSVKGRFTISRDNSKNT LYLQMNSLRAEDTAVYYCAREGGEHF DYWGQGTLVTVSS SEQ ID NO. 39 | QAVLTQPASVSGSPGQSITISCT GTSSDVGGYNYVSWYQQHPGK APKLMIYDVSKRPSGVSNRFSG SKSGNTASLTISGLQAEDEGDY YCFSYTSSSTLVFGGGTKLTVL SEQ ID NO. 40 |
| OIB3 | EVQLVESGAEVKKPGASVKVSCKASG YTFTSYGISWVRQAPGQGLEWMGWI SAYNGNTNYAQKLQGRVTMTTDTSTS TAYMELRSLRSDDTAVYYCARDYYYG SGTANDYYYYGMDVWGQGTTVTVSS SEQ ID NO. 41 | LPVLTQPPSASGTPGQRVTISCS GSSSNIGNNPVNWYQQVPGTA PKLLIHSSNQRPSGVPDRFSGS KSGASASLAISGLQSEDEADYY CAAWDDILNGLVFGGGTKLTVL SEQ ID NO. 42 |
| OIB8 | QVQLVQSGGGLVQPGESLRLSCAAS GFTVSSNHMAWVRQAPGKGLEWVSL IYNGDSTYYPDSVKGRFTISRDNSKNA LYLQMNSLRAEDTAVYYCARDWGYD TADWGQGTLVTVSS SEQ ID NO. 43 | QPVLTQPASVSGSPGQSITISCT GTSSDVGAYNYVSWYQQHPGK APKLMIYDVSNRPSGVSNRFSG SKSGNTASLTISGLQAEDEADYY CSSYTSNSTLYVFGTGKVTVL SEQ ID NO. 44 |
| OIB9 | QVQLVQSGAEVKKPGASVKVSCKAS GDTFTGQYMNWVRQAPGQGLEWMG WINPNSGFTNYAQKFQGRVTMTWDT SISTAYMELSRLRSDDTAVYYCARDS WDYYSYYGMDVWGQGTTVTVSS SEQ ID NO. 45 | DIQLTQSPSFLSASVGDRVTITC RASQDITSYLAWYQQKPGKAPK LLVYAASTLQSGVPSRFSGSGS GTDFTLTISSLQPEDFATYYCQQ SYGTPYTFGQGTKLEIK SEQ ID NO. 46 |
| OIC1 | EVQLVESGGGLVQPGGSLRLSCAAS GFTGSNNYMSWVRQAPGKGLEWVSII YSGGNAYYADSVKGRFTISRDNSKNIL YFQMNSLRVEDTAVYYCAEGYGGVD YWGQGTLVTVSS SEQ ID NO. 47 | QAGLTQPASVSGSPGQSITISCT GTSSDIGAYNFVSWYQQHAGK GPKLLIYDVTNRPSGVSDRFSG SKSGNTASLTISGLQADDEADYF CASYTATTTLGYVFGTGTKLTVL SEQ ID NO. 48 |
| OIC3 | EVQLVQSGGGLVQPGGSLRLSCAAS GFTVNSNHMSWVRQAPGKGLEWVSL IYNGDNTYYADSVKGRFTISRDNPKNT LYLQMNRLRDEDTAVYYCARDWGYN VGDWGQGTLVTVSS SEQ ID NO. 49 | LPVLTQPRSVSGSPGQSVTISCT GTSSDVGFYNYVSWYQQHPGK APKLLIYDVTKRPSGVPDRFSGS KSGNTASLTISGLQAEDDADYY CSSYGGSNNFVIFGGGTKVTVL SEQ ID NO. 50 |
| OI06 | QVQLVESGGGLVQPGGSLRLSCAAST FTFSRYPMTWVRQAPGKGLEWVSSIS GGGDTTYYADSVKGRFAIARDNSKNT VSLEMISLRAEDTAVYYCAKDWLYRG GPWGQGTLVTVSS SEQ ID NO. 51 | QPVLTQPASVSGSPGQPITISCT GTSSDVGGYNHVSWYQQYPGE APKVMIFDVSKRPSGVSNRFSG SKSGNTASLTISGLQADDEADYY CNSLTSSGYVFGTGTKVTVL SEQ ID NO. 52 |
| OIC9 | QVQLVQSGAEVKKPGASVKVSCKAS GYTFTSYGISWVRQAPGQGLEWMGW ISAYNGNTNYAQKLQGRVTMTTDTST STAYMELRSLRSDDTAVYYCARDWG ENEYWGQGTLVTVSS SEQ ID NO. 53 | QPVLTQPASVSGSPGQSITISCT GTSSDIGGYNYVSWYQQHPDK APKLMIYDVSSRPSGVSNRFSG SKSGSTASLTISGLQPEDEADYY CISYTNSNIFGGYVFGTGTKLTV L SEQ ID NO. 54 |
| OID1 | QVQLVQSGAEVKKPGASVKVSCKTS GYTFTGYYMHWLRQVPGQGFEWMG WISPKTGDTNSPQTFHGRVTMTIDTSI NTAYMEMNRLRSDDTAVYYCAREALI EDAFDIWGQGTMVTVSS SEQ ID NO. 55 | QSVLTQPPSVSGAPGQRVTISC TGSSSNIGAAYDVHWYQQLPGT APKLLIYRNSNRPSGVPDRFSG SKSGTSASLAISGLRSEDEADYY CAAWDDSLSDVVFGGGTKLTVL SEQ ID NO. 56 |
| OID10 | EVQLVQSGGGLIQPGGSLRLSCAASG FLVSSKYMSWVRQAPGKGLEWVSVIY TDGSTYYADSVKGRFTISRDNSKNAL YLQMNSLRAEDTAVYYCARDWGYDT ADWGQGTLVTVSS SEQ ID NO. 57 | QSVVTQPPSVSAAPGQKISISCS GSSSNVGNNYVSWYQQLPGTA PKLLIFDNNKRPSGIPDRFSGSK SGTSATLGISGLQTGDEADYYC GTWDTSLRALVFGGGTKLTVL SEQ ID NO. 58 |

Sequence Listing
OprI-binding Antibodies

| | Heavy chain variable domain region region | Light chain variable domain region |
|---|---|---|
| OID12 | EVQLLESGGGLVQPGRSLRLSCTASG FTFGDYAMSWFRQAPGKGLEWVSVI YSGGSTYYADSVKGRFTISRHNSKNT LYLQMNSLRAEDTAVYYCARGYGIDY WGQGTLVTVSS SEQ ID NO. 59 | QSVVTQPPSVSAAPGQRVTISC SGSSSNIENNYVSWYQQLPGTA PKLLIYDNNKRPSGIPDRFSGSK SGTSATLGITGLQTGDEADYYC GTWDSSLSTEVFGGGTKLTVL SEQ ID NO. 60 |
| OID3 | EVQLVQSGGGLVQPGGSLRLSCAAS GFTVSSNHMAWVRQAPGKGLEWVSL IYNGDSTYYPDSVKGRFTISRDNSKNA LYLQMNSLRAEDTAVYYCARDWGYD TADWGQGTLVTVSS SEQ ID NO. 61 | QSVLTQPASVSGSPGQSITISCT GTSSDVGGYNYVSWYQQHPGK APKLMIYDVTNRPSGVSNRFSG SKSGNAASLTISGLQAEDEADYY CSSYTGSSTLVFGGGTKVTVL SEQ ID NO. 62 |
| OID4 | QVQLVQSGAEVKKPGASVKVSCKAS GYTFTSYYMHWVRQAPGQGLEWMGI INPSGGSTSYAQKFQGRVTMTRDTST STVYMELSSLRSEDTAVYYCARDRLY GDYFDYWGQGTLVTVSS SEQ ID NO. 63 | QSVVTQPPSVSAAPGQKVTISC SGSSSNIGNNYVSWYQQLPGTA PKLLIYDNNKRPSGIPDRFSASK SGTSASLAISGLRSEDEADYYCA AWDDSLSGNWVFGGGTKLTVL SEQ ID NO. 64 |
| OID5 | QVQLVESGGGLIQPGGSLRLSCAASG FTVSSNYMSWVRQAPGKGLEWVSVI YSGGSTYYADSVKGRFTISRDNSKNT LYLQMNSLRAEDTAVYYCASGYGDYE DYWGQGTLVTVSS SEQ ID NO. 65 | QSVLTQPPSASGSPGQSVTISC TGTSRDVGGYNYVSWYQQHPG KAPKLMIYDVSKRPSGVSNRFS ASKSGNTASLTISALQAEDEADY YCTSYTGSSP PYVFGTGTKVTV L SEQ ID NO. 66 |
| OID6 | EVQLVESGGGLIQPGGSLRLSCAASG FTVSSNYMSWVRQAPGKGLEWVSVI YSGGSTYYADSVKGRFTISRDNSKNT LYLQMNSLRAEDTAVYYCASGYGDYE DYWGQGTLVTVSS SEQ ID NO. 67 | QSVLTQPASVSGSPGQSITISCT GTSSDVGGYNYVSWYQQHPGK APKLMIYDVTKWPSGASNRFSG SKSGNTASLTISGLQAEDEADYY CSSYTSRTYVYGTGTKVTVL SEQ ID NO. 68 |
| OID8 | QVQLVQSGAEVKKPGSSVKVSCKAS GGTFSSYAISWVRQAPGQGLEWMGE IIPIFGTTNYAQKFQGRVTIIADESTSTA YMELSSLRPDDTAVYYCASASSWYE WYFDVWGRGTLVTVSS SEQ ID NO. 69 | QSVLTQPRSVSGSPGQSVTISC TGTSSDVGGYNYVSWYQQHPG KAPKLMIYDVGKRPSGVPDRFS GSKSGNTASLTISGLQAEDEAD YYCSSYTSSGTQVFGTGTKLTV L SEQ ID NO. 70 |
| OIE12 | EVQLLESGGGLVQPGRSLRLSCTASG FTFGDYAMSWFRQAPGKGLEWVSVI YSGGSTYYADSVKGRFTISRHNSKNT LYLQMNSLRAEDTAVYYCARGYGIDY WGQGTLVTVSS SEQ ID NO. 71 | QSVVTQPPSVSAAPGQRVTISC SGSSSNIENNYVSWYQQLPGTA PKLLIYDNNKRPSGIPDRFSGSK SGTSATLGITGLQTGDEADYYC GTWDSSLSTEVFGGGTKLTVL SEQ ID NO. 72 |
| OIE3 | QVQLVESGGGLVKPGGSLRLSCAAS GFKFSDNYMTWVRQAPGKGLEWVSY ISGSGKTTHFADSVRGRFTISRDNAKN SVDLQMNSLRVEDTAMYYCARWEVG VDAFDIWGQGTMVTVSS SEQ ID NO. 73 | LLVLTQSPSVSVAPGKTARITCG GNNIGSKSVHWYQQKPGQAPV LVVYDDSDRPSGIPERFSGSNS GNTATLTISRVEAGDEADYYCQ VWDSSSDHPVFGGGTKLTVL SEQ ID NO. 74 |
| OIE9 | QVQLQQWGAGLLKPSETLSLTCAVYG GPFRSYYWSWIRQPPGKGLEWIGEIN HSGSTNYNPSLKSRVTISVDRSKNQF SLKLTSVTAADTAVYYCAREGDHEAF DIWGQGTMVTVSS SEQ ID NO. 75 | QPVLTQPPSVSAAPGQKVTISC SGSSSNIGNNYVSWYQQLPGTA PKLLIYDNNKRPSGIPDRFSGSK SGTSATLGITGLQTGDEADYYC GTWDSSLSSLVFGGGTKLTVL SEQ ID NO. 76 |
| OIF10 | QVQLVQSGGGLVQPGGSLRLSCAAS GFTVNSNHMSWVRQAPGKGLEWVSL IYNGDNTYYADSVKGRFTISRDNPKNT LYLQMNRLRDEDTAVYYCARDWGYN VGDWGQGTLVTVSS SEQ ID NO. 77 | QSVLTQPASVSGSPGQSITISCT GTSSDVGGYNYVSWYQQHPGK APKLMIYDVSNRPSGVSNRFSG SKSGNTASLTISGLQAEDEADYY CSSYAGSNNPYVFGTGTKVTVL SEQ ID NO. 78 |
| OIF4 | EVQLVESGGGLVKPGGSLRLSCAASG FTFSSYRMNWVRQAPGKGLEWVSSI | DIVMTQSPDSLAVSLGERATINC KSSQSLLYNSDNKNYLAWYQQK |

Sequence Listing
OprI-binding Antibodies

| | Heavy chain variable domain region region | Light chain variable domain region |
|---|---|---|
| | SSDSSDFYYADSVKGRFTISRDNAINS LYLQMNSLRAEDTAVYYCARDWGYD KGDWGQGTLVTVSS SEQ ID NO. 79 | PGQPPKLLIYWASTRGSGVPDR FSGSGSGTDFTLSISSLQAEDVA VYYCQQYYSTPYTFGQGTKVEI K SEQ ID NO. 80 |
| OIF6 | QVQLQQWGAGLLKPSETLSLTCAVYG GSFSGYYWSWIRQTPGKGLEWIGEIN HSGSTNYNPSLKSRVTISADTSRNQF SLRLSSVTAADTAVYYCARGDSGFGV VSSYYFDQWGQGTLVTVSS SEQ ID NO. 81 | SYELMQPPSESVAPGQTAKITC GGENIGSKSVHWYQQKSGQAP LLVVYDDRDRPSGIPERFFGSN SGDTASLTISGVEAGDEADYYC QVWDSRNDRVVFGGGTKLTVL SEQ ID NO. 82 |
| OIF9 | QVQLVESGAEVKKPGASVKVSCKASG YTFTSYGISWVRQAPGQGLEWMGWI SAYNGNTNYAQKLQGRVTMTTDTSTS TAYMELRSLRSDDTAVYYCARELGLD AFDIWGQGTMVTVSS SEQ ID NO. 83 | QSVVTQPPSVSAAPGQKVTISC SGSSSNIGNNYVSWYQQLPGTA PKLLIYDNNKRPSGIPDRFSGSK SGTSATLGITGLQTGDEADYYC GTWDSSLSAVVFGGGTKLTVL SEQ ID NO. 84 |
| OIG1 | EVQLVESGAEVKKPGSSVKVSCKASG YTFTNYDINWVRQATGQGLEWMGW MNPNSGNTGYAQKFQGRVTMTRDTS ISTAYMELSSLKSEDTAVYYCARDDYY DFDSWGQGTLVTVSS SEQ ID NO. 85 | QSVVTQPPSVSAAPGQKVTISC SGSSSNIGKNYVSWYQHPGTA PKLLIYDNDERPSGIPDRFSGSK SGTSATLGITGLQTGDEADYYC GAWDISLSAWVFGGGTKLTVL SEQ ID NO. 86 |
| OIG11 | QVQLVQSGGGLLQPGGSLRLSCAAS GFTFSNYDMHWVRQPPGKGLEWVSS IDTAGDTYYEGSAKGRFTISRDNSANT LYLQMNSLTTEDTAVYYCAKDRIWFG DFDYWGQGTLVTVSS SEQ ID NO. 87 | QAVLTQPASVSGSPGQSITISCT GTSSDVGGYNYVSWYQQHPGK APKLMIYDVSKRPSGVSNRFSG SKSGNTASLTISGLQAEDEADYY CSSYTSSSTLYVFGTGTKLTVL SEQ ID NO. 88 |
| OIG12 | QVQLVQSGGGLVQPGGSLRLSCAAS GFTFSSYEMNWVRQAPGKGLEWVSY ISSSGSTIYYADSVKGRFTISRDNAKN SLYLQMNSLRAEDTAVYYCAREGQLL WAPFDYWGQGTLVTVSS SEQ ID NO. 89 | QAVLTQP PSVSGAPGQRVTISC TGSNSNIGAGYDVHWYQQLPGT APKLLIYGNTNRPSGVPDRFSG SKSGTSASLAITGLQAEDEADYY CQSYDSRLSAVFGGGTKVTVL SEQ ID NO. 90 |
| OIG2 | QVQLVQSGGGLVQPGGSLRLSCAAS GFTVNSNHMSWVRQAPGKGLEWVSL IYNGDNTYYADSVKGRFTISRDNPKNT LYLQMNRLRDEDTAVYYCARDWGYN VGDWGQGTMVTVSS SEQ ID NO. 91 | QSALTQPASVSGSPGQSITISCT GTSSDVGGYNYVSWYQQHPGK APKLMIYDVSKRPSGVSNRFSG SKSGNTASLTISGLQAEDEADYY CSSYTSSSTPHYVFGTGTKVTV L SEQ ID NO. 92 |
| OIG5 | QMQLVQSGAEVKKPGASVKVSCKAS GYTFTSYYMHWVRQAPGQGLEWMGI INPSGGSTSYAQKFQGRVTMTRDTST STVYMELNSLRSEDTAVYYCAREYLD YFDYWGQGTLVTVSS SEQ ID NO. 93 | QAGLTQPASVSGSPGQSITISCT GTSSDVGGYNYVSWYQQHPGK APKLMIYDVSNRPSGVSNRFSG SKSGNTASLTISGLQAEDEADYY CSSYTSSSTLRYVFGTGTKLTVL SEQ ID NO. 94 |
| OIG7 | QVQLVESGGGLVQPGGSLRLSCAAS GFTFSSYEMNWVRQAPGKGLEWVSY ISSSGSTIYYADSVKGRFTISRDNAKN SLYLQMNSLRAEDTAVYYCARVQQW PDDAFDIWGQGTTVTVSS SEQ ID NO. 95 | QSVLTQPPSASGAPGQRVTISC SGSSSNIGSDTLDWYQQLPGTA PKLLIYSNNQRPSGVPDRFSGS KSGTSASLAISGLQSEDEANYYC AAWDASLNGWVFGGGTKLTVL SEQ ID NO. 96 |
| OIG8 | QITLKESGGGVVRPGGSLRLSCAASG FTFDDYGMSWVRQAPGKGLEWVSSF GSSARNIYYADSVKGRFSISRDNAKNS LYLQVNSLRDEDTAVYYCARGAYYMD VWGNGTTVTVSS SEQ ID NO. 97 | AIRMTQSPSSLSASVGDRVTITC QASQDISNYLNWYQQKPGKAPK LLIYDASNLETGVPSRFSGSGSG TDFTLTISSLQPEDFATYYCLQH NSYPRTFGQGTKVEIK SEQ ID NO. 98 |

Sequence Listing
OprI-binding Antibodies

| | Heavy chain variable domain region region | Light chain variable domain region |
|---|---|---|
| OIG9 | QVQLVESGAEVKKPGASVKVSCKASG YTFTSYGISWVRQAPGQGLEWMGWI SAYNGNTNYAQKLQGRVTMTTDTSTS TAYMELRSLRSDDTAVYYCARDLWDT DAFDIWGQGTMVTVSS<br>SEQ ID NO. 99 | QAVLTQPPSVSAAPGQKVTISC SGSSSNIGNNYVSWYQQLPGTA PKLLIYDNNKRPSGIPDRFSGSK SGTSATLGITGLQTGDEADYYC GTWDSSLSAYVFGTGTKVTVL<br>SEQ ID NO. 100 |
| OIH10 | EVQLVESGGGLVQPGGSLRLSCAAS GFTGSNNYMSWVRQAPGKGLEWVSII YSGGNAYYADSVKGRFTISRDNSKNIL YFQMNSLRVEDTAVYYCAEGYGGVD YWGQGTLVTVSS<br>SEQ ID NO. 101 | QSVVTQPPSVSAAPGQKVTISC SGSSSNIGSNSVSWFQHLPGTA PKLLIYDNNQRPSNIPDRFSGSK SGASATLGITGLQTGDEADYYC GTWDHRLNTYVFGTGTKVTVL<br>SEQ ID NO. 102 |
| OIH11 | EVQLVQSGGGLVQPGGSLRLSCAAS GFTVSSNHMAWVRQAPGKGLEWVSL IYNGDSTYYPDSVKGRFTISRDNSKNA LYLQMNSLRAEDTAVYYCARDWGYD TADWGQGTLVTVSS<br>SEQ ID NO. 103 | SYELMQPPSASGTPGQRVTISC SGSSSNIGSNTVNWYQQLPGTA PKLLIYSYDQRPSGVPDRFSGS KSGTSASLAISGLQSEDEADYYC AAWDDSLNGYVFGTGTKVTVL<br>SEQ ID NO. 104 |
| OIH12 | QVQLVQSGAEVKKPGASVKVSCKAS GYTFTSYYMHWVRQAPGQGLEWMGI INPSGGSTSYAQKFQGRVTMTRDTST STVYMELSSLRSEDTAVYYCAREYLD YFDYWGQGTLVTVSS<br>SEQ ID NO. 105 | QSVVTQPASVSGSPGQSITISCT GTSSDVGGYNYVSWYQQHPGK APKLMIYDVSKRPSGVSNRFSG SKSGNTASLTISGLQAEDEADYY CSSYTSSSTYVFGTGTKVTVL<br>SEQ ID NO. 106 |
| OIH3 | QVQLVQSGGGLVQPGGSLRLSCAAS GFTVSSNHMAWVRQAPGKGLEWVSL IYNGDSTYYPDSVKGRFTISRDNSKNA LYLQMNSLRAEDTAVYYCARDWGYD TADWGQGTLVTVSS<br>SEQ ID NO. 107 | QPVLTQPASVSGSPGQSIAISCS GTSSDIGTYDSVSWYQQHPGKA PKVIIYEVDKRPSGVPDRFSGSK SGNTASLTVSGLQAEDEADYYC SSYAGSNNFVFGTGTKLTVL<br>SEQ ID NO. 108 |
| OIH5 | QVQLVQSGGGLVQPGGSLRLSCAAS GFTVNSNHMSWVRQAPGKGLEWVSL IYNGDNTYYADSVKGRFTISRDNPKNT LYLQMNRLRDEDTAVYYCARDWGYN VGDWGQGTLVTVSS<br>SEQ ID NO. 109 | QSVLTQPPSASGTPGQRVTISC SGSNSNIGTNTVNWYQQVPGTA PKLLIHGNDQRPSGVPDRFSGS KSDTSASLAITGLQSDDDADYYC SAWDDSLNADVFGGGTKLTVL<br>SEQ ID NO. 110 |
| OIH6 | EVQLVQSGAEVKKPGASVKVSCKASG YTFTGYYMHWVRQAPGQGLEWMGW INPNSGGTNYAQKFQGRVTMTRDTSI STAYMELSRLSDDTAVYYCVRSGSY SDFDYWGQGTLVTVSS<br>SEQ ID NO. 111 | SYELMQPPSVSAPGQTARITC GGNNIGSKSVHWYQQKPGQAPI LVIYYDDDRPSGIPERFSGSKSG NTATLTISGVEAGDEADYYCQV WDSYTHVVFGGGTKLTVL<br>SEQ ID NO. 112 |

Sequence Listing
OprF (epitope 8)-binding Antibodies

| | Heavy chain variable domain region | Light chain variable domain region |
|---|---|---|
| FEA2 | EVQLVESGGGLVQPGGSLRLSCAGS GFTFSSYDMNWVRQAPGKGLEWISYI SSSGSAIFYADSVKGRFTISRDNAGNS VYLQMNSLRAEDTAIYYCARRFDYWG QGTLVTVSS<br>SEQ ID NO. 113 | DIVMTQTPLSLPVTLGQPASISC RSSQSLVHSDGNTYLNWLQQR PGQSPRRLIYKVSNRDSGVPDR FSGSGSGTDFTLNITRVETDDVG IYYCMQGTHWPPFTFGPGTKVD IK<br>SEQ ID NO. 114 |
| FEA3 | QVQLVESGGGVFQPGRSLRLSCSTS GFTFSSYDMNWVRQAPGKGLEWLSY ISSSGSAMFYADSVKGRFTISRDTAKN SLYLQMNSLRDEDTAVYYCARQFDQ WGQGTLVTVSS<br>SEQ ID NO. 115 | DIVMTQSPLSLPVALGQPASISC RSSQSLVHSDGNTYLNWFQQR PGQSPRRLIYKVSHRDSGVPDR FSGSGSGTDFTLTISRVEAEDLG IYYCAQGTHWPPFTFGQGTKLEI K<br>SEQ ID NO. 116 |

Sequence Listing
OprF (epitope 8)-binding Antibodies

| | Heavy chain variable domain region | Light chain variable domain region |
|---|---|---|
| FEA4 | QVQLVQSGGGVVQPGRSLRLSCAAS<br>GFTFSSYGMHWVRQAPGKGLEWVAV<br>ISYDGSNKYYADSVKGRFTISRDNSKN<br>TLYLQMNSLRAEDTAVYYCARDGRFL<br>PYPGGMDVWGQGTTVTVSS<br>SEQ ID NO. 117 | QPVLTQPPSASVAPGQRVTISC<br>SGTTSNIEYNSVHWYQQLPGAA<br>PKLLIYNTDKRPPGIPDRFSASK<br>SGTSASLAISGLRSEDEATYYCA<br>TWDDSLSVMLFGGGTKVTVL<br>SEQ ID NO. 118 |
| FEA7 | QVQLVQSGGGLVQPGGSLRLSCAAS<br>GFTFNNYDMNWVRQAPGKGLEWVSY<br>ISSSGSTIYYADSVKGRFTISRDSAEKS<br>LYLQMNSLRAEDTAVYYCARRIDSWG<br>QGTLVTVSS<br>SEQ ID NO. 119 | DIVMTQSPLSLPVTLGQPASISC<br>RSSQSLVHSDGNTYLNWFQQR<br>PGQSPRRLIYKVSNRDSGVPDR<br>FSGSGSGTDFTLKISRVEAEDV<br>GVYYCMQGTHWPPYTFGQGTK<br>LEIK<br>SEQ ID NO. 120 |
| FEA12 | QVQLVESGGGLVQPGGSLRLSCAAS<br>GFTFSSYDMNWVRQAPGKGLEWLSY<br>ISSSGSAMFYADSVKGRFTISRDTAKN<br>SLYLQMNSLRDEDTAVYYCARQFDQ<br>WGQGTLVTVSS<br>SEQ ID NO. 121 | DIVMTQSPLSLPVTLGQPASISC<br>RSSQSLVHSDGNTYLNWFQQR<br>PGQSPRRLIYKISNRDSGVPDRF<br>SGSGSGTDFTLRISRVEAEDVG<br>VYYCMQGSHWPPFTFGPGTKV<br>DIK<br>SEQ ID NO. 122 |
| FEC2 | QVQLVQSGGGLVQPGGSLRLSCAAS<br>GFTVSNNYMSWVRQAPGKGLEWVSV<br>IYGGGSTFYANSVKGRFTISRDNSENT<br>LYLQMNSLRSEDTAVYYCARDSGYGD<br>FDYWGQGTLVTVSS<br>SEQ ID NO. 123 | DVVMTQSPSSLSASVGDRVTIT<br>CRASQSISSYLNWYQQKPGKAP<br>KLLIYDAYNLQSGVPSKFSGSGS<br>GTDFTLTISSLQPEDFATYYCQQ<br>SYSNPLTFGGGTKLEIK<br>SEQ ID NO. 124 |
| FEC4 | EVQLVESGAEVKKPGASVKVSCKTSG<br>YTFTGHYMDWVRQAPGQGLEWMGGI<br>NPKSGDTDYAQKFQGRVTMTRDTSIS<br>TVYIELNSLTSDDTAMYYCARDFHYW<br>GQGTLVTVSS<br>SEQ ID NO. 125 | DIVMTQSPLSLPVTLGQPASISC<br>KSSQSLLHSDGDTYLNWLLQRP<br>GQSPRRLIYKVSSRDSGVPDRF<br>SGSGSGTDFTLKISRVEADDVG<br>VYYCMQGSHWPPITFGQGTRLE<br>IK<br>SEQ ID NO. 126 |
| FEC10 | EVQLVESGGGLIQPGGSLRLSCAASG<br>FTVSSNYMSWVRQAPGKGLEWVSVI<br>YSGGSTYYADSVKGRFTISRDNSKNT<br>LYLQMNSLRAEDTAVYYCARDDSYGA<br>FDIWGQGTMVTVSS<br>SEQ ID NO. 127 | DIVMTQTPSSLSASVGDRVTITC<br>QASQDINNYLNWYQQKPGKAP<br>KLLIYDASNLETGVPSRVSGSGS<br>GTDFTFIISSLQPEDIGTYYCQQY<br>DNLPYTFGQGTKVEIK<br>SEQ ID NO. 128 |
| FED2 | EVQLVESGGGLVQPGRSLRLSCTASG<br>FTFGDYAMSWFRQAPGKGLEWVGFI<br>RSKAYGGTTEYAASVKGRFTISRDDS<br>KSIAYLQMNSLKTEDTAVYYCSSETGR<br>IDYWGQGTTVTVSS<br>SEQ ID NO. 129 | DIVMTQSPLSLPVTLGQPASISC<br>RSSQSLVHSDGNTYLNWFQQR<br>PGQSPRRLIYQVSNRDSGVPDR<br>FSGSGSGTDFTLKISRVEAEDV<br>GVYYCMQGSHWPPITFGQGTR<br>LEIK<br>SEQ ID NO. 130 |
| FED5 | EVQLVESGRGVVQPGTSLRLSCAASG<br>FTFSRFDMHWVRQAPGKGLEWVAFIS<br>YDATKKYYADSVRGRFTISRDNSKNT<br>FYLQMNSLRGEDTAVYYCARDYGEFD<br>NWGQGTLVTVSS<br>SEQ ID NO. 131 | DVVMTQSPLSLPVTLGQPASISC<br>RSSQSLVHSDGNTYLNWFQQR<br>PGQSPRRLIYKVSNRDSGVPDR<br>FSGSGSGTDFTLKISRVEAEDV<br>GVYYCMQGTHWPPITFGQGTK<br>VEIK<br>SEQ ID NO. 132 |
| FED8 | EVQLVESGGGLVQPGGSLRLSCAAS<br>GFIFGSYEMHWVRQAPGKGLEWVSYI<br>SGSGSKIYYADSVKGRFTISRDNAKNS<br>VYLQMNSLGAEDTAVYYCAGSLDYW<br>GQGTLVTVSS<br>SEQ ID NO. 133 | DVVMTQSPLSLPVTLGQPASISC<br>RSSQSLVHSDGNTYLNWFQQR<br>PGQSPRRLIYKVSNRDSGVPDR<br>FSGSGSGTDFTLKISRVEAEDV<br>GVYYCMQGTHWPPITFGQGTRL<br>EIK<br>SEQ ID NO. 134 |
| FEE10 | QVQLVQSGGGLVKPGGSLRLSCAAS<br>GFTFSSYEMNWVRQAPGKGLEWVSY<br>ISSSGSTIYYADSVKGRFTISRDNAKNT | DVVMTQSPLSLPVTLGQPASISC<br>RSSQSLVHSDGNTYLNWFQQR<br>PGQSPRRLIYKVSKRDSGVPDRI |

Sequence Listing
OprF (epitope 8)-binding Antibodies

| | Heavy chain variable domain region | Light chain variable domain region |
|---|---|---|
| | LYLQMNSLTAEDTAVYYCASFSHKAH WGQGTLVTVSS SEQ ID NO. 135 | SGSGSGTDFTLKISRVEAEDVG VYYCMQGTHWPPFTFGQGTRL EIK SEQ ID NO. 136 |
| FEF8 | QVQLVESGGGLVQPGGSLRLSCAAS GFTFSNYWMAWVRQAPGKGLEWVA NIKEDGSEKYYVDSVKGRFTISRDNAK NSVYLQMNSLRAEDTGVYYCAGRIFDI WGQGTMVTVSS SEQ ID NO. 137 | QSVVTQPPSVSAAPGQRVTISC SGSTSNIGTNYVSWFQHLPGAA PKLLIYDNSERPSGIPDRFSASK SGASATLGITGLQTGDEADYYC GTWDDSLSAGVFGGGTKVTVL SEQ ID NO. 138 |
| FEH3 | QVQLVQSGAEVKKPGASVKVSCKAS GYTLSSYHMHWVRQAPGQGLEWMG LIDPSDDTTVYAQKFQGRVTMTRDTS TSTVYMHLSSLRPEDTAVYFCARDLG NFWGQGTLVTVSS SEQ ID NO. 139 | DIVMTQSPLSLPVTLGQPASISC RSSQSLVHSDGNTYLNWFHQR PGQSPRRLIYQVSNRDSGVPDR FSGSGSGTDFTLKISRVEADDV GIYYCMQGTHWPPLTFGGGTKV EIK SEQ ID NO. 140 |
| FEH7 | EVQLVESGGGLVQPGGSLRLSCAAS GFTVSSNYMSWVRQAPGKGLEWVSV IYSGGSTYYADSVKGRFTISRDNSKDT LYLQMNSLRGEDTAVYYCARGLRDSS GYHWGSFDPWGQGTLVTVSS SEQ ID NO. 141 | SSELTQDPAVSVALGQTVRITCQ GDSLRFYFASWYQQRPGQAPR LVIYGENERPSGIPDRFSASTSG NTASLTIAGAQAEDEGDYYCNS RDNNDQHYVFGSGTKLTVL SEQ ID NO. 142 |

We claim:

1. A recombinant fully human anti-OprF antibody that binds to OprF, wherein the antibody comprises a heavy chain variable domain and a light chain variable domain selected from the group consisting of
   a) a heavy chain variable domain comprising an amino acid sequence that is at least 95% identical to SEQ ID NO. 3, and a light chain variable domain comprising an amino acid sequence that is at least 95% identical to SEQ ID NO. 4,
   b) a heavy chain variable domain comprising an amino acid sequence that is at least 95% identical to SEQ ID NO. 5, and a light chain variable domain comprising an amino acid sequence that is at least 95% identical to SEQ ID NO. 6, and
   c) a heavy chain variable domain comprising an amino acid sequence that is at least 95% identical to SEQ ID NO. 7, and a light chain variable domain comprising an amino acid sequence that is at least 95% identical to SEQ ID NO. 8.

2. The recombinant fully human anti-OprF antibody of claim 1, wherein the antibody has heavy chain/light chain variable domain sequences selected from the group consisting of SEQ ID NO. 3/SEQ ID NO. 4, SEQ ID NO. 5/SEQ ID NO. 6, and SEQ ID NO. 7/SEQ ID NO. 8.

3. The recombinant fully human anti-OprF antibody of claim 1, wherein the antibody is classified as an isotype selected from the group consisting of: IgG, IgM, IgD, IgA, and IgE.

4. A recombinant fully human anti-OprF antibody, or an antigen-binding fragment thereof, that binds to OprF, wherein the antibody, or antigen binding fragment, comprises a heavy chain variable domain and a light chain variable domain selected from the group consisting of
   a) a heavy chain variable domain comprising complementarity determining regions (CDRs) as set forth in SEQ ID NO. 3, and a light chain variable domain comprising CDRs as set forth in SEQ ID NO. 4;
   b) a heavy chain variable domain comprising CDRs as set forth in SEQ ID NO. 5, and a light chain variable domain comprising CDRs as set forth in SEQ ID NO. 6; and
   c) a heavy chain variable domain comprising CDRs as set forth in SEQ ID NO. 7, and a light chain variable domain comprising CDRs as set forth in SEQ ID NO. 8.

5. The recombinant fully human anti-OprF antibody of claim 4, which is a Fab fragment.

6. The fully human anti-OprF antibody Fab fragment of claim 5, wherein the Fab fragment has a heavy chain/light chain variable domain sequences selected from the group consisting of SEQ ID NO. 3/SEQ ID NO. 4, SEQ ID NO. 5/SEQ ID NO. 6, and SEQ ID NO. 7/SEQ ID NO. 8.

7. A single chain human anti-OprF antigen-binding fragment that binds to OprF, comprising a heavy chain variable domain and a light chain variable domain selected from the group consisting of
  a) a heavy chain variable region comprising an amino acid sequence that is at least 95% identical to SEQ ID NO. 3 and a light chain variable domain comprising an amino acid sequence that is at least 95% identical to SEQ ID NO. 4;
  b) a heavy chain variable region comprising an amino acid sequence that is at least 95% identical to SEQ ID NO. 5 and a light chain variable domain comprising an amino acid sequence that is at least 95% identical to SEQ ID NO. 6; and
  c) a heavy chain variable region comprising an amino acid sequence that is at least 95% identical to SEQ ID NO. 7, and a light chain variable domain comprising an amino acid sequence that is at least 95% identical to SEQ ID NO. 8,
  wherein a peptide linker connects the heavy chain variable domain and the light chain variable domain.

8. The single chain human anti-OprF antigen-binding fragment of claim 7, comprising heavy chain/light chain variable domain sequences selected from the group consisting of SEQ ID NO. 3/SEQ ID NO. 4, SEQ ID NO. 5/SEQ ID NO. 6, and SEQ ID NO. 7/SEQ ID NO. 8.

9. The recombinant fully human anti-OprF antigen-binding fragment of claim 4, which is a single chain antibody.

10. The recombinant fully human antibody, or antigen-binding fragment thereof, of claim 4, comprising heavy chain/light chain variable domain sequences as set forth in SEQ ID NO. 3/SEQ ID NO. 4, SEQ ID NO. 5/SEQ ID NO. 6, and SEQ ID NO. 7/SEQ ID NO. 8.

11. A pharmaceutical composition comprising the recombinant fully human anti-OprF antibody, or antigen binding fragment thereof, of claim 4, and a pharmaceutically acceptable excipient.

12. A method for treating a Pseudomonas aeruginosa infection in a subject, comprising administering an effective amount of an anti-OprF polypeptide to a subject in need thereof, wherein the anti-OprF polypeptide is selected from the group consisting of a recombinant fully human antibody, a fully human antibody Fab fragment, and a fully human single chain antibody, and wherein the polypeptide comprises a heavy chain variable domain and a light chain variable domain selected from the group consisting of:
  a) a heavy chain variable domain comprising CDRs as set forth in SEQ ID NO. 3 and a light chain variable domain comprising CDRs as set forth in SEQ ID NO. 4;
  b) a heavy chain variable domain comprising CDRs as set forth in SEQ ID NO. 5 and a light chain variable domain comprising CDRs as set forth in SEQ ID NO. 6; and
  c) a heavy chain variable domain comprising CDRs as set forth in SEQ ID NO. 7 and a light chain variable domain comprising CDRs as set forth in SEQ ID NO: 8;
  d) a heavy chain variable domain comprising an amino acid sequence that is at least 95% identical to SEQ ID NO. 3, and a light chain variable domain comprising an amino acid sequence that is at least 95% identical to SEQ ID NO. 4;
  e) a heavy chain variable domain comprising an amino acid sequence that is at least 95% identical to SEQ ID NO. 5, and a light chain variable domain comprising an amino acid sequence that is at least 95% identical to SEQ ID NO. 6; and
  f) a heavy chain variable domain comprising an amino acid sequence that is at least 95% identical to SEQ ID NO. 7, and a light chain variable domain comprising an amino acid sequence that is at least 95% identical to SEQ ID NO. 8.

13. The method of claim 12, wherein the recombinant fully human antibody comprises heavy chain/light chain variable domain sequences selected from the group consisting of SEQ ID NO. 3/SEQ ID NO. 4, SEQ ID NO. 5/SEQ ID NO. 6, and SEQ ID NO. 7/SEQ ID NO. 8.

14. The method of claim 12, wherein the fully human antibody Fab fragment comprises heavy chain/light chain variable domain sequences selected from the group consisting of SEQ ID NO. 3/SEQ ID NO. 4, SEQ ID NO. 5/SEQ ID NO. 6, and SEQ ID NO. 7/SEQ ID NO. 8.

15. The method of claim 12, wherein the fully human single chain human antibody comprises heavy chain/light chain variable domain sequences selected from the group consisting of SEQ ID NO. 3/SEQ ID NO. 4, SEQ ID NO. 5/SEQ ID NO. 6, and SEQ ID NO. 7/SEQ ID NO. 8.

16. The method of claim 12, wherein the subject further has a disease is selected from the group consisting of a burn wound infection, a surgical site infection, a diabetic foot ulcer, an infected wound, and cystic fibrosis.

17. A method for treating a subject having a Pseudomonas aeruginosa infection comprising administering an effective amount of the recombinant, fully human antibody of claim 1 to the subject.

18. The method of claim 17, wherein the subject further has a disease selected from the group consisting of a burn wound infection, a surgical site infection, a diabetic foot ulcer, an infected wound, and cystic fibrosis.

19. A method for treating a subject having a Pseudomonas aeruginosa infection, said method comprising administering an effective amount of the recombinant fully human anti-OprF antibody, or antigen binding fragment thereof, of claim 4 to the subject.

20. The method of claim 19, wherein the subject further has a disease selected from the group consisting of a burn wound infection, a surgical site infection, a diabetic foot ulcer, an infected wound, and cystic fibrosis.

21. The recombinant fully human anti-OprF antibody of claim 3, wherein the antibody is an IgG1 or an IgG4.

22. The recombinant fully anti-OprF human antibody, or an antigen-binding fragment thereof, of claim 4, wherein the antibody, or antigen-binding fragment, is classified as an isotype selected from the group consisting of: IgG, IgM, IgD, IgA, and IgE.

23. The recombinant fully anti-OprF human antibody, or an antigen-binding fragment thereof, of claim 22, wherein the antibody, or antigen-binding fragment, is an IgG1 or an IgG4.

24. The recombinant fully human anti-OprF antibody, or an antigen-binding fragment thereof, of claim 4, wherein the antibody, or antigen-binding fragment thereof, comprises a heavy chain variable domain and a light chain variable domain selected from the group consisting of
  a) a heavy chain variable domain comprising the CDRs as set forth in SEQ ID NO. 3 and comprising an amino acid sequence that is at least 95% identical to SEQ ID NO. 3, and a light chain variable domain comprising the CDRs as set forth in SEQ ID NO. 4 and an amino acid sequence that is at least 95% identical to SEQ ID NO. 4;

b) a heavy chain variable domain comprising the CDRs as set forth in SEQ ID NO. 5, and an amino acid sequence that is at least 95% identical to SEQ ID NO: 5, and a light chain variable domain comprising the CDRs as set forth in SEQ ID NO. 6 and an amino acid sequence that is at least 95% identical to SEQ ID NO. 6; and c) a heavy chain variable domain comprising the CDRs as set forth in SEQ ID NO. 7 and an amino acid sequence that is at least 95% identical to SEQ ID NO. 7, and a light chain variable domain comprising the CDRs as set forth in SEQ ID NO. 8 and an amino acid sequence that is at least 95% identical to SEQ ID NO. 8.

25. The recombinant anti-OprF human antibody, or antigen-binding fragment of claim 4, wherein antibody, or antigen-binding fragment is a monoclonal antibody, a human antibody, a humanized antibody, an Fab, an Fab', an F(ab')2, an Fv, a domain antibody (dAb), a single-chain antibody (scFv), a chimeric antibody, a diabody, a triabody or a tetrabody.

* * * * *

SEQUENCE LISTING

<160> NUMBER OF SEQ ID NOS: 142

<210> SEQ ID NO 1
<211> LENGTH: 125
<212> TYPE: PRT
<213> ORGANISM: Homo Sapiens

<400> SEQUENCE: 1

Glu Val Gln Leu Val Gln Ser Gly Ala Glu Met Lys Lys Pro Gly Ser
1               5                   10                  15

Ser Val Lys Val Ser Cys Lys Ala Ser Gly Asp Thr Phe Ser Asn Tyr
            20                  25                  30

Asn Phe Asn Trp Val Arg Gln Ala Pro Gly Gln Gly Leu Glu Trp Met
        35                  40                  45

Gly Gly Ile Thr Pro Ile Phe Gly Ala Ala Gln Tyr Ala Gln Lys Phe
    50                  55                  60

Gln Asp Arg Val Thr Ile Ile Ala Asp Glu Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Gly Gly Trp Ala Gly Phe Cys Ser Ser Ala Ser Cys Tyr Arg Phe
            100                 105                 110

Asp Tyr Trp Gly Gln Gly Thr Thr Val Thr Val Ser Ser
        115                 120                 125

<210> SEQ ID NO 2
<211> LENGTH: 110
<212> TYPE: PRT
<213> ORGANISM: Homo Sapiens

<400> SEQUENCE: 2

```
Ser Tyr Glu Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Tyr
            20                  25                  30

Tyr Val Ser Trp Tyr Gln Gln Leu Pro Gly Thr Ala Pro Lys Leu Leu
            35                  40                  45

Ile Tyr Asp Asn Asp Lys Arg Pro Ser Gly Ile Pro Asp Arg Phe Ser
        50                  55                  60

Ala Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Thr Leu
                85                  90                  95

Ser Gly Gly Ile Leu Gly Thr Gly Thr Lys Leu Thr Val Leu
            100                 105                 110

<210> SEQ ID NO 3
<211> LENGTH: 117
<212> TYPE: PRT
<213> ORGANISM: Homo Sapiens

<400> SEQUENCE: 3

Gln Val Gln Leu Val Val Ser Gly Asp Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Leu
            35                  40                  45

Gly Trp Met Ser Pro Asn Ser Gly Asn Thr Asp Tyr Ala Glu Lys Phe
        50                  55                  60

Gln Gly Arg Val Thr Met Thr Arg Asp Thr Ser Ile Thr Thr Ala Tyr
65                  70                  75                  80

Met Glu Leu Ser Ser Leu Ala Ser Glu Asp Thr Ala Val Tyr Tyr Cys
                85                  90                  95

Ala Arg Gly Val Ala Ala Gly Leu Asp Tyr Trp Gly Gln Gly Thr Leu
            100                 105                 110

Val Thr Val Ser Ser
        115

<210> SEQ ID NO 4
<211> LENGTH: 110
<212> TYPE: PRT
<213> ORGANISM: Homo Sapiens

<400> SEQUENCE: 4

Leu Pro Val Leu Thr Gln Ser Ala Ser Val Ser Gly Ser Pro Gly Gln
1               5                   10                  15

Ser Ile Thr Ile Ser Cys Thr Gly Thr Ser Thr Asp Val Asp Tyr Ser
            20                  25                  30

Asn Tyr Val Ser Trp Tyr Gln His His Pro Gly Lys Ala Pro Lys Leu
            35                  40                  45

Met Ile Tyr Asp Val Ser Arg Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Gly
                85                  90                  95
```

```
Thr Thr Leu Val Phe Gly Gly Gly Thr Lys Val Thr Val Leu
            100                 105                 110
```

<210> SEQ ID NO 5
<211> LENGTH: 123
<212> TYPE: PRT
<213> ORGANISM: Homo Sapiens

<400> SEQUENCE: 5

```
Glu Val Gln Leu Val Glu Ser Gly Pro Gly Leu Ala Lys Pro Ser Glu
1               5                   10                  15

Thr Leu Ser Leu Thr Cys Ser Val Phe Gly Gly Ser Ile Arg Arg Tyr
            20                  25                  30

Tyr Trp Ser Trp Ile Arg Gln Ser Pro Gly Lys Gly Leu Glu Trp Ile
        35                  40                  45

Gly Phe Phe Tyr His Ser Gly Ser Ala Asp Tyr Asn Pro Ser Pro Asn
    50                  55                  60

Tyr Asn Pro Ser Phe Lys Ser Arg Val Thr Ile Ser Val Asp Thr Ser
65                  70                  75                  80

Lys Thr Gln Phe Ser Leu Lys Met Thr Ser Val Thr Ala Ala Asp Thr
                85                  90                  95

Ala Val Tyr Tyr Cys Ala Lys Gly Asp Gly Ser Trp Tyr Leu Asp Ser
            100                 105                 110

Trp Gly Gln Gly Thr Leu Val Thr Val Ser Ser
            115                 120
```

<210> SEQ ID NO 6
<211> LENGTH: 108
<212> TYPE: PRT
<213> ORGANISM: Homo Sapiens

<400> SEQUENCE: 6

```
Asp Ile Val Met Thr Gln Ser Pro Ser Ser Leu Ser Ala Ser Val Gly
1               5                   10                  15

Asp Arg Val Thr Ile Thr Cys Arg Ala Ser His Ser Ile Ser Arg Ser
            20                  25                  30

Leu Asn Trp Tyr Gln Gln Lys Pro Gly Lys Ala Pro Lys Leu Leu Ile
        35                  40                  45

Tyr Ala Ala Ser Ile Leu Gln Ser Gly Val Ser Ser Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Thr Tyr Tyr Cys Gln Glu Ser Asp Ser Pro Pro Pro
                85                  90                  95

Phe Thr Phe Gly Pro Gly Thr Lys Val Glu Ile Lys
            100                 105
```

<210> SEQ ID NO 7
<211> LENGTH: 125
<212> TYPE: PRT
<213> ORGANISM: Homo Sapiens

<400> SEQUENCE: 7

```
Glu Val Gln Leu Val Gln Ser Gly Ala Glu Met Lys Lys Pro Gly Ser
1               5                   10                  15

Ser Val Lys Val Ser Cys Lys Ala Ser Gly Asp Thr Phe Ser Asn Tyr
            20                  25                  30
```

Asn Phe Asn Trp Val Arg Gln Ala Pro Gly Gln Gly Leu Glu Trp Met
            35                  40                  45

Gly Gly Ile Thr Pro Ile Phe Gly Ala Ala Gln Tyr Ala Gln Lys Phe
 50                  55                  60

Gln Asp Arg Val Thr Ile Ile Ala Asp Glu Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Gly Gly Trp Ala Gly Phe Cys Ser Ser Ala Ser Cys Tyr Arg Phe
            100                 105                 110

Asp Tyr Trp Gly Gln Gly Thr Thr Val Thr Val Ser Ser
            115                 120                 125

<210> SEQ ID NO 8
<211> LENGTH: 110
<212> TYPE: PRT
<213> ORGANISM: Homo Sapiens

<400> SEQUENCE: 8

Ser Tyr Glu Leu Thr Gln Pro Pro Ser Val Ser Ala Ala Pro Gly Gln
 1               5                   10                  15

Lys Val Thr Ile Ser Cys Ser Gly Ser Ser Ser Asn Ile Gly Asn Tyr
             20                  25                  30

Tyr Val Ser Trp Tyr Gln Gln Leu Pro Gly Thr Ala Pro Lys Leu Leu
             35                  40                  45

Ile Tyr Asp Asn Asp Lys Arg Pro Ser Gly Ile Pro Asp Arg Phe Ser
 50                  55                  60

Ala Ser Lys Ser Gly Thr Ser Ala Ser Leu Ala Ile Thr Gly Leu Gln
 65                  70                  75                  80

Ala Glu Asp Glu Ala Asp Tyr Tyr Cys Gln Ser Tyr Asp Arg Thr Leu
                 85                  90                  95

Ser Gly Gly Ile Leu Gly Thr Gly Thr Lys Leu Thr Val Leu
            100                 105                 110

<210> SEQ ID NO 9
<211> LENGTH: 117
<212> TYPE: PRT
<213> ORGANISM: Homo Sapiens

<400> SEQUENCE: 9

Gln Val Gln Leu Val Gln Ser Gly Ala Glu Val Lys Lys Pro Gly Ala
 1               5                   10                  15

Ser Val Arg Val Ser Cys Lys Ala Ser Glu Tyr Thr Phe Thr Ala Tyr
             20                  25                  30

Tyr Leu His Trp Val Arg Gln Ala Pro Gly Gln Gly Leu Glu Trp Met
             35                  40                  45

Gly Arg Ile Asp Pro Asn Ser Gly Gly Thr Asn Phe Ala Gln Lys Phe
 50                  55                  60

Gln Gly Arg Val Thr Met Thr Ser Asp Thr Ser Val Ser Thr Ala Tyr
 65                  70                  75                  80

Met Glu Leu Arg Gly Leu Arg Ser Asp Asp Thr Ala Val Tyr Tyr Cys
                 85                  90                  95

Ala Arg Ala Gln Tyr Ala Ala Lys Asp Tyr Trp Gly Gln Gly Thr Leu
            100                 105                 110

Val Thr Val Ser Ser
            115

```
<210> SEQ ID NO 10
<211> LENGTH: 108
<212> TYPE: PRT
<213> ORGANISM: Homo Sapiens

<400> SEQUENCE: 10

Ser Tyr Glu Leu Met Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Ala His
                85                  90                  95

Val Val Phe Gly Gly Gly Thr Lys Leu Thr Val Leu
            100                 105

<210> SEQ ID NO 11
<211> LENGTH: 121
<212> TYPE: PRT
<213> ORGANISM: Homo Sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Gly Gly Ala Ala Ala Gly Leu Asn Thr Asp Tyr Trp Gly
            100                 105                 110

Gln Gly Thr Leu Val Thr Val Ser Ser
        115                 120

<210> SEQ ID NO 12
<211> LENGTH: 110
<212> TYPE: PRT
<213> ORGANISM: Homo Sapiens

<400> SEQUENCE: 12

Ser Tyr Glu Leu Met Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
```

```
                    50                  55                  60
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Arg Val Phe Gly Thr Gly Thr Lys Val Thr Val Leu
            100                 105                 110

<210> SEQ ID NO 13
<211> LENGTH: 115
<212> TYPE: PRT
<213> ORGANISM: Homo Sapiens

<400> SEQUENCE: 13

Gln Val Gln Leu Val Glu Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
             20                  25                  30

Tyr Met Ser Trp Val Arg Gln Ala Pro Gly Lys Gly Leu Glu Trp Val
         35                  40                  45

Ser Val Ile Tyr Ser Gly Gly Thr Lys Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Phe Cys Ala
                 85                  90                  95

Arg Gly Asp Asp Ala Phe Asp Ile Trp Gly Gln Gly Thr Met Val Thr
            100                 105                 110

Val Ser Ser
        115

<210> SEQ ID NO 14
<211> LENGTH: 110
<212> TYPE: PRT
<213> ORGANISM: Homo Sapiens

<400> SEQUENCE: 14

Gln Ser Val Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Asn Thr Ile Val Phe Gly Ser Gly Thr Lys Val Thr Val Leu
            100                 105                 110

<210> SEQ ID NO 15
<211> LENGTH: 113
<212> TYPE: PRT
<213> ORGANISM: Homo Sapiens

<400> SEQUENCE: 15
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Gly Ser Asn Asn
            20                  25                  30

Tyr Met Ser Trp Val Arg Gln Ala Pro Gly Lys Gly Leu Glu Trp Val
        35                  40                  45

Ser Ile Ile Tyr Ser Gly Gly Asn Ala Tyr Tyr Ala Asp Ser Val Lys
    50                  55                  60

Gly Arg Phe Thr Ile Ser Arg Asp Asn Ser Lys Asn Ile Leu Tyr Phe
65              70                  75                  80

Gln Met Asn Ser Leu Arg Val Glu Asp Thr Ala Val Tyr Tyr Cys Ala
                85                  90                  95

Glu Gly Tyr Gly Gly Val Asp Tyr Trp Gly Gln Gly Thr Leu Val Thr
                100                 105                 110

Val

<210> SEQ ID NO 16
<211> LENGTH: 115
<212> TYPE: PRT
<213> ORGANISM: Homo Sapiens

<400> SEQUENCE: 16

Ser Ser Asp Val Val Met Thr Gln Ser Pro Asp Ser Leu Ala Val Ser
1               5                   10                  15

Leu Gly Glu Arg Ala Thr Ile Asn Cys Lys Ser Ser Gln Ser Val Leu
            20                  25                  30

Tyr Ser Ser Asn Asn Lys Asn Tyr Leu Ala Trp Tyr Gln Gln Lys Pro
        35                  40                  45

Gly Gln Pro Pro Lys Leu Leu Ile Tyr Trp Ala Ser Thr Arg Glu Ser
    50                  55                  60

Gly Val Pro Asp Arg Phe Ser Gly Ser Gly Ser Gly Thr Asp Phe Thr
65              70                  75                  80

Leu Thr Ile Ser Ser Leu Gln Ala Glu Asp Val Ala Val Tyr Tyr Cys
                85                  90                  95

Gln Gln Tyr Tyr Ser Ser Pro Phe Ser Phe Gly Pro Gly Thr Lys Val
                100                 105                 110

Asp Ile Lys
        115

<210> SEQ ID NO 17
<211> LENGTH: 118
<212> TYPE: PRT
<213> ORGANISM: Homo Sapiens

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65              70                  75                  80

```
Met Glu Leu Ser Ser Leu Arg Ala Glu Asp Met Ala Val Tyr Tyr Cys
                85                  90                  95

Ala Arg Glu Gly Leu Pro Asp Ala Phe Asp Ile Trp Gly Gln Gly Thr
            100                 105                 110

Met Val Thr Val Ser Ser
        115
```

<210> SEQ ID NO 18
<211> LENGTH: 110
<212> TYPE: PRT
<213> ORGANISM: Homo Sapiens

<400> SEQUENCE: 18

```
Gln Ala Gly Leu Thr Gln Pro Ala Ser Val Ser Gly Ser Pro Gly Gln
1               5                   10                  15

Ser Ile Thr Leu Ser Cys Thr Gly Thr Ser Ser Asp Val Gly Gly Tyr
            20                  25                  30

Asn Tyr Val Thr Trp Phe Gln Gln His Pro Gly Lys Ala Pro Lys Leu
        35                  40                  45

Met Ile Tyr Asp Val Ser Lys Arg Pro Ser Gly Ala Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Gly Thr Tyr Val Phe Gly Thr Gly Thr Lys Leu Thr Val Leu
            100                 105                 110
```

<210> SEQ ID NO 19
<211> LENGTH: 119
<212> TYPE: PRT
<213> ORGANISM: Homo Sapiens

<400> SEQUENCE: 19

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ile Tyr Asp Phe Asp Ala Phe Asp Ile Trp Gly Gln Gly
            100                 105                 110

Thr Met Val Thr Val Ser Ser
        115
```

<210> SEQ ID NO 20
<211> LENGTH: 108
<212> TYPE: PRT
<213> ORGANISM: Homo Sapiens

<400> SEQUENCE: 20

```
Ser Tyr Glu Leu Met Gln Pro Pro Ser Val Ser Val Ala Pro Gly Lys
```

```
            1               5                  10                 15
        Thr Ala Arg Ile Thr Cys Gly Gly Asn Asn Ile Gly Ser Lys Ser Val
                        20                 25                 30

His Trp Tyr Gln Gln Lys Pro Gly Gln Ala Pro Val Leu Val Ile Tyr
                        35                 40                 45

Tyr Asp Ser Asp Arg Pro Ser Gly Ile Pro Glu Arg Phe Ser Gly Ser
                    50                 55                 60

Asn Ser Gly Asn Thr Ala Thr Leu Thr Ile Ser Arg Val Glu Ala Gly
                65                 70                 75                 80

Asp Glu Ala Asp Tyr Tyr Cys Gln Val Trp Asp Ser Arg Ser Asp Gln
                            85                 90                 95

Val Ile Phe Gly Gly Gly Thr Gln Leu Thr Val Leu
                        100                105

<210> SEQ ID NO 21
<211> LENGTH: 121
<212> TYPE: PRT
<213> ORGANISM: Homo Sapiens

<400> SEQUENCE: 21

Gln Val Gln Leu Val Glu Ser Gly Gly Gly Leu Val Gln Pro Gly Gly
        1               5                  10                 15

Ser Leu Arg Leu Ser Cys Ala Ala Ser Gly Phe Thr Val Ser Ser Asn
                        20                 25                 30

Tyr Met Ser Trp Val Arg Gln Ala Pro Gly Lys Gly Leu Glu Trp Val
                        35                 40                 45

Ser Val Ile Tyr Ser Gly Gly Ser Thr Tyr Tyr Ala Asp Ser Val Lys
                    50                 55                 60

Gly Arg Phe Thr Ile Ser Arg Asp Asn Ser Lys Asn Thr Leu Tyr Leu
        65                 70                 75                 80

Gln Met Asn Ser Leu Arg Ala Glu Asp Thr Ala Val Tyr Tyr Cys Ala
                        85                 90                 95

Arg Glu Asp Ser Ser Ser Trp Tyr Trp Asn Ala Phe Asp Ile Trp Gly
                        100                105                110

Gln Gly Thr Met Val Thr Val Ser Ser
                    115                120

<210> SEQ ID NO 22
<211> LENGTH: 107
<212> TYPE: PRT
<213> ORGANISM: Homo Sapiens

<400> SEQUENCE: 22

Tyr Glu Leu Met Gln Pro Pro Ser Val Ser Val Ala Pro Gly Lys Thr
        1               5                  10                 15

Ala Arg Ile Thr Cys Gly Gly Asn Asn Ile Gly Ser Lys Ser Val His
                        20                 25                 30

Trp Tyr Gln Gln Lys Pro Gly Gln Ala Pro Val Leu Val Ile Tyr Tyr
                        35                 40                 45

Asp Ser Asp Arg Pro Ser Gly Ile Pro Glu Arg Phe Ser Gly Ser Asn
                    50                 55                 60

Ser Gly Asn Thr Ala Thr Leu Thr Ile Ser Arg Val Glu Ala Gly Asp
        65                 70                 75                 80

Glu Ala Asp Tyr Tyr Cys Gln Val Trp Asp Ser Ser Ser Asp His Pro
                        85                 90                 95

Val Phe Gly Gly Gly Thr Lys Leu Thr Val Leu
```

-continued

<210> SEQ ID NO 23
<211> LENGTH: 119
<212> TYPE: PRT
<213> ORGANISM: Homo Sapiens

<400> SEQUENCE: 23

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Ser Tyr
            20                  25                  30
Ala Met Asn Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Ser Thr Leu Trp Phe Ser Glu Phe Asp Tyr Trp Gly Gln Gly
            100                 105                 110
Thr Leu Val Thr Val Ser Ser
        115

<210> SEQ ID NO 24
<211> LENGTH: 106
<212> TYPE: PRT
<213> ORGANISM: Homo Sapiens

<400> SEQUENCE: 24

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Thr Ile Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Ala Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Thr Tyr Tyr Cys Gln Gln Tyr Asp Thr Ser Ser Thr
                85                  90                  95
Phe Gly Gln Gly Thr Lys Val Asp Ile Lys
            100                 105

<210> SEQ ID NO 25
<211> LENGTH: 121
<212> TYPE: PRT
<213> ORGANISM: Homo Sapiens

<400> SEQUENCE: 25

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Glu Met Asn Trp Val Arg Gln Ala Pro Gly Lys Gly Leu Glu Trp Val
        35                  40                  45

```
Ser Tyr Ile Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Leu Ile Tyr Asp Ser Ser Gly Tyr Tyr Phe Asp Tyr Trp Gly
            100                 105                 110

Gln Gly Thr Leu Val Thr Val Ser Ser
            115                 120
```

<210> SEQ ID NO 26
<211> LENGTH: 112
<212> TYPE: PRT
<213> ORGANISM: Homo Sapiens

<400> SEQUENCE: 26

```
Asp Ile Gln Leu Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ser His Trp Pro His Thr Phe Gly Gln Gly Thr Lys Leu Glu Ile Lys
            100                 105                 110
```

<210> SEQ ID NO 27
<211> LENGTH: 119
<212> TYPE: PRT
<213> ORGANISM: Homo Sapiens

<400> SEQUENCE: 27

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Ile Ile Asn Pro Ser Gly Gly Ser Thr Ser Tyr Ala Gln Lys Phe
     50                  55                  60

Gln Gly Arg Val Thr Met Thr Met Asp Thr Ser Ala Asn Thr Val Tyr
 65                  70                  75                  80

Met Glu Leu Ser Arg Leu Arg Ser Asp Asp Thr Ala Val Tyr Tyr Cys
                 85                  90                  95

Ala Arg Asp Trp Phe Ser Glu Tyr Phe Asp Tyr Trp Gly Gln Gly
            100                 105                 110

Thr Leu Val Thr Val Ser Ser
            115
```

<210> SEQ ID NO 28

<211> LENGTH: 110
<212> TYPE: PRT
<213> ORGANISM: Homo Sapiens

<400> SEQUENCE: 28

Gln Ser Val Val Thr Gln Pro Pro Ser Val Ser Ala Ala Pro Gly Gln
1               5                   10                  15
Lys Val Thr Ile Ser Cys Ser Gly Ser Asn Ser Asn Ile Gly Asn Asn
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
50                  55                  60
Gly Ser Lys Ser Gly Thr Ser Ala Thr Leu Ala Ile Thr Gly Leu Gln
65                  70                  75                  80
Thr Gly Asp Glu Ala Asp Tyr Tyr Cys Gly Thr Trp Asp Ser Ser Leu
                85                  90                  95
Ser Gly Gly Val Phe Gly Gly Gly Thr Lys Leu Thr Val Leu
            100                 105                 110

<210> SEQ ID NO 29
<211> LENGTH: 130
<212> TYPE: PRT
<213> ORGANISM: Homo Sapiens

<400> SEQUENCE: 29

Glu Val Gln Leu Val Gln Ser Gly Gly Gly Val Val Gln Pro Gly Arg
1               5                   10                  15
Ser Leu Arg Leu Ser Cys Ala Ala Ser Gly Phe Thr Phe Ser Ile Tyr
            20                  25                  30
Gly Met His Trp Val Arg Gln Ala Pro Gly Lys Gly Leu Glu Trp Val
        35                  40                  45
Ala Val Ile Trp Asp Asp Gly Ser Lys Lys Tyr Tyr Ala Asp Ser Val
50                  55                  60
Lys Gly Arg Phe Thr Ile Ser Arg Asp Asn Ser Lys Asn Thr Leu Tyr
65                  70                  75                  80
Leu Gln Met Asn Thr Leu Arg Ala Asp Asp Thr Ala Val Tyr Tyr Cys
                85                  90                  95
Ala Gly Glu Leu Trp Lys Tyr Tyr Asp Ser Ser Gly Phe Tyr Ser Ile
            100                 105                 110
Asn Pro Glu Tyr Phe Gln His Trp Gly Gln Gly Thr Leu Val Thr Val
        115                 120                 125
Ser Ser
    130

<210> SEQ ID NO 30
<211> LENGTH: 110
<212> TYPE: PRT
<213> ORGANISM: Homo Sapiens

<400> SEQUENCE: 30

Gln Ala Gly Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Tyr Val Ser Trp Tyr Gln Gln His Pro Gly Lys Ala Pro Lys Leu
        35                  40                  45

```
Ile Ile Tyr Asp Val Ser Glu Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Ser
                 85                  90                  95

Ser Thr Leu Leu Phe Gly Gly Gly Thr Lys Leu Thr Val Leu
            100                 105                 110

<210> SEQ ID NO 31
<211> LENGTH: 116
<212> TYPE: PRT
<213> ORGANISM: Homo Sapiens

<400> SEQUENCE: 31

Glu Val Gln Leu Val Gln Ser Gly Gly Gly Leu Ile Gln Pro Gly Gly
 1               5                  10                  15

Ser Leu Arg Leu Ser Cys Ala Ala Ser Gly Phe Ser Val Ser Ser Asp
            20                  25                  30

Tyr Met Ser Trp Val Arg Gln Ala Pro Gly Lys Gly Leu Glu Trp Val
        35                  40                  45

Ser Val Ile Tyr Thr Gly Gly Thr Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Tyr Gly Asp Ser Phe Asp Tyr Trp Gly Gln Gly Thr Leu Val
            100                 105                 110

Thr Val Ser Ser
        115

<210> SEQ ID NO 32
<211> LENGTH: 110
<212> TYPE: PRT
<213> ORGANISM: Homo Sapiens

<400> SEQUENCE: 32

Gln Ala Gly Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Lys Ser
                 85                  90                  95

Asn Thr Leu Val Phe Gly Gly Gly Thr Lys Val Thr Val Leu
            100                 105                 110

<210> SEQ ID NO 33
<211> LENGTH: 116
<212> TYPE: PRT
<213> ORGANISM: Homo Sapiens
```

<400> SEQUENCE: 33

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Trp Gly Tyr Asp Lys Gly Asp Trp Gln Gly Thr Leu Val
            100                 105                 110

Thr Val Ser Ser
            115

<210> SEQ ID NO 34
<211> LENGTH: 108
<212> TYPE: PRT
<213> ORGANISM: Homo Sapiens

<400> SEQUENCE: 34

Leu Pro Val Leu Thr Gln Pro Pro Ser Leu Ser Val Ala Pro Gly Lys
1               5                   10                  15

Thr Ala Arg Ile Thr Cys Gly Gly Asn Asn Ile Asp Ser Thr Gly Val
            20                  25                  30

His Trp Tyr Gln Gln Lys Ala Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ser Ser Ser Asp His
            85                  90                  95

Val Val Phe Gly Gly Gly Thr Lys Leu Thr Val Leu
            100                 105

<210> SEQ ID NO 35
<211> LENGTH: 116
<212> TYPE: PRT
<213> ORGANISM: Homo Sapiens

<400> SEQUENCE: 35

Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala

```
                85                  90                  95
Arg Asp Tyr Gly Asp Tyr Phe Asp Tyr Trp Gly Gln Gly Thr Leu Val
            100                 105                 110

Thr Val Ser Ser
        115

<210> SEQ ID NO 36
<211> LENGTH: 110
<212> TYPE: PRT
<213> ORGANISM: Homo Sapiens

<400> SEQUENCE: 36

Ser Tyr Glu Leu Met Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Asp Trp Tyr Gln Gln Leu Pro Gly Thr Ala Pro Lys Leu Leu
            35                  40                  45

Ile Tyr Ser Asn Asn Glu Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu
            100                 105                 110

<210> SEQ ID NO 37
<211> LENGTH: 121
<212> TYPE: PRT
<213> ORGANISM: Homo Sapiens

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Ser Pro Gly Ala Tyr Ser Ser Gly Trp Tyr Asp Tyr Trp Gly
            100                 105                 110

Gln Gly Thr Leu Val Thr Val Ser Ser
            115                 120

<210> SEQ ID NO 38
<211> LENGTH: 110
<212> TYPE: PRT
<213> ORGANISM: Homo Sapiens

<400> SEQUENCE: 38

Gln Pro Val Leu Thr Gln Pro Ser Val Ser Val Ala Pro Gly Ala
1               5                   10                  15
```

Ala Ala Arg Ile Thr Cys Gly Gly Asn Asn Ile Gly Ser Gln Ile Val
            20                  25                  30

His Trp Tyr Arg Gln Lys Pro Gly Gln Ala Pro Val Leu Val Leu Tyr
        35                  40                  45

Tyr Asp Thr Glu Arg Pro Ser Gly Ile Pro Glu Arg Phe Ser Gly Ser
 50                  55                  60

Asn Ser Gly Asn Thr Ala Thr Leu Thr Val Ser Arg Val Glu Ala Gly
 65                  70                  75                  80

Asp Glu Ala Asp Tyr Phe Cys Gln Val Trp Asp Leu Ser His Asp His
                    85                  90                  95

Pro Gly Trp Leu Phe Gly Gly Gly Thr Lys Leu Thr Val Leu
            100                 105                 110

<210> SEQ ID NO 39
<211> LENGTH: 116
<212> TYPE: PRT
<213> ORGANISM: Homo Sapiens

<400> SEQUENCE: 39

Gln Val Gln Leu Val Glu Ser Gly Gly Gly Leu Ile Gln Pro Gly Gly
 1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                    85                  90                  95

Arg Glu Gly Gly Glu His Phe Asp Tyr Trp Gly Gln Gly Thr Leu Val
            100                 105                 110

Thr Val Ser Ser
        115

<210> SEQ ID NO 40
<211> LENGTH: 110
<212> TYPE: PRT
<213> ORGANISM: Homo Sapiens

<400> SEQUENCE: 40

Gln Ala Val Leu Thr Gln Pro Ala Ser Val Ser Gly Ser Pro Gly Gln
 1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Gly Asp Tyr Tyr Cys Phe Ser Tyr Thr Ser Ser
                    85                  90                  95

Ser Thr Leu Val Phe Gly Gly Gly Thr Lys Leu Thr Val Leu
            100                 105                 110

<210> SEQ ID NO 41
<211> LENGTH: 128
<212> TYPE: PRT
<213> ORGANISM: Homo Sapiens

<400> SEQUENCE: 41

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Tyr Tyr Gly Ser Gly Thr Ala Asn Asp Tyr Tyr Tyr
                100                 105                 110

Tyr Gly Met Asp Val Trp Gly Gln Gly Thr Thr Val Thr Val Ser Ser
            115                 120                 125

<210> SEQ ID NO 42
<211> LENGTH: 110
<212> TYPE: PRT
<213> ORGANISM: Homo Sapiens

<400> SEQUENCE: 42

Leu Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
                20                  25                  30

Pro Val Asn Trp Tyr Gln Gln Val Pro Gly Thr Ala Pro Lys Leu Leu
            35                  40                  45

Ile His Ser Ser Asn Gln Arg Pro Ser Gly Val Pro Asp Arg Phe Ser
        50                  55                  60

Gly Ser Lys Ser Gly Ala Ser Ala Ser Leu Ala Ile Ser Gly Leu Gln
65                  70                  75                  80

Ser Glu Asp Glu Ala Asp Tyr Tyr Cys Ala Ala Trp Asp Asp Ile Leu
                85                  90                  95

Asn Gly Leu Val Phe Gly Gly Gly Thr Lys Leu Thr Val Leu
                100                 105                 110

<210> SEQ ID NO 43
<211> LENGTH: 116
<212> TYPE: PRT
<213> ORGANISM: Homo Sapiens

<400> SEQUENCE: 43

Gln Val Gln Leu Val Gln Ser Gly Gly Gly Leu Val Gln Pro Gly Glu
1               5                   10                  15

Ser Leu Arg Leu Ser Cys Ala Ala Ser Gly Phe Thr Val Ser Ser Asn
                20                  25                  30

His Met Ala Trp Val Arg Gln Ala Pro Gly Lys Gly Leu Glu Trp Val
            35                  40                  45

Ser Leu Ile Tyr Asn Gly Asp Ser Thr Tyr Tyr Pro Asp Ser Val Lys
            50                  55                  60

Gly Arg Phe Thr Ile Ser Arg Asp Asn Ser Lys Asn Ala Leu Tyr Leu
 65                  70                  75                  80

Gln Met Asn Ser Leu Arg Ala Glu Asp Thr Ala Val Tyr Tyr Cys Ala
                 85                  90                  95

Arg Asp Trp Gly Tyr Asp Thr Ala Asp Trp Gly Gln Gly Thr Leu Val
            100                 105                 110

Thr Val Ser Ser
        115

<210> SEQ ID NO 44
<211> LENGTH: 111
<212> TYPE: PRT
<213> ORGANISM: Homo Sapiens

<400> SEQUENCE: 44

Gln Pro Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Asn
                 85                  90                  95

Ser Thr Leu Tyr Val Phe Gly Thr Gly Thr Lys Val Thr Val Leu
            100                 105                 110

<210> SEQ ID NO 45
<211> LENGTH: 122
<212> TYPE: PRT
<213> ORGANISM: Homo Sapiens

<400> SEQUENCE: 45

Gln Val Gln Leu Val Gln Ser Gly Ala Glu Val Lys Lys Pro Gly Ala
 1               5                  10                  15

Ser Val Lys Val Ser Cys Lys Ala Ser Gly Asp Thr Phe Thr Gly Gln
            20                  25                  30

Tyr Met Asn Trp Val Arg Gln Ala Pro Gly Gln Gly Leu Glu Trp Met
         35                  40                  45

Gly Trp Ile Asn Pro Asn Ser Gly Phe Thr Asn Tyr Ala Gln Lys Phe
 50                  55                  60

Gln Gly Arg Val Thr Met Thr Trp Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Ser Trp Asp Tyr Tyr Ser Tyr Tyr Gly Met Asp Val Trp
            100                 105                 110

Gly Gln Gly Thr Thr Val Thr Val Ser Ser
        115                 120

<210> SEQ ID NO 46
<211> LENGTH: 107

<212> TYPE: PRT
<213> ORGANISM: Homo Sapiens

<400> SEQUENCE: 46

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Thr Ser Tyr
            20                  25                  30

Leu Ala Trp Tyr Gln Gln Lys Pro Gly Lys Ala Pro Lys Leu Leu Val
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gly Thr Pro Tyr
                85                  90                  95

Thr Phe Gly Gln Gly Thr Lys Leu Glu Ile Lys
            100                 105

<210> SEQ ID NO 47
<211> LENGTH: 115
<212> TYPE: PRT
<213> ORGANISM: Homo Sapiens

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Gly Ser Asn Asn
            20                  25                  30

Tyr Met Ser Trp Val Arg Gln Ala Pro Gly Lys Gly Leu Glu Trp Val
        35                  40                  45

Ser Ile Ile Tyr Ser Gly Gly Asn Ala Tyr Tyr Ala Asp Ser Val Lys
    50                  55                  60

Gly Arg Phe Thr Ile Ser Arg Asp Asn Ser Lys Asn Ile Leu Tyr Phe
65                  70                  75                  80

Gln Met Asn Ser Leu Arg Val Glu Asp Thr Ala Val Tyr Tyr Cys Ala
                85                  90                  95

Glu Gly Tyr Gly Gly Val Asp Tyr Trp Gly Gln Gly Thr Leu Val Thr
            100                 105                 110

Val Ser Ser
        115

<210> SEQ ID NO 48
<211> LENGTH: 112
<212> TYPE: PRT
<213> ORGANISM: Homo Sapiens

<400> SEQUENCE: 48

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Ala Tyr
            20                  25                  30

Asn Phe Val Ser Trp Tyr Gln Gln His Ala Gly Lys Gly Pro Lys Leu
        35                  40                  45

Leu Ile Tyr Asp Val Thr Asn Arg Pro Ser Gly Val Ser Asp Arg Phe
    50                  55                  60

Ser Gly Ser Lys Ser Gly Asn Thr Ala Ser Leu Thr Ile Ser Gly Leu

-continued

```
                65                  70                  75                  80
Gln Ala Asp Asp Glu Ala Asp Tyr Phe Cys Ala Ser Tyr Thr Ala Thr
                    85                  90                  95

Thr Thr Leu Gly Tyr Val Phe Gly Thr Gly Thr Lys Leu Thr Val Leu
                100                 105                 110
```

<210> SEQ ID NO 49
<211> LENGTH: 116
<212> TYPE: PRT
<213> ORGANISM: Homo Sapiens

<400> SEQUENCE: 49

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Asn Ser Asn
                20                  25                  30

His Met Ser Trp Val Arg Gln Ala Pro Gly Lys Gly Leu Glu Trp Val
                35                  40                  45

Ser Leu Ile Tyr Asn Gly Asp Asn Thr Tyr Tyr Ala Asp Ser Val Lys
            50                  55                  60

Gly Arg Phe Thr Ile Ser Arg Asp Asn Pro Lys Asn Thr Leu Tyr Leu
65                  70                  75                  80

Gln Met Asn Arg Leu Arg Asp Glu Asp Thr Ala Val Tyr Tyr Cys Ala
                85                  90                  95

Arg Asp Trp Gly Tyr Asn Val Gly Asp Trp Gly Gln Gly Thr Leu Val
                100                 105                 110

Thr Val Ser Ser
            115
```

<210> SEQ ID NO 50
<211> LENGTH: 111
<212> TYPE: PRT
<213> ORGANISM: Homo Sapiens

<400> SEQUENCE: 50

```
Leu Pro Val Leu Thr Gln Pro Arg Ser Val Ser Gly Ser Pro Gly Gln
1               5                   10                  15

Ser Val Thr Ile Ser Cys Thr Gly Thr Ser Asp Asp Val Gly Phe Tyr
                20                  25                  30

Asn Tyr Val Ser Trp Tyr Gln Gln His Pro Gly Lys Ala Pro Lys Leu
                35                  40                  45

Leu Ile Tyr Asp Val Thr Lys Arg Pro Ser Gly Val Pro Asp Arg Phe
            50                  55                  60

Ser Gly Ser Lys Ser Gly Asn Thr Ala Ser Leu Thr Ile Ser Gly Leu
65                  70                  75                  80

Gln Ala Glu Asp Asp Ala Asp Tyr Tyr Cys Ser Ser Tyr Gly Gly Ser
                85                  90                  95

Asn Asn Phe Val Ile Phe Gly Gly Gly Thr Lys Val Thr Val Leu
                100                 105                 110
```

<210> SEQ ID NO 51
<211> LENGTH: 117
<212> TYPE: PRT
<213> ORGANISM: Homo Sapiens

<400> SEQUENCE: 51

```
Gln Val Gln Leu Val Glu Ser Gly Gly Gly Leu Val Gln Pro Gly Gly
1               5                   10                  15
```

```
Ser Leu Arg Leu Ser Cys Ala Ala Ser Thr Phe Thr Phe Ser Arg Tyr
         20                  25                  30

Pro Met Thr Trp Val Arg Gln Ala Pro Gly Lys Gly Leu Glu Trp Val
             35                  40                  45

Ser Ser Ile Ser Gly Gly Gly Asp Thr Thr Tyr Ala Asp Ser Val
 50                  55                  60

Lys Gly Arg Phe Ala Ile Ala Arg Asp Asn Ser Lys Asn Thr Val Ser
 65                  70                  75                  80

Leu Glu Met Ile Ser Leu Arg Ala Glu Asp Thr Ala Val Tyr Tyr Cys
                 85                  90                  95

Ala Lys Asp Trp Leu Tyr Arg Gly Gly Pro Trp Gly Gln Gly Thr Leu
            100                 105                 110

Val Thr Val Ser Ser
            115

<210> SEQ ID NO 52
<211> LENGTH: 109
<212> TYPE: PRT
<213> ORGANISM: Homo Sapiens

<400> SEQUENCE: 52

Gln Pro Val Leu Thr Gln Pro Ala Ser Val Ser Gly Ser Pro Gly Gln
1               5                   10                  15

Pro Ile Thr Ile Ser Cys Thr Gly Thr Ser Ser Asp Val Gly Gly Tyr
            20                  25                  30

Asn His Val Ser Trp Tyr Gln Gln Tyr Pro Gly Glu Ala Pro Lys Val
        35                  40                  45

Met Ile Phe Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Asp Asp Glu Ala Asp Tyr Tyr Cys Asn Ser Leu Thr Ser Ser
                85                  90                  95

Gly Tyr Val Phe Gly Thr Gly Thr Lys Val Thr Val Leu
            100                 105

<210> SEQ ID NO 53
<211> LENGTH: 116
<212> TYPE: PRT
<213> ORGANISM: Homo Sapiens

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Trp Gly Glu Asn Glu Tyr Trp Gly Gln Gly Thr Leu Val
            100                 105                 110
```

Thr Val Ser Ser
        115

<210> SEQ ID NO 54
<211> LENGTH: 113
<212> TYPE: PRT
<213> ORGANISM: Homo Sapiens

<400> SEQUENCE: 54

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Gly Tyr
            20                  25                  30

Asn Tyr Val Ser Trp Tyr Gln Gln His Pro Asp Lys Ala Pro Lys Leu
        35                  40                  45

Met Ile Tyr Asp Val Ser Ser Arg Pro Ser Gly Val Ser Asn Arg Phe
    50                  55                  60

Ser Gly Ser Lys Ser Gly Ser Thr Ala Ser Leu Thr Ile Ser Gly Leu
65                  70                  75                  80

Gln Pro Glu Asp Glu Ala Asp Tyr Tyr Cys Ile Ser Tyr Thr Asn Ser
                85                  90                  95

Asn Ile Phe Gly Gly Tyr Val Phe Gly Thr Gly Thr Lys Leu Thr Val
            100                 105                 110

Leu

<210> SEQ ID NO 55
<211> LENGTH: 119
<212> TYPE: PRT
<213> ORGANISM: Homo Sapiens

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Tyr
            20                  25                  30

Tyr Met His Trp Leu Arg Gln Val Pro Gly Gln Gly Phe Glu Trp Met
        35                  40                  45

Gly Trp Ile Ser Pro Lys Thr Gly Asp Thr Asn Ser Pro Gln Thr Phe
    50                  55                  60

His Gly Arg Val Thr Met Thr Ile Asp Thr Ser Ile Asn Thr Ala Tyr
65                  70                  75                  80

Met Glu Met Asn Arg Leu Arg Ser Asp Asp Thr Ala Val Tyr Tyr Cys
                85                  90                  95

Ala Arg Glu Ala Leu Ile Glu Asp Ala Phe Asp Ile Trp Gly Gln Gly
            100                 105                 110

Thr Met Val Thr Val Ser Ser
        115

<210> SEQ ID NO 56
<211> LENGTH: 111
<212> TYPE: PRT
<213> ORGANISM: Homo Sapiens

<400> SEQUENCE: 56

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Ala

```
            20                  25                  30

Tyr Asp Val His Trp Tyr Gln Gln Leu Pro Gly Thr Ala Pro Lys Leu
            35                  40                  45

Leu Ile Tyr Arg Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Asp Val Val Phe Gly Gly Gly Thr Lys Leu Thr Val Leu
            100                 105                 110

<210> SEQ ID NO 57
<211> LENGTH: 116
<212> TYPE: PRT
<213> ORGANISM: Homo Sapiens

<400> SEQUENCE: 57

Glu Val Gln Leu Val Gln Ser Gly Gly Gly Leu Ile Gln Pro Gly Gly
1               5                   10                  15

Ser Leu Arg Leu Ser Cys Ala Ala Ser Gly Phe Leu Val Ser Ser Lys
            20                  25                  30

Tyr Met Ser Trp Val Arg Gln Ala Pro Gly Lys Gly Leu Glu Trp Val
            35                  40                  45

Ser Val Ile Tyr Thr Asp Gly Ser Thr Tyr Tyr Ala Asp Ser Val Lys
    50                  55                  60

Gly Arg Phe Thr Ile Ser Arg Asp Asn Ser Lys Asn Ala Leu Tyr Leu
65                  70                  75                  80

Gln Met Asn Ser Leu Arg Ala Glu Asp Thr Ala Val Tyr Tyr Cys Ala
                85                  90                  95

Arg Asp Trp Gly Tyr Asp Thr Ala Asp Trp Gly Gln Gly Thr Leu Val
            100                 105                 110

Thr Val Ser Ser
        115

<210> SEQ ID NO 58
<211> LENGTH: 110
<212> TYPE: PRT
<213> ORGANISM: Homo Sapiens

<400> SEQUENCE: 58

Gln Ser Val Val Thr Gln Pro Pro Ser Val Ser Ala Ala Pro Gly Gln
1               5                   10                  15

Lys Ile Ser Ile Ser Cys Ser Gly Ser Ser Ser Asn Val Gly Asn Asn
            20                  25                  30

Tyr Val Ser Trp Tyr Gln Gln Leu Pro Gly Thr Ala Pro Lys Leu Leu
            35                  40                  45

Ile Phe Asp Asn Asn Lys Arg Pro Ser Gly Ile Pro Asp Arg Phe Ser
    50                  55                  60

Gly Ser Lys Ser Gly Thr Ser Ala Thr Leu Gly Ile Ser Gly Leu Gln
65                  70                  75                  80

Thr Gly Asp Glu Ala Asp Tyr Tyr Cys Gly Thr Trp Asp Thr Ser Leu
                85                  90                  95

Arg Ala Leu Val Phe Gly Gly Gly Thr Lys Leu Thr Val Leu
            100                 105                 110
```

<210> SEQ ID NO 59
<211> LENGTH: 114
<212> TYPE: PRT
<213> ORGANISM: Homo Sapiens

<400> SEQUENCE: 59

Glu Val Gln Leu Leu Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Tyr Gly Ile Asp Tyr Trp Gly Gln Gly Thr Leu Val Thr Val
            100                 105                 110

Ser Ser

<210> SEQ ID NO 60
<211> LENGTH: 110
<212> TYPE: PRT
<213> ORGANISM: Homo Sapiens

<400> SEQUENCE: 60

Gln Ser Val Val Thr Gln Pro Pro Ser Val Ser Ala Ala Pro Gly Gln
1               5                   10                  15

Arg Val Thr Ile Ser Cys Ser Gly Ser Ser Ser Asn Ile Glu Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Thr Glu Val Phe Gly Gly Gly Thr Lys Leu Thr Val Leu
            100                 105                 110

<210> SEQ ID NO 61
<211> LENGTH: 116
<212> TYPE: PRT
<213> ORGANISM: Homo Sapiens

<400> SEQUENCE: 61

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

His Met Ala Trp Val Arg Gln Ala Pro Gly Lys Gly Leu Glu Trp Val
        35                  40                  45

Ser Leu Ile Tyr Asn Gly Asp Ser Thr Tyr Tyr Pro Asp Ser Val Lys
    50                  55                  60

-continued

Gly Arg Phe Thr Ile Ser Arg Asp Asn Ser Lys Asn Ala Leu Tyr Leu
65                  70                  75                  80

Gln Met Asn Ser Leu Arg Ala Glu Asp Thr Ala Val Tyr Tyr Cys Ala
                85                  90                  95

Arg Asp Trp Gly Tyr Asp Thr Ala Asp Trp Gly Gln Gly Thr Leu Val
            100                 105                 110

Thr Val Ser Ser
            115

<210> SEQ ID NO 62
<211> LENGTH: 110
<212> TYPE: PRT
<213> ORGANISM: Homo Sapiens

<400> SEQUENCE: 62

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Asn Arg Pro Ser Gly Val Ser Asn Arg Phe
50                  55                  60

Ser Gly Ser Lys Ser Gly Asn Ala Ala Ser Leu Thr Ile Ser Gly Leu
65                  70                  75                  80

Gln Ala Glu Asp Glu Ala Asp Tyr Tyr Cys Ser Ser Tyr Thr Gly Ser
                85                  90                  95

Ser Thr Leu Val Phe Gly Gly Gly Thr Lys Val Thr Val Leu
            100                 105                 110

<210> SEQ ID NO 63
<211> LENGTH: 119
<212> TYPE: PRT
<213> ORGANISM: Homo Sapiens

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Leu Tyr Gly Asp Tyr Phe Asp Tyr Trp Gly Gln Gly
            100                 105                 110

Thr Leu Val Thr Val Ser Ser
            115

<210> SEQ ID NO 64
<211> LENGTH: 111
<212> TYPE: PRT
<213> ORGANISM: Homo Sapiens -continued

```
<400> SEQUENCE: 64

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Ala Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Asn Trp Val Phe Gly Gly Gly Thr Lys Leu Thr Val Leu
            100                 105                 110

<210> SEQ ID NO 65
<211> LENGTH: 116
<212> TYPE: PRT
<213> ORGANISM: Homo Sapiens

<400> SEQUENCE: 65

Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser Gly Tyr Gly Asp Tyr Glu Asp Tyr Trp Gly Gln Gly Thr Leu Val
            100                 105                 110

Thr Val Ser Ser
        115

<210> SEQ ID NO 66
<211> LENGTH: 111
<212> TYPE: PRT
<213> ORGANISM: Homo Sapiens

<400> SEQUENCE: 66

Gln Ser Val Leu Thr Gln Pro Pro Ser Ala Ser Gly Ser Pro Gly Gln
1               5                   10                  15

Ser Val Thr Ile Ser Cys Thr Gly Thr Ser Arg Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Ala Ser Lys Ser Gly Asn Thr Ala Ser Leu Thr Ile Ser Ala Leu
65                  70                  75                  80

Gln Ala Glu Asp Glu Ala Asp Tyr Tyr Cys Thr Ser Tyr Thr Gly Ser
```

```
                85                  90                  95
Ser Pro Pro Tyr Val Phe Gly Thr Gly Thr Lys Val Thr Val Leu
            100                 105                 110

<210> SEQ ID NO 67
<211> LENGTH: 116
<212> TYPE: PRT
<213> ORGANISM: Homo Sapiens

<400> SEQUENCE: 67

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser Gly Tyr Gly Asp Tyr Glu Asp Tyr Trp Gly Gln Gly Thr Leu Val
            100                 105                 110

Thr Val Ser Ser
        115

<210> SEQ ID NO 68
<211> LENGTH: 110
<212> TYPE: PRT
<213> ORGANISM: Homo Sapiens

<400> SEQUENCE: 68

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Trp Pro Ser Gly Ala Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Arg Thr Tyr Val Tyr Gly Thr Gly Thr Lys Val Thr Val Leu
            100                 105                 110

<210> SEQ ID NO 69
<211> LENGTH: 120
<212> TYPE: PRT
<213> ORGANISM: Homo Sapiens

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

```
Ala Ile Ser Trp Val Arg Gln Ala Pro Gly Gln Gly Leu Glu Trp Met
            35                  40                  45
Gly Glu Ile Ile Pro Ile Phe Gly Thr Thr Asn Tyr Ala Gln Lys Phe
 50                  55                  60
Gln Gly Arg Val Thr Ile Ile Ala Asp Glu Ser Thr Ser Thr Ala Tyr
 65                  70                  75                  80
Met Glu Leu Ser Ser Leu Arg Pro Asp Thr Ala Val Tyr Tyr Cys
                 85                  90                  95
Ala Ser Ala Ser Ser Trp Tyr Glu Trp Tyr Phe Asp Val Trp Gly Arg
                100                 105                 110
Gly Thr Leu Val Thr Val Ser Ser
            115                 120

<210> SEQ ID NO 70
<211> LENGTH: 110
<212> TYPE: PRT
<213> ORGANISM: Homo Sapiens

<400> SEQUENCE: 70

Gln Ser Val Leu Thr Gln Pro Arg Ser Val Ser Gly Ser Pro Gly Gln
  1               5                  10                  15
Ser Val Thr Ile Ser Cys Thr Gly Thr Ser Ser Asp Val Gly Gly Tyr
                 20                  25                  30
Asn Tyr Val Ser Trp Tyr Gln Gln His Pro Gly Lys Ala Pro Lys Leu
             35                  40                  45
Met Ile Tyr Asp Val Gly Lys Arg Pro Ser Gly Val Pro Asp Arg Phe
 50                  55                  60
Ser Gly Ser Lys Ser Gly Asn Thr Ala Ser Leu Thr Ile Ser Gly Leu
 65                  70                  75                  80
Gln Ala Glu Asp Glu Ala Asp Tyr Tyr Cys Ser Ser Tyr Thr Ser Ser
                 85                  90                  95
Gly Thr Gln Val Phe Gly Thr Gly Thr Lys Leu Thr Val Leu
                100                 105                 110

<210> SEQ ID NO 71
<211> LENGTH: 114
<212> TYPE: PRT
<213> ORGANISM: Homo Sapiens

<400> SEQUENCE: 71

Glu Val Gln Leu Leu Glu Ser Gly Gly Gly Leu Val Gln Pro Gly Arg
  1               5                  10                  15
Ser Leu Arg Leu Ser Cys Thr Ala Ser Gly Phe Thr Phe Gly Asp Tyr
                 20                  25                  30
Ala Met Ser Trp Phe Arg Gln Ala Pro Gly Lys Gly Leu Glu Trp Val
             35                  40                  45
Ser Val Ile Tyr Ser Gly Gly Ser Thr Tyr Ala Asp Ser Val Lys
 50                  55                  60
Gly Arg Phe Thr Ile Ser Arg His Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Gly Tyr Gly Ile Asp Tyr Trp Gly Gln Gly Thr Leu Val Thr Val
                100                 105                 110
Ser Ser
```

<210> SEQ ID NO 72
<211> LENGTH: 110
<212> TYPE: PRT
<213> ORGANISM: Homo Sapiens

<400> SEQUENCE: 72

Gln Ser Val Val Thr Gln Pro Pro Ser Val Ser Ala Ala Pro Gly Gln
1               5                   10                  15

Arg Val Thr Ile Ser Cys Ser Gly Ser Ser Ser Asn Ile Glu Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Thr Glu Val Phe Gly Gly Gly Thr Lys Leu Thr Val Leu
            100                 105                 110

<210> SEQ ID NO 73
<211> LENGTH: 119
<212> TYPE: PRT
<213> ORGANISM: Homo Sapiens

<400> SEQUENCE: 73

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Lys Phe Ser Asp Asn
            20                  25                  30

Tyr Met Thr Trp Val Arg Gln Ala Pro Gly Lys Gly Leu Glu Trp Val
        35                  40                  45

Ser Tyr Ile Ser Gly Ser Gly Lys Thr Thr His Phe Ala Asp Ser Val
    50                  55                  60

Arg Gly Arg Phe Thr Ile Ser Arg Asp Asn Ala Lys Asn Ser Val Asp
65                  70                  75                  80

Leu Gln Met Asn Ser Leu Arg Val Glu Asp Thr Ala Met Tyr Tyr Cys
                85                  90                  95

Ala Arg Trp Glu Val Gly Val Asp Ala Phe Asp Ile Trp Gly Gln Gly
            100                 105                 110

Thr Met Val Thr Val Ser Ser
        115

<210> SEQ ID NO 74
<211> LENGTH: 108
<212> TYPE: PRT
<213> ORGANISM: Homo Sapiens

<400> SEQUENCE: 74

Leu Leu Val Leu Thr Gln Ser Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser

```
                        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                    85                  90                  95

Pro Val Phe Gly Gly Gly Thr Lys Leu Thr Val Leu
            100                 105

<210> SEQ ID NO 75
<211> LENGTH: 117
<212> TYPE: PRT
<213> ORGANISM: Homo Sapiens

<400> SEQUENCE: 75

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Pro Phe Arg Ser Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
 50                  55                  60

Ser Arg Val Thr Ile Ser Val Asp Arg Ser Lys Asn Gln Phe Ser Leu
 65                  70                  75                  80

Lys Leu Thr Ser Val Thr Ala Ala Asp Thr Ala Val Tyr Tyr Cys Ala
                85                  90                  95

Arg Glu Gly Asp His Glu Ala Phe Asp Ile Trp Gly Gln Gly Thr Met
            100                 105                 110

Val Thr Val Ser Ser
        115

<210> SEQ ID NO 76
<211> LENGTH: 110
<212> TYPE: PRT
<213> ORGANISM: Homo Sapiens

<400> SEQUENCE: 76

Gln Pro Val Leu Thr Gln Pro Pro Ser Val Ser Ala Ala Pro Gly Gln
 1               5                  10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                85                  90                  95

Ser Ser Leu Val Phe Gly Gly Gly Thr Lys Leu Thr Val Leu
            100                 105                 110

<210> SEQ ID NO 77
<211> LENGTH: 116
<212> TYPE: PRT
<213> ORGANISM: Homo Sapiens

<400> SEQUENCE: 77
```

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Asn Ser Asn
            20                  25                  30

His Met Ser Trp Val Arg Gln Ala Pro Gly Lys Gly Leu Glu Trp Val
        35                  40                  45

Ser Leu Ile Tyr Asn Gly Asp Asn Thr Tyr Tyr Ala Asp Ser Val Lys
    50                  55                  60

Gly Arg Phe Thr Ile Ser Arg Asp Asn Pro Lys Asn Thr Leu Tyr Leu
65                  70                  75                  80

Gln Met Asn Arg Leu Arg Asp Glu Asp Thr Ala Val Tyr Tyr Cys Ala
                85                  90                  95

Arg Asp Trp Gly Tyr Asn Val Gly Asp Trp Gly Gln Gly Thr Leu Val
            100                 105                 110

Thr Val Ser Ser
            115

<210> SEQ ID NO 78
<211> LENGTH: 111
<212> TYPE: PRT
<213> ORGANISM: Homo Sapiens

<400> SEQUENCE: 78

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Asn Asn Pro Tyr Val Phe Gly Thr Gly Thr Lys Val Thr Val Leu
            100                 105                 110

<210> SEQ ID NO 79
<211> LENGTH: 117
<212> TYPE: PRT
<213> ORGANISM: Homo Sapiens

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Arg Met Asn Trp Val Arg Gln Ala Pro Gly Lys Gly Leu Glu Trp Val
        35                  40                  45

Ser Ser Ile Ser Ser Asp Ser Asp Phe Tyr Tyr Ala Asp Ser Val
    50                  55                  60

Lys Gly Arg Phe Thr Ile Ser Arg Asp Asn Ala Ile Asn Ser Leu Tyr
65                  70                  75                  80

Leu Gln Met Asn Ser Leu Arg Ala Glu Asp Thr Ala Val Tyr Tyr Cys
                85                  90                  95

```
Ala Arg Asp Trp Gly Tyr Asp Lys Gly Asp Trp Gly Gln Gly Thr Leu
            100                 105                 110
Val Thr Val Ser Ser
        115

<210> SEQ ID NO 80
<211> LENGTH: 113
<212> TYPE: PRT
<213> ORGANISM: Homo Sapiens

<400> SEQUENCE: 80

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Leu Tyr Asn
            20                  25                  30
Ser Asp Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Gly Ser Gly Val
    50                  55                  60
Pro Asp Arg Phe Ser Gly Ser Gly Ser Gly Thr Asp Phe Thr Leu Ser
65                  70                  75                  80
Ile Ser Ser Leu Gln Ala Glu Asp Val Ala Val Tyr Tyr Cys Gln Gln
                85                  90                  95
Tyr Tyr Ser Thr Pro Tyr Thr Phe Gly Gln Gly Thr Lys Val Glu Ile
            100                 105                 110
Lys

<210> SEQ ID NO 81
<211> LENGTH: 123
<212> TYPE: PRT
<213> ORGANISM: Homo Sapiens

<400> SEQUENCE: 81

Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly Tyr
            20                  25                  30
Tyr Trp Ser Trp Ile Arg Gln Thr Pro Gly Lys Gly Leu Glu Trp Ile
        35                  40                  45
Gly Glu Ile Asn His Ser Gly Ser Thr Asn Tyr Asn Pro Ser Leu Lys
    50                  55                  60
Ser Arg Val Thr Ile Ser Ala Asp Thr Ser Arg Asn Gln Phe Ser Leu
65                  70                  75                  80
Arg Leu Ser Ser Val Thr Ala Ala Asp Thr Ala Val Tyr Tyr Cys Ala
                85                  90                  95
Arg Gly Asp Ser Gly Phe Gly Val Val Ser Tyr Tyr Phe Asp Gln
            100                 105                 110
Trp Gly Gln Gly Thr Leu Val Thr Val Ser Ser
        115                 120

<210> SEQ ID NO 82
<211> LENGTH: 108
<212> TYPE: PRT
<213> ORGANISM: Homo Sapiens

<400> SEQUENCE: 82

Ser Tyr Glu Leu Met Gln Pro Pro Ser Glu Ser Val Ala Pro Gly Gln
```

```
1               5                   10                  15
Thr Ala Lys Ile Thr Cys Gly Gly Glu Asn Ile Gly Ser Lys Ser Val
                20                  25                  30

His Trp Tyr Gln Gln Lys Ser Gly Gln Ala Pro Leu Leu Val Val Tyr
                35                  40                  45

Asp Asp Arg Asp Arg Pro Ser Gly Ile Pro Glu Arg Phe Phe Gly Ser
    50                  55                  60

Asn Ser Gly Asp Thr Ala Ser Leu Thr Ile Ser Gly Val Glu Ala Gly
65                  70                  75                  80

Asp Glu Ala Asp Tyr Tyr Cys Gln Val Trp Asp Ser Arg Asn Asp Arg
                85                  90                  95

Val Val Phe Gly Gly Gly Thr Lys Leu Thr Val Leu
                100                 105

<210> SEQ ID NO 83
<211> LENGTH: 118
<212> TYPE: PRT
<213> ORGANISM: Homo Sapiens

<400> SEQUENCE: 83

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
                35                  40                  45

Gly Trp Ile Ser Ala Tyr Asn Gly Asn Thr Asn Tyr Ala Gln Lys Leu
                50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Leu Gly Leu Asp Ala Phe Asp Ile Trp Gly Gln Gly Thr
                100                 105                 110

Met Val Thr Val Ser Ser
        115

<210> SEQ ID NO 84
<211> LENGTH: 110
<212> TYPE: PRT
<213> ORGANISM: Homo Sapiens

<400> SEQUENCE: 84

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
```

<210> SEQ ID NO 85
<211> LENGTH: 117
<212> TYPE: PRT
<213> ORGANISM: Homo Sapiens

<400> SEQUENCE: 85

Glu Val Gln Leu Val Glu Ser Gly Ala Glu Val Lys Lys Pro Gly Ser
1               5                   10                  15

Ser Val Lys Val Ser Cys Lys Ala Ser Gly Tyr Thr Phe Thr Asn Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Lys Ser Glu Asp Thr Ala Val Tyr Tyr Cys
                85                  90                  95

Ala Arg Asp Asp Tyr Tyr Asp Phe Asp Ser Trp Gly Gln Gly Thr Leu
            100                 105                 110

Val Thr Val Ser Ser
        115

<210> SEQ ID NO 86
<211> LENGTH: 110
<212> TYPE: PRT
<213> ORGANISM: Homo Sapiens

<400> SEQUENCE: 86

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Lys Asn
                20                  25                  30

Tyr Val Ser Trp Tyr Gln His Phe Pro Gly Thr Ala Pro Lys Leu Leu
            35                  40                  45

Ile Tyr Asp Asn Asp Glu Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ala Trp Asp Ile Ser Leu
                85                  90                  95

Ser Ala Trp Val Phe Gly Gly Gly Thr Lys Leu Thr Val Leu
            100                 105                 110

<210> SEQ ID NO 87
<211> LENGTH: 118
<212> TYPE: PRT
<213> ORGANISM: Homo Sapiens

<400> SEQUENCE: 87

Gln Val Gln Leu Val Gln Ser Gly Gly Gly Leu Leu Gln Pro Gly Gly
1               5                   10                  15

Ser Leu Arg Leu Ser Cys Ala Ala Ser Gly Phe Thr Phe Ser Asn Tyr
                20                  25                  30

Asp Met His Trp Val Arg Gln Pro Pro Gly Lys Gly Leu Glu Trp Val
            35                  40                  45

```
Ser Ser Ile Asp Thr Ala Gly Asp Thr Tyr Tyr Glu Gly Ser Ala Lys
        50                  55                  60

Gly Arg Phe Thr Ile Ser Arg Asp Asn Ser Ala Asn Thr Leu Tyr Leu
65                  70                  75                  80

Gln Met Asn Ser Leu Thr Thr Glu Asp Thr Ala Val Tyr Tyr Cys Ala
                85                  90                  95

Lys Asp Arg Ile Trp Phe Gly Asp Phe Asp Tyr Trp Gly Gln Gly Thr
                100                 105                 110

Leu Val Thr Val Ser Ser
                115

<210> SEQ ID NO 88
<211> LENGTH: 111
<212> TYPE: PRT
<213> ORGANISM: Homo Sapiens

<400> SEQUENCE: 88

Gln Ala Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Thr Gly Thr Lys Leu Thr Val Leu
                100                 105                 110

<210> SEQ ID NO 89
<211> LENGTH: 120
<212> TYPE: PRT
<213> ORGANISM: Homo Sapiens

<400> SEQUENCE: 89

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gln Leu Leu Trp Ala Pro Phe Asp Tyr Trp Gly Gln
                100                 105                 110

Gly Thr Leu Val Thr Val Ser Ser
                115                 120

<210> SEQ ID NO 90
```

```
<211> LENGTH: 110
<212> TYPE: PRT
<213> ORGANISM: Homo Sapiens

<400> SEQUENCE: 90

Gln Ala Val Leu Thr Gln Pro Pro Ser Val Ser Gly Ala Pro Gly Gln
1               5                   10                  15

Arg Val Thr Ile Ser Cys Thr Gly Ser Asn Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Arg
                85                  90                  95

Leu Ser Ala Val Phe Gly Gly Gly Thr Lys Val Thr Val Leu
            100                 105                 110

<210> SEQ ID NO 91
<211> LENGTH: 116
<212> TYPE: PRT
<213> ORGANISM: Homo Sapiens

<400> SEQUENCE: 91

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Asn Ser Asn
            20                  25                  30

His Met Ser Trp Val Arg Gln Ala Pro Gly Lys Gly Leu Glu Trp Val
        35                  40                  45

Ser Leu Ile Tyr Asn Gly Asp Asn Thr Tyr Tyr Ala Asp Ser Val Lys
50                  55                  60

Gly Arg Phe Thr Ile Ser Arg Asp Asn Pro Lys Asn Thr Leu Tyr Leu
65                  70                  75                  80

Gln Met Asn Arg Leu Arg Asp Glu Asp Thr Ala Val Tyr Tyr Cys Ala
                85                  90                  95

Arg Asp Trp Gly Tyr Asn Val Asp Trp Gly Gln Gly Thr Met Val
            100                 105                 110

Thr Val Ser Ser
        115

<210> SEQ ID NO 92
<211> LENGTH: 112
<212> TYPE: PRT
<213> ORGANISM: Homo Sapiens

<400> SEQUENCE: 92

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Pro His Tyr Val Phe Gly Thr Gly Thr Lys Val Thr Val Leu
            100                 105                 110

<210> SEQ ID NO 93
<211> LENGTH: 117
<212> TYPE: PRT
<213> ORGANISM: Homo Sapiens

<400> SEQUENCE: 93

Gln Met Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Asn Ser Leu Arg Ser Glu Asp Thr Ala Val Tyr Tyr Cys
                 85                  90                  95

Ala Arg Glu Tyr Leu Asp Tyr Phe Asp Tyr Trp Gly Gln Gly Thr Leu
            100                 105                 110

Val Thr Val Ser Ser
            115

<210> SEQ ID NO 94
<211> LENGTH: 112
<212> TYPE: PRT
<213> ORGANISM: Homo Sapiens

<400> SEQUENCE: 94

Gln Ala Gly Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Arg Tyr Val Phe Gly Thr Gly Thr Lys Leu Thr Val Leu
            100                 105                 110

<210> SEQ ID NO 95
<211> LENGTH: 120
<212> TYPE: PRT
<213> ORGANISM: Homo Sapiens

<400> SEQUENCE: 95

Gln Val Gln Leu Val Glu Ser Gly Gly Gly Leu Val Gln Pro Gly Gly
```

```
               1               5                  10                 15
Ser Leu Arg Leu Ser Cys Ala Ala Ser Gly Phe Thr Phe Ser Ser Tyr
            20                  25                 30

Glu Met Asn Trp Val Arg Gln Ala Pro Gly Lys Gly Leu Glu Trp Val
            35                  40                 45

Ser Tyr Ile Ser Ser Ser Gly Ser Thr Ile Tyr Tyr Ala Asp Ser Val
            50                  55                 60

Lys Gly Arg Phe Thr Ile Ser Arg Asp Asn Ala Lys Asn Ser Leu Tyr
65                  70                  75                 80

Leu Gln Met Asn Ser Leu Arg Ala Glu Asp Thr Ala Val Tyr Tyr Cys
                    85                  90                 95

Ala Arg Val Gln Gln Trp Pro Asp Asp Ala Phe Asp Ile Trp Gly Gln
                    100                 105                110

Gly Thr Thr Val Thr Val Ser Ser
            115                 120
```

<210> SEQ ID NO 96
<211> LENGTH: 110
<212> TYPE: PRT
<213> ORGANISM: Homo Sapiens

<400> SEQUENCE: 96

```
Gln Ser Val Leu Thr Gln Pro Pro Ser Ala Ser Gly Ala Pro Gly Gln
1               5                   10                 15

Arg Val Thr Ile Ser Cys Ser Gly Ser Ser Asn Ile Gly Ser Asp
            20                  25                 30

Thr Leu Asp Trp Tyr Gln Gln Leu Pro Gly Thr Ala Pro Lys Leu Leu
            35                  40                 45

Ile Tyr Ser Asn Asn Gln Arg Pro Ser Gly Val Pro Asp Arg Phe Ser
            50                  55                 60

Gly Ser Lys Ser Gly Thr Ser Ala Ser Leu Ala Ile Ser Gly Leu Gln
65                  70                  75                 80

Ser Glu Asp Glu Ala Asn Tyr Tyr Cys Ala Ala Trp Asp Ala Ser Leu
                    85                  90                 95

Asn Gly Trp Val Phe Gly Gly Gly Thr Lys Leu Thr Val Leu
            100                 105                110
```

<210> SEQ ID NO 97
<211> LENGTH: 116
<212> TYPE: PRT
<213> ORGANISM: Homo Sapiens

<400> SEQUENCE: 97

```
Gln Ile Thr Leu Lys Glu Ser Gly Gly Gly Val Val Arg Pro Gly Gly
1               5                   10                 15

Ser Leu Arg Leu Ser Cys Ala Ala Ser Gly Phe Thr Phe Asp Asp Tyr
            20                  25                 30

Gly Met Ser Trp Val Arg Gln Ala Pro Gly Lys Gly Leu Glu Trp Val
            35                  40                 45

Ser Ser Phe Gly Ser Ser Ala Arg Asn Ile Tyr Tyr Ala Asp Ser Val
            50                  55                 60

Lys Gly Arg Phe Ser Ile Ser Arg Asp Asn Ala Lys Asn Ser Leu Tyr
65                  70                  75                 80

Leu Gln Val Asn Ser Leu Arg Asp Glu Asp Thr Ala Val Tyr Tyr Cys
                    85                  90                 95

Ala Arg Gly Ala Tyr Tyr Met Asp Val Trp Gly Asn Gly Thr Thr Val
```

```
                    100                 105                 110
Thr Val Ser Ser
        115

<210> SEQ ID NO 98
<211> LENGTH: 107
<212> TYPE: PRT
<213> ORGANISM: Homo Sapiens

<400> SEQUENCE: 98

Ala Ile Arg Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
                100                 105

<210> SEQ ID NO 99
<211> LENGTH: 119
<212> TYPE: PRT
<213> ORGANISM: Homo Sapiens

<400> SEQUENCE: 99

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Trp Asp Thr Asp Ala Phe Asp Ile Trp Gly Gln Gly
                100                 105                 110

Thr Met Val Thr Val Ser Ser
        115

<210> SEQ ID NO 100
<211> LENGTH: 110
<212> TYPE: PRT
<213> ORGANISM: Homo Sapiens

<400> SEQUENCE: 100

Gln Ala Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30
```

```
Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Tyr Val Phe Gly Thr Gly Thr Lys Val Thr Val Leu
             100                 105                 110

<210> SEQ ID NO 101
<211> LENGTH: 115
<212> TYPE: PRT
<213> ORGANISM: Homo Sapiens

<400> SEQUENCE: 101

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Gly Ser Asn Asn
             20                  25                  30

Tyr Met Ser Trp Val Arg Gln Ala Pro Gly Lys Gly Leu Glu Trp Val
            35                  40                  45

Ser Ile Ile Tyr Ser Gly Gly Asn Ala Tyr Tyr Ala Asp Ser Val Lys
 50                  55                  60

Gly Arg Phe Thr Ile Ser Arg Asp Asn Ser Lys Asn Ile Leu Tyr Phe
 65                  70                  75                  80

Gln Met Asn Ser Leu Arg Val Glu Asp Thr Ala Val Tyr Tyr Cys Ala
                 85                  90                  95

Glu Gly Tyr Gly Gly Val Asp Tyr Trp Gly Gln Gly Thr Leu Val Thr
             100                 105                 110

Val Ser Ser
       115

<210> SEQ ID NO 102
<211> LENGTH: 110
<212> TYPE: PRT
<213> ORGANISM: Homo Sapiens

<400> SEQUENCE: 102

Gln Ser Val Val Thr Gln Pro Pro Ser Val Ser Ala Ala Pro Gly Gln
 1               5                  10                  15

Lys Val Thr Ile Ser Cys Ser Gly Ser Ser Ser Asn Ile Gly Ser Asn
             20                  25                  30

Ser Val Ser Trp Phe Gln His Leu Pro Gly Thr Ala Pro Lys Leu Leu
            35                  40                  45

Ile Tyr Asp Asn Asn Gln Arg Pro Ser Asn Ile Pro Asp Arg Phe Ser
 50                  55                  60

Gly Ser Lys Ser Gly Ala Ser Ala Thr Leu Gly Ile Thr Gly Leu Gln
 65                  70                  75                  80

Thr Gly Asp Glu Ala Asp Tyr Tyr Cys Gly Thr Trp Asp His Arg Leu
                 85                  90                  95

Asn Thr Tyr Val Phe Gly Thr Gly Thr Lys Val Thr Val Leu
             100                 105                 110

<210> SEQ ID NO 103
```

```
<211> LENGTH: 116
<212> TYPE: PRT
<213> ORGANISM: Homo Sapiens

<400> SEQUENCE: 103

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

His Met Ala Trp Val Arg Gln Ala Pro Gly Lys Gly Leu Glu Trp Val
        35                  40                  45

Ser Leu Ile Tyr Asn Gly Asp Ser Thr Tyr Tyr Pro Asp Ser Val Lys
    50                  55                  60

Gly Arg Phe Thr Ile Ser Arg Asp Asn Ser Lys Asn Ala Leu Tyr Leu
65                  70                  75                  80

Gln Met Asn Ser Leu Arg Ala Glu Asp Thr Ala Val Tyr Tyr Cys Ala
                85                  90                  95

Arg Asp Trp Gly Tyr Asp Thr Ala Asp Trp Gly Gln Gly Thr Leu Val
            100                 105                 110

Thr Val Ser Ser
        115

<210> SEQ ID NO 104
<211> LENGTH: 110
<212> TYPE: PRT
<213> ORGANISM: Homo Sapiens

<400> SEQUENCE: 104

Ser Tyr Glu Leu Met Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Tyr Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110

<210> SEQ ID NO 105
<211> LENGTH: 117
<212> TYPE: PRT
<213> ORGANISM: Homo Sapiens

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60
```

```
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Tyr Leu Asp Tyr Phe Asp Tyr Trp Gly Gln Gly Thr Leu
            100                 105                 110

Val Thr Val Ser Ser
        115

<210> SEQ ID NO 106
<211> LENGTH: 110
<212> TYPE: PRT
<213> ORGANISM: Homo Sapiens

<400> SEQUENCE: 106

Gln Ser Val Val Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Tyr Val Phe Gly Thr Gly Thr Lys Val Thr Val Leu
            100                 105                 110

<210> SEQ ID NO 107
<211> LENGTH: 116
<212> TYPE: PRT
<213> ORGANISM: Homo Sapiens

<400> SEQUENCE: 107

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

His Met Ala Trp Val Arg Gln Ala Pro Gly Lys Gly Leu Glu Trp Val
        35                  40                  45

Ser Leu Ile Tyr Asn Gly Asp Ser Thr Tyr Tyr Pro Asp Ser Val Lys
 50                  55                  60

Gly Arg Phe Thr Ile Ser Arg Asp Asn Ser Lys Asn Ala Leu Tyr Leu
 65                  70                  75                  80

Gln Met Asn Ser Leu Arg Ala Glu Asp Thr Ala Val Tyr Tyr Cys Ala
                 85                  90                  95

Arg Asp Trp Gly Tyr Asp Thr Ala Asp Trp Gly Gln Gly Thr Leu Val
            100                 105                 110

Thr Val Ser Ser
        115

<210> SEQ ID NO 108
<211> LENGTH: 110
<212> TYPE: PRT
<213> ORGANISM: Homo Sapiens
```

```
<400> SEQUENCE: 108

Gln Pro Val Leu Thr Gln Pro Ala Ser Val Ser Gly Ser Pro Gly Gln
1               5                   10                  15

Ser Ile Ala Ile Ser Cys Ser Gly Thr Ser Ser Asp Ile Gly Thr Tyr
            20                  25                  30

Asp Ser Val Ser Trp Tyr Gln Gln His Pro Gly Lys Ala Pro Lys Val
        35                  40                  45

Ile Ile Tyr Glu Val Asp Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe Val Phe Gly Thr Gly Thr Lys Leu Thr Val Leu
            100                 105                 110

<210> SEQ ID NO 109
<211> LENGTH: 116
<212> TYPE: PRT
<213> ORGANISM: Homo Sapiens

<400> SEQUENCE: 109

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Asn Ser Asn
            20                  25                  30

His Met Ser Trp Val Arg Gln Ala Pro Gly Lys Gly Leu Glu Trp Val
        35                  40                  45

Ser Leu Ile Tyr Asn Gly Asp Asn Thr Tyr Tyr Ala Asp Ser Val Lys
    50                  55                  60

Gly Arg Phe Thr Ile Ser Arg Asp Asn Pro Lys Asn Thr Leu Tyr Leu
65                  70                  75                  80

Gln Met Asn Arg Leu Arg Asp Glu Asp Thr Ala Val Tyr Tyr Cys Ala
                85                  90                  95

Arg Asp Trp Gly Tyr Asn Val Gly Asp Trp Gly Gln Gly Thr Leu Val
            100                 105                 110

Thr Val Ser Ser
        115

<210> SEQ ID NO 110
<211> LENGTH: 110
<212> TYPE: PRT
<213> ORGANISM: Homo Sapiens

<400> SEQUENCE: 110

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Thr Asn
            20                  25                  30

Thr Val Asn Trp Tyr Gln Gln Val Pro Gly Thr Ala Pro Lys Leu Leu
        35                  40                  45

Ile His Gly Asn Asp Gln Arg Pro Ser Gly Val Pro Asp Arg Phe Ser
    50                  55                  60

Gly Ser Lys Ser Asp Thr Ser Ala Ser Leu Ala Ile Thr Gly Leu Gln
65                  70                  75                  80

Ser Asp Asp Asp Ala Asp Tyr Tyr Cys Ser Ala Trp Asp Ser Leu
```

```
                    85                  90                  95

Asn Ala Asp Val Phe Gly Gly Gly Thr Lys Leu Thr Val Leu
                100                 105                 110

<210> SEQ ID NO 111
<211> LENGTH: 118
<212> TYPE: PRT
<213> ORGANISM: Homo Sapiens

<400> SEQUENCE: 111

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Ser Gly Ser Tyr Ser Asp Phe Asp Tyr Trp Gly Gln Gly Thr
                100                 105                 110

Leu Val Thr Val Ser Ser
            115

<210> SEQ ID NO 112
<211> LENGTH: 108
<212> TYPE: PRT
<213> ORGANISM: Homo Sapiens

<400> SEQUENCE: 112

Ser Tyr Glu Leu Met Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Ile Leu Val Ile Tyr
            35                  40                  45

Tyr Asp Asp Asp Arg Pro Ser Gly Ile Pro Glu Arg Phe Ser Gly Ser
        50                  55                  60

Lys Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Ser Tyr Thr Tyr His
                85                  90                  95

Val Val Phe Gly Gly Gly Thr Lys Leu Thr Val Leu
                100                 105

<210> SEQ ID NO 113
<211> LENGTH: 113
<212> TYPE: PRT
<213> ORGANISM: Homo Sapiens

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
                20                  25                  30
```

```
Asp Met Asn Trp Val Arg Gln Ala Pro Gly Lys Gly Leu Glu Trp Ile
            35                   40                  45

Ser Tyr Ile Ser Ser Ser Gly Ser Ala Ile Phe Tyr Ala Asp Ser Val
        50                  55                  60

Lys Gly Arg Phe Thr Ile Ser Arg Asp Asn Ala Gly Asn Ser Val Tyr
65                  70                  75                  80

Leu Gln Met Asn Ser Leu Arg Ala Glu Asp Thr Ala Ile Tyr Tyr Cys
                85                  90                  95

Ala Arg Arg Phe Asp Tyr Trp Gly Gln Gly Thr Leu Val Thr Val Ser
            100                 105                 110

Ser

<210> SEQ ID NO 114
<211> LENGTH: 113
<212> TYPE: PRT
<213> ORGANISM: Homo Sapiens

<400> SEQUENCE: 114

Asp Ile Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Leu Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Asn Ile
65                  70                  75                  80

Thr Arg Val Glu Thr Asp Val Gly Ile Tyr Tyr Cys Met Gln Gly
                85                  90                  95

Thr His Trp Pro Pro Phe Thr Phe Gly Pro Gly Thr Lys Val Asp Ile
            100                 105                 110

Lys

<210> SEQ ID NO 115
<211> LENGTH: 113
<212> TYPE: PRT
<213> ORGANISM: Homo Sapiens

<400> SEQUENCE: 115

Gln Val Gln Leu Val Glu Ser Gly Gly Gly Val Phe Gln Pro Gly Arg
1               5                   10                  15

Ser Leu Arg Leu Ser Cys Ser Thr Ser Gly Phe Thr Phe Ser Ser Tyr
            20                  25                  30

Asp Met Asn Trp Val Arg Gln Ala Pro Gly Lys Gly Leu Glu Trp Leu
            35                  40                  45

Ser Tyr Ile Ser Ser Ser Gly Ser Ala Met Phe Tyr Ala Asp Ser Val
        50                  55                  60

Lys Gly Arg Phe Thr Ile Ser Arg Asp Thr Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gln Phe Asp Gln Trp Gly Gln Gly Thr Leu Val Thr Val Ser
            100                 105                 110

Ser
```

<210> SEQ ID NO 116
<211> LENGTH: 113
<212> TYPE: PRT
<213> ORGANISM: Homo Sapiens

<400> SEQUENCE: 116

Asp Ile Val Met Thr Gln Ser Pro Leu Ser Leu Pro Val Ala Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser His Arg Asp Ser Gly Val Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Leu Gly Ile Tyr Tyr Cys Ala Gln Gly
                85                  90                  95

Thr His Trp Pro Pro Phe Thr Phe Gly Gln Gly Thr Lys Leu Glu Ile
            100                 105                 110

Lys

<210> SEQ ID NO 117
<211> LENGTH: 122
<212> TYPE: PRT
<213> ORGANISM: Homo Sapiens

<400> SEQUENCE: 117

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Arg Phe Leu Pro Tyr Pro Gly Gly Met Asp Val Trp
            100                 105                 110

Gly Gln Gly Thr Thr Val Thr Val Ser Ser
        115                 120

<210> SEQ ID NO 118
<211> LENGTH: 110
<212> TYPE: PRT
<213> ORGANISM: Homo Sapiens

<400> SEQUENCE: 118

Gln Pro Val Leu Thr Gln Pro Pro Ser Ala Ser Val Ala Pro Gly Gln
1               5                   10                  15

Arg Val Thr Ile Ser Cys Ser Gly Thr Ser Asn Ile Glu Tyr Asn
            20                  25                  30

Ser Val His Trp Tyr Gln Gln Leu Pro Gly Ala Ala Pro Lys Leu Leu

```
              35                  40                  45
Ile Tyr Asn Thr Asp Lys Arg Pro Pro Gly Ile Pro Asp Arg Phe Ser
 50                  55                  60

Ala Ser Lys Ser Gly Thr Ser Ala Ser Leu Ala Ile Ser Gly Leu Arg
 65                  70                  75                  80

Ser Glu Asp Glu Ala Thr Tyr Tyr Cys Ala Thr Trp Asp Asp Ser Leu
                 85                  90                  95

Ser Val Met Leu Phe Gly Gly Gly Thr Lys Val Thr Val Leu
                100                 105                 110

<210> SEQ ID NO 119
<211> LENGTH: 113
<212> TYPE: PRT
<213> ORGANISM: Homo Sapiens

<400> SEQUENCE: 119

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
                 20                  25                  30

Asp Met Asn Trp Val Arg Gln Ala Pro Gly Lys Gly Leu Glu Trp Val
             35                  40                  45

Ser Tyr Ile Ser Ser Gly Ser Thr Ile Tyr Tyr Ala Asp Ser Val
 50                  55                  60

Lys Gly Arg Phe Thr Ile Ser Arg Asp Ser Ala Glu Lys Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Ile Asp Ser Trp Gly Gln Gly Thr Leu Val Thr Val Ser
                100                 105                 110

Ser

<210> SEQ ID NO 120
<211> LENGTH: 113
<212> TYPE: PRT
<213> ORGANISM: Homo Sapiens

<400> SEQUENCE: 120

Asp Ile Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Ser
                 20                  25                  30

Asp Gly Asn Thr Tyr Leu Asn Trp Phe Gln Gln Arg Pro Gly Gln Ser
             35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Pro Tyr Thr Phe Gly Gln Gly Thr Lys Leu Glu Ile
                100                 105                 110

Lys

<210> SEQ ID NO 121
<211> LENGTH: 113
```

<212> TYPE: PRT
<213> ORGANISM: Homo Sapiens

<400> SEQUENCE: 121

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Asn Trp Val Arg Gln Ala Pro Gly Lys Gly Leu Glu Trp Leu
        35                  40                  45

Ser Tyr Ile Ser Ser Ser Gly Ser Ala Met Phe Tyr Ala Asp Ser Val
    50                  55                  60

Lys Gly Arg Phe Thr Ile Ser Arg Asp Thr Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gln Phe Asp Gln Trp Gly Gln Gly Thr Leu Val Thr Val Ser
            100                 105                 110

Ser

<210> SEQ ID NO 122
<211> LENGTH: 113
<212> TYPE: PRT
<213> ORGANISM: Homo Sapiens

<400> SEQUENCE: 122

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Ile Ser Asn Arg Asp Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln Gly
                85                  90                  95

Ser His Trp Pro Pro Phe Thr Phe Gly Pro Gly Thr Lys Val Asp Ile
            100                 105                 110

Lys

<210> SEQ ID NO 123
<211> LENGTH: 117
<212> TYPE: PRT
<213> ORGANISM: Homo Sapiens

<400> SEQUENCE: 123

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Ser Asn Asn
            20                  25                  30

Tyr Met Ser Trp Val Arg Gln Ala Pro Gly Lys Gly Leu Glu Trp Val
        35                  40                  45

Ser Val Ile Tyr Gly Gly Gly Ser Thr Phe Tyr Ala Asn Ser Val Lys
    50                  55                  60

```
Gly Arg Phe Thr Ile Ser Arg Asp Asn Ser Glu Asn Thr Leu Tyr Leu
 65                  70                  75                  80

Gln Met Asn Ser Leu Arg Ser Glu Asp Thr Ala Val Tyr Tyr Cys Ala
                 85                  90                  95

Arg Asp Ser Gly Tyr Gly Asp Phe Asp Tyr Trp Gly Gln Gly Thr Leu
            100                 105                 110

Val Thr Val Ser Ser
            115

<210> SEQ ID NO 124
<211> LENGTH: 107
<212> TYPE: PRT
<213> ORGANISM: Homo Sapiens

<400> SEQUENCE: 124

Asp Val Val Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Asp Ala Tyr Asn Leu Gln Ser Gly Val Pro Ser Lys Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Asn Pro Leu
                 85                  90                  95

Thr Phe Gly Gly Gly Thr Lys Leu Glu Ile Lys
            100                 105

<210> SEQ ID NO 125
<211> LENGTH: 113
<212> TYPE: PRT
<213> ORGANISM: Homo Sapiens

<400> SEQUENCE: 125

Glu Val Gln Leu Val Gln Ser Gly Ala Glu Val Lys Lys Pro Gly Ala
  1               5                  10                  15

Ser Val Lys Val Ser Cys Lys Thr Ser Gly Tyr Thr Phe Thr Gly His
                 20                  25                  30

Tyr Met Asp Trp Val Arg Gln Ala Pro Gly Gln Gly Leu Glu Trp Met
             35                  40                  45

Gly Gly Ile Asn Pro Lys Ser Gly Asp Thr Asp Tyr Ala Gln Lys Phe
 50                  55                  60

Gln Gly Arg Val Thr Met Thr Arg Asp Thr Ser Ile Ser Thr Val Tyr
 65                  70                  75                  80

Ile Glu Leu Asn Ser Leu Thr Ser Asp Asp Thr Ala Met Tyr Tyr Cys
                 85                  90                  95

Ala Arg Asp Phe His Tyr Trp Gly Gln Gly Thr Leu Val Thr Val Ser
            100                 105                 110

Ser

<210> SEQ ID NO 126
<211> LENGTH: 113
<212> TYPE: PRT
<213> ORGANISM: Homo Sapiens

<400> SEQUENCE: 126
```

```
Asp Ile Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu His Ser
            20                  25                  30

Asp Gly Asp Thr Tyr Leu Asn Trp Leu Leu Gln Arg Pro Gly Gln Ser
        35                  40                  45

Pro Arg Arg Leu Ile Tyr Lys Val Ser Ser Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Gly
                85                  90                  95

Ser His Trp Pro Pro Ile Thr Phe Gly Gln Gly Thr Arg Leu Glu Ile
            100                 105                 110

Lys
```

```
<210> SEQ ID NO 127
<211> LENGTH: 117
<212> TYPE: PRT
<213> ORGANISM: Homo Sapiens

<400> SEQUENCE: 127

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Tyr Gly Ala Phe Asp Ile Trp Gly Gln Gly Thr Met
            100                 105                 110

Val Thr Val Ser Ser
        115
```

```
<210> SEQ ID NO 128
<211> LENGTH: 107
<212> TYPE: PRT
<213> ORGANISM: Homo Sapiens

<400> SEQUENCE: 128

Asp Ile Val Met Thr Gln Thr Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Val Ser Gly
    50                  55                  60

Ser Gly Ser Gly Thr Asp Phe Thr Phe Ile Ile Ser Ser Leu Gln Pro
65                  70                  75                  80
```

Glu Asp Ile Gly Thr Tyr Tyr Cys Gln Gln Tyr Asp Asn Leu Pro Tyr
                    85                  90                  95

Thr Phe Gly Gln Gly Thr Lys Val Glu Ile Lys
            100                 105

<210> SEQ ID NO 129
<211> LENGTH: 118
<212> TYPE: PRT
<213> ORGANISM: Homo Sapiens

<400> SEQUENCE: 129

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ser Ser Glu Thr Gly Arg Ile Asp Tyr Trp Gly Gln Gly Thr
            100                 105                 110

Thr Val Thr Val Ser Ser
        115

<210> SEQ ID NO 130
<211> LENGTH: 113
<212> TYPE: PRT
<213> ORGANISM: Homo Sapiens

<400> SEQUENCE: 130

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Gln Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ser His Trp Pro Pro Ile Thr Phe Gly Gln Gly Thr Arg Leu Glu Ile
            100                 105                 110

Lys

<210> SEQ ID NO 131
<211> LENGTH: 116
<212> TYPE: PRT
<213> ORGANISM: Homo Sapiens

<400> SEQUENCE: 131

Glu Val Gln Leu Val Glu Ser Gly Arg Gly Val Val Gln Pro Gly Thr
1               5                   10                  15

```
Ser Leu Arg Leu Ser Cys Ala Ala Ser Gly Phe Thr Phe Ser Arg Phe
         20                  25                  30

Asp Met His Trp Val Arg Gln Ala Pro Gly Lys Gly Leu Glu Trp Val
         35                  40                  45

Ala Phe Ile Ser Tyr Asp Ala Thr Lys Lys Tyr Tyr Ala Asp Ser Val
 50                  55                  60

Arg Gly Arg Phe Thr Ile Ser Arg Asp Asn Ser Lys Asn Thr Phe Tyr
 65                  70                  75                  80

Leu Gln Met Asn Ser Leu Arg Gly Glu Asp Thr Ala Val Tyr Tyr Cys
                 85                  90                  95

Ala Arg Asp Tyr Gly Phe Asp Asn Trp Gly Gln Gly Thr Leu Val
                100                 105                 110

Thr Val Ser Ser
        115

<210> SEQ ID NO 132
<211> LENGTH: 113
<212> TYPE: PRT
<213> ORGANISM: Homo Sapiens

<400> SEQUENCE: 132

Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Leu Val His Ser
         20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Pro Ile Thr Phe Gly Gln Gly Thr Lys Val Glu Ile
                100                 105                 110

Lys

<210> SEQ ID NO 133
<211> LENGTH: 113
<212> TYPE: PRT
<213> ORGANISM: Homo Sapiens

<400> SEQUENCE: 133

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Ile Phe Gly Ser Tyr
         20                  25                  30

Glu Met His Trp Val Arg Gln Ala Pro Gly Lys Gly Leu Glu Trp Val
         35                  40                  45

Ser Tyr Ile Ser Gly Ser Gly Ser Lys Ile Tyr Tyr Ala Asp Ser Val
 50                  55                  60

Lys Gly Arg Phe Thr Ile Ser Arg Asp Asn Ala Lys Asn Ser Val Tyr
 65                  70                  75                  80

Leu Gln Met Asn Ser Leu Gly Ala Glu Asp Thr Ala Val Tyr Tyr Cys
                 85                  90                  95
```

```
Ala Gly Ser Leu Asp Tyr Trp Gly Gln Gly Thr Leu Val Thr Val Ser
            100                 105                 110
Ser
```

<210> SEQ ID NO 134
<211> LENGTH: 113
<212> TYPE: PRT
<213> ORGANISM: Homo Sapiens

<400> SEQUENCE: 134

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Ile Thr Phe Gly Gln Gly Thr Arg Leu Glu Ile
            100                 105                 110

Lys
```

<210> SEQ ID NO 135
<211> LENGTH: 115
<212> TYPE: PRT
<213> ORGANISM: Homo Sapiens

<400> SEQUENCE: 135

```
Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Ser Phe Ser His Lys Ala His Trp Gly Gln Gly Thr Leu Val Thr
            100                 105                 110

Val Ser Ser
        115
```

<210> SEQ ID NO 136
<211> LENGTH: 113
<212> TYPE: PRT
<213> ORGANISM: Homo Sapiens

<400> SEQUENCE: 136

```
Asp Val Val Met Thr Gln Ser Pro Leu Ser Leu Pro Val Thr Leu Gly
1               5                   10                  15
```

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Lys Arg Asp Ser Gly Val Pro
    50                  55                  60

Asp Arg Ile Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Phe Thr Phe Gly Gln Gly Thr Arg Leu Glu Ile
            100                 105                 110

Lys

<210> SEQ ID NO 137
<211> LENGTH: 114
<212> TYPE: PRT
<213> ORGANISM: Homo Sapiens

<400> SEQUENCE: 137

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ala Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Gly Val Tyr Tyr Cys
                85                  90                  95

Ala Gly Arg Ile Phe Asp Ile Trp Gly Gln Gly Thr Met Val Thr Val
            100                 105                 110

Ser Ser

<210> SEQ ID NO 138
<211> LENGTH: 110
<212> TYPE: PRT
<213> ORGANISM: Homo Sapiens

<400> SEQUENCE: 138

Gln Ser Val Val Thr Gln Pro Pro Ser Val Ser Ala Ala Pro Gly Gln
1               5                   10                  15

Arg Val Thr Ile Ser Cys Ser Gly Ser Thr Ser Asn Ile Gly Thr Asn
            20                  25                  30

Tyr Val Ser Trp Phe Gln His Leu Pro Gly Ala Ala Pro Lys Leu Leu
        35                  40                  45

Ile Tyr Asp Asn Ser Glu Arg Pro Ser Gly Ile Pro Asp Arg Phe Ser
    50                  55                  60

Ala Ser Lys Ser Gly Ala Ser Ala Thr Leu Gly Ile Thr Gly Leu Gln
65                  70                  75                  80

Thr Gly Asp Glu Ala Asp Tyr Tyr Cys Gly Thr Trp Asp Asp Ser Leu
                85                  90                  95

Ser Ala Gly Val Phe Gly Gly Gly Thr Lys Val Thr Val Leu
            100                 105                 110

<210> SEQ ID NO 139
<211> LENGTH: 114
<212> TYPE: PRT
<213> ORGANISM: Homo Sapiens

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Ser Ser Tyr
                20                  25                  30

His Met His Trp Val Arg Gln Ala Pro Gly Gln Gly Leu Glu Trp Met
            35                  40                  45

Gly Leu Ile Asp Pro Ser Asp Asp Thr Thr Val Tyr Ala Gln Lys Phe
        50                  55                  60

Gln Gly Arg Val Thr Met Thr Arg Asp Thr Ser Thr Thr Val Tyr
65                  70                  75                  80

Met His Leu Ser Ser Leu Arg Pro Glu Asp Thr Ala Val Tyr Phe Cys
                85                  90                  95

Ala Arg Asp Leu Gly Asn Phe Trp Gly Gln Gly Thr Leu Val Thr Val
                100                 105                 110

Ser Ser

<210> SEQ ID NO 140
<211> LENGTH: 113
<212> TYPE: PRT
<213> ORGANISM: Homo Sapiens

<400> SEQUENCE: 140

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asp Gly Asn Thr Tyr Leu Asn Trp Phe His Gln Arg Pro Gly Gln Ser
            35                  40                  45

Pro Arg Arg Leu Ile Tyr Gln Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Met Gln Gly
                85                  90                  95

Thr His Trp Pro Pro Leu Thr Phe Gly Gly Gly Thr Lys Val Glu Ile
                100                 105                 110

Lys

<210> SEQ ID NO 141
<211> LENGTH: 123
<212> TYPE: PRT
<213> ORGANISM: Homo Sapiens

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

```
Ser Val Ile Tyr Ser Gly Gly Ser Thr Tyr Tyr Ala Asp Ser Val Lys
    50                  55                  60
Gly Arg Phe Thr Ile Ser Arg Asp Asn Ser Lys Asp Thr Leu Tyr Leu
65                  70                  75                  80
Gln Met Asn Ser Leu Arg Gly Glu Asp Thr Ala Val Tyr Tyr Cys Ala
                85                  90                  95
Arg Gly Leu Arg Asp Ser Ser Gly Tyr His Trp Gly Ser Phe Asp Pro
            100                 105                 110
Trp Gly Gln Gly Thr Leu Val Thr Val Ser Ser
            115                 120

<210> SEQ ID NO 142
<211> LENGTH: 108
<212> TYPE: PRT
<213> ORGANISM: Homo Sapiens

<400> SEQUENCE: 142

Ser Ser Glu Leu Thr Gln Asp Pro Ala Val Ser Val Ala Leu Gly Gln
1               5                   10                  15
Thr Val Arg Ile Thr Cys Gln Gly Asp Ser Leu Arg Phe Tyr Phe Ala
            20                  25                  30
Ser Trp Tyr Gln Gln Arg Pro Gly Gln Ala Pro Arg Leu Val Ile Tyr
        35                  40                  45
Gly Glu Asn Glu Arg Pro Ser Gly Ile Pro Asp Arg Phe Ser Ala Ser
    50                  55                  60
Thr Ser Gly Asn Thr Ala Ser Leu Thr Ile Ala Gly Ala Gln Ala Glu
65                  70                  75                  80
Asp Glu Gly Asp Tyr Tyr Cys Asn Ser Arg Asp Asn Asn Asp Gln His
                85                  90                  95
Tyr Val Phe Gly Ser Gly Thr Lys Leu Thr Val Leu
            100                 105
```